(12) United States Patent
Crowley et al.

(10) Patent No.: US 8,067,592 B2
(45) Date of Patent: *Nov. 29, 2011

(54) N-ALKYNY-2-(SUBSTITUTED ARYLOXY) ALKYLTHIOAMINE DERIVATIVES AS FUNGICIDES

(75) Inventors: Patrick Jelf Crowley, Bracknell (GB); Roger Salmon, Bracknell (GB); Olivia Anabelle Sageot, Bracknell (GB); David Philip Bacon, Bracknell (GB); David William Langton, Bracknell (GB)

(73) Assignee: Syngenta Limited, Bracknell (GB)

( * ) Notice: Subject to any disclaimer, the term of this patent is extended or adjusted under 35 U.S.C. 154(b) by 1439 days.

This patent is subject to a terminal disclaimer.

(21) Appl. No.: 10/558,116

(22) PCT Filed: May 28, 2004

(86) PCT No.: PCT/GB2004/002294
§ 371 (c)(1),
(2), (4) Date: Aug. 7, 2006

(87) PCT Pub. No.: WO2004/108663
PCT Pub. Date: Dec. 16, 2004

(65) Prior Publication Data
US 2007/0042996 A1 Feb. 22, 2007

(30) Foreign Application Priority Data
Jun. 4, 2003 (GB) .................................... 0312863.4

(51) Int. Cl.
*C07D 239/74* (2006.01)
*C07D 239/76* (2006.01)
*C07D 217/02* (2006.01)
*C07C 323/15* (2006.01)
*A01N 43/42* (2006.01)
*A01N 43/54* (2006.01)

(52) U.S. Cl. ......... 544/283; 546/141; 546/153; 564/162
(58) Field of Classification Search .................... 546/14, 546/141, 142, 153, 155; 544/283; 564/162
See application file for complete search history.

(56) References Cited

U.S. PATENT DOCUMENTS

| | | | |
|---|---|---|---|
| 3,272,844 A | 9/1966 | Easton et al. | |
| 4,049,423 A | 9/1977 | Baker et al. | |
| 4,062,977 A | 12/1977 | Baker et al. | |
| 4,070,486 A | 1/1978 | Baker et al. | |
| 4,083,867 A | 4/1978 | Baker et al. | |
| 4,116,677 A | 9/1978 | Walker et al. | |
| 4,146,387 A | 3/1979 | Thiele | |
| 4,154,849 A | 5/1979 | Walker et al. | |
| 4,168,319 A | 9/1979 | Walker et al. | |
| 4,784,682 A | 11/1988 | Forster et al. | |
| 6,048,860 A | 4/2000 | Farrar et al. | |
| 6,090,815 A | 7/2000 | Masuda et al. | |
| 6,156,769 A | 12/2000 | Farrar et al. | |
| 7,122,672 B2 * | 10/2006 | Salmon et al. | 546/141 |
| 7,371,764 B2 * | 5/2008 | Crowley et al. | 514/311 |
| 2005/0065032 A1 | 3/2005 | Whittingham et al. | |
| 2006/0019973 A1 | 1/2006 | Salmon et al. | |
| 2006/0058397 A1 | 3/2006 | Salmon | |
| 2006/0140997 A1 | 6/2006 | Pitterna et al. | |
| 2006/0148859 A1 | 7/2006 | Crowley | |
| 2006/0194763 A1 | 8/2006 | Salmon et al. | |

FOREIGN PATENT DOCUMENTS

| | | |
|---|---|---|
| CA | 1132580 | 9/1982 |
| DE | 2731960 A1 | 2/1978 |
| DE | 2948095 A1 | 6/1981 |
| DE | 3702964 A1 | 8/1988 |
| EP | 0001721 A2 | 5/1979 |
| EP | 0 010 298 | 4/1980 |
| EP | 0751120 A2 | 1/1997 |
| EP | 0940392 A1 | 9/1999 |
| FR | 2359816 A1 | 2/1978 |
| JP | 06186702 A | 7/1994 |
| JP | 201089453 A | 4/2001 |
| JP | 04021677 A | 1/2004 |
| WO | WO 99/33810 | 7/1999 |
| WO | WO-99-33810 A1 | 9/2002 |
| WO | WO 03/048128 | 6/2003 |
| WO | 2004047538 A1 | 6/2004 |
| WO | 2004048316 A1 | 6/2004 |
| WO | 2004048337 A1 | 6/2004 |
| WO | 2004052100 A1 | 6/2004 |
| WO | 2004108694 A1 | 12/2004 |
| WO | 2006058699 A1 | 6/2006 |
| WO | 2006058700 A1 | 6/2006 |

OTHER PUBLICATIONS

The Chemistry of Heterocyclic compounds: Quinolines PART 1, Jones, Gurnos editor Wiley: New York, 1977 p. 104-117.*
Gomez et. al. "In vitro antifungal activity of polyfunctionalized 2-(hetero)arylquinolines prepared through imino Diels-Alder reactions" Bioorganic & Medicinal Chemistry 16 (2008) 7908-7920.*
Lamberth "Alkyne chemistry in crop protection" Bioorganic & Medicinal Chemistry 17 (2009) 4047-4063.*

* cited by examiner

*Primary Examiner* — David K O Dell
(74) *Attorney, Agent, or Firm* — James Cueva

(57) ABSTRACT

Fungicidal compounds of the general formula (1), wherein Ar is a group of the formula (A), (B1), (B2) or (C), or Ar is a 5- or 6-linked group of the formula (D1) or (D2); and $R^1$, $R^2$, $R^3$, $R^4$, $R^5$, n, $A^1$, $A^2$, $A^3$, $A^4$, $A^5$, $K^a$, $K^b$, L, M, V, W, X, Y and Z have the definitions given in claim 1.

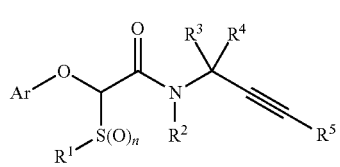

(1)

10 Claims, No Drawings

N-ALKYNY-2-(SUBSTITUTED ARYLOXY) ALKYLTHIOAMINE DERIVATIVES AS FUNGICIDES

This application is a 371 of International Application No. PCT/GB2004/002294 filed May 28, 2004, which claims priority to GB 0312863.4 filed Jun. 4, 2003, the contents of which are incorporated herein by reference.

This invention relates to novel N-alkynyl-2-alkylthio-2-(substituted aryloxy and heteroaryloxy)alkylamides and to their sulphinyl and sulphonyl derivatives. It also relates to processes for preparing them, to compositions containing them and to methods of using them to combat fungi, especially fungal infections of plants.

Certain N-alkynyl-2-(substituted phenoxy)alkylamides are described in U.S. Pat. No. 4,116,677 as being useful as herbicides. Others are described in U.S. Pat. No. 4,168,319 as being useful as mildewicides. Several N-dimethylpropynyl-α-methoxy- and α-ethoxy-α-(substituted phenoxy)acetamides are described in U.S. Pat. No. 4,062,977 for use as miticides and the compound N-dimethylpropynyl-α-methoxy-α-(3,5-dimethylphenoxy)acetamide is described in U.S. Pat. No. 4,083,867 for use as a herbicide.

The present invention is concerned with the provision of particular N-alkynyl-2-alkylthio-2-(substituted aryloxy and heteroaryloxy)alkylamides and their sulphinyl and sulphonyl derivatives for use mainly as plant fungicides.

Thus according to the present invention there is provided a compound of the general formula (1):

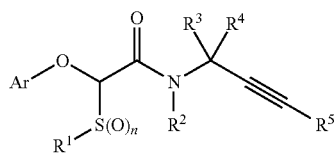

(1)

wherein Ar is a group of the formula (A):

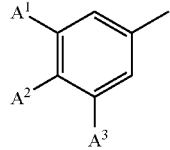

(A)

wherein $A^1$, $A^2$ and $A^3$ are independently H, halogen, $C_{1-4}$ alkyl (e.g. methyl), halo($C_{1-4}$)-alkyl (e.g. trifluoromethyl), $C_{2-4}$ alkenyl, halo($C_{2-4}$)alkenyl, $C_{2-4}$ alkynyl, halo($C_{2-4}$)alkynyl, $C_{1-4}$ alkoxy (e.g. methoxy), halo($C_{1-4}$)alkoxy (e.g. trifluoromethoxy), —S(O)$_m$—($C_{1-4}$)alkyl wherein m is 0, 1 or 2 and the alkyl group is optionally substituted with halo (particularly fluoro, e.g. methylthio, trifluoromethylsulphonyl), —OSO$_2$($C_{1-4}$)alkyl where the alkyl group is optionally substituted with halo (particularly fluoro, e.g. trifluoro-methylsulphonyloxy), cyano, nitro, $C_{1-4}$ alkoxycarbonyl, —CONR'''R'', —COR''', —NR'''COR'', —SO$_2$NR'''R'' or —NR'''SO$_2$R$^1$ where R$^1$ is $C_{1-4}$ alkyl and R''' and R'' are independently H or $C_{1-4}$ alkyl (e.g. —NHCOCH$_3$); or Ar is a group of the formula (B1) or (B2):

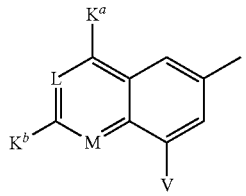

(B1)

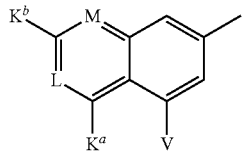

(B2)

wherein L and M are independently N,N-oxide or CQ, except that no more than one of L or M is N-oxide;
$K^a$ and $K^b$ are independently H or F;
V is H, halo (e.g. fluoro, chloro, bromo, iodo), $C_{1-6}$ alkyl optionally substituted with halo or $C_{1-4}$ alkoxy, $C_{3-6}$ cycloalkyl optionally substituted with halo or $C_{1-4}$ alkoxy, $C_{2-4}$ alkenyl optionally substituted with halo, $C_{2-4}$ alkynyl optionally substituted with halo, $C_{1-6}$ alkoxy optionally substituted with halo or $C_{1-4}$ alkoxy, $C_{2-4}$ alkenyloxy optionally substituted with halo (e.g. allyloxy), $C_{2-4}$ alkynyloxy optionally substituted with halo (e.g. propargyloxy), cyano, nitro, $C_{1-4}$ alkoxycarbonyl, —OSO$_2$R', —S(O)$_m$R', —COR'', —CONR''R''', —SO$_2$NR''R''', —NR''SO$_2$R', —CR''=NR''', —NR''R''', —NR''COR''', —NR''CO$_2$R'' where m is 0, 1 or 2, R' is $C_{1-6}$ alkyl optionally substituted with halogen and R'' and R''' are independently H or $C_{1-6}$ alkyl or, in the case of —CONR''R''' or —SO$_2$NR''R''', may join to form a 5- or 6-membered ring containing a single nitrogen atom, saturated carbon atoms and optionally a single oxygen atom;
Q is H, halo, $C_{1-8}$ alkyl, $C_{3-6}$ cycloalkyl, $C_{2-8}$ alkenyl, $C_{2-8}$ alkynyl, $C_{1-8}$ alkoxy, $C_{1-8}$ alkylthio, halo($C_{1-8}$)alkyl, halo($C_{1-8}$)alkoxy, halo($C_{1-8}$)alkylthio, nitro, amino, mono- or di-($C_{1-6}$)alkylamino, mono- or di-($C_{2-6}$)alkenylamino, mono- or di-($C_{2-6}$)alkynylamino, formylamino, $C_{1-4}$ alkyl(formyl)amino, $C_{1-4}$ alkylcarbonylamino, $C_{1-4}$ alkoxycarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$)alkylaminocarbonyl, carboxy, $C_{1-4}$ alkylcarbonyloxy, aryl($C_{1-4}$)alkylcarbonyloxy, $C_{1-4}$ alkylsulphinyl, $C_{1-4}$ alkylsulphonyl or $C_{1-4}$ alkylsulphonyloxy, halo($C_{1-4}$)alkylsulphinyl, halo($C_{1-4}$)alkylsulphonyl, —SO$_2$NR'''R'', —NR'''SO$_2$R$^1$, where R$^1$ is $C_{1-6}$ alkyl optionally substituted with halogen and R''' and R'' are independently H or $C_{1-6}$ alkyl optionally substituted with halogen or, in the case of —SO$_2$NR'''R'', may join to form a 5- or 6-membered ring containing a single nitrogen atom, saturated carbon atoms and optionally a single oxygen atom; or
Ar is a group of the formula (C):

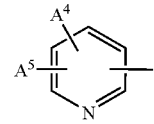

(C)

wherein $A^4$ and $A^5$ are independently H, halo, $C_{1-8}$ alkyl, $C_{3-6}$ cycloalkyl, $C_{2-8}$ alkenyl, $C_{2-8}$ alkynyl, $C_{1-8}$ alkoxy, $C_{1-8}$ alkylthio, nitro, amino, mono- or di-($C_{1-6}$)alkylamino, mono- or di-($C_{2-6}$)alkenylamino, mono- or di-($C_{2-6}$)alkynylamino, formylamino, $C_{1-4}$ alkyl(formyl)amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$)alkyl-aminocarbonyl, carboxy, $C_{1-4}$ alkylcarbonyloxy, aryl($C_{1-4}$)alkylcarbonyloxy, $C_{1-4}$ alkyl-sulphinyl, $C_{1-4}$ alkylsulphonyl, $C_{1-4}$ alkylsulphonyloxy, aryl, heteroaryl, aryloxy, arylthio, heteroaryloxy or heteroarylthio wherein any of the foregoing alkyl, cycloalkyl, alkenyl, alkynyl, aryl or heteroaryl groups or moieties are optionally substituted; or Ar is a 5- or 6-linked group of the formula (D1) or (D2):

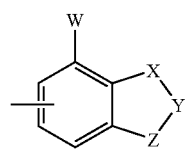

(D1)

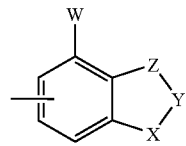

(D2)

wherein W is H, halo, $C_{1-4}$ alkyl, $C_{1-4}$ alkoxy, $C_{1-4}$ alkylthio, $C_{1-4}$ alkylsulphinyl, $C_{1-4}$ alkylsulphonyl, halo($C_{1-4}$)alkyl, halo($C_{1-4}$)alkoxy, halo($C_{1-4}$)alkylthio, halo($C_{1-4}$)alkyl-sulphinyl, halo($C_{1-4}$)alkylsulphonyl, cyano or nitro, X is N, NH or N—$C_{1-4}$ alkyl,
Y is CR, N, NH, N—$C_{1-4}$ alkyl, O or S,
Z is CR, N, NH, N—$C_{1-4}$ alkyl, O or S,
R is H, halo, $C_{1-4}$ alkyl, $C_{1-4}$ alkoxy, $C_{1-4}$ alkylthio, $C_{1-4}$ alkylsulphinyl, $C_{1-4}$ alkyl-sulphonyl, halo($C_{1-4}$)alkyl or halo($C_{1-4}$)alkoxy, halo($C_{1-4}$)alkylthio, halo($C_{1-4}$)alkyl-sulphinyl, halo($C_{1-4}$)alkylsulphonyl or mono- or di-($C_{1-4}$) alkylamino, the bonds joining X, Y, Z and the fused benzene ring are double or single bonds appropriate to the valencies of X, Y and Z, provided that only one of Y and Z may be O or S, that only one of Y and Z may be CH or CR and that only one of X, Y and Z may be NH or N—$C_{1-4}$ alkyl;

$R^1$ is methyl or ethyl;
$R^2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy;
$R^3$ and $R^4$ are independently H, $C_{1-3}$ alkyl, $C_{2-3}$ alkenyl or $C_{2-3}$ alkynyl provided that both are not H and that when both are other than H their combined total of carbon atoms does not exceed 4, or
$R^3$ and $R^4$ join with the carbon atom to which they are attached to form a 3 or 4 membered carbocyclic ring optionally containing one O, S or N atom and optionally substituted with halo or $C_{1-4}$ alkyl;
$R^5$ is H, $C_{1-4}$ alkyl or $C_{3-6}$ cycloalkyl in which the alkyl or cycloalkyl group is optionally substituted with halo, hydroxy, $C_{1-6}$ alkoxy, cyano, $C_{1-4}$ alkylcarbonyloxy, aminocarbonyloxy or mono- or di($C_{1-4}$)alkylaminocarbonyloxy, —S(O)$_p$($C_{1-6}$)alkyl where p is 0, 1 or 2, triazolyl (e.g. 1,2,4-triazol-1-yl), pyrazolyl, imidazolyl, tri($C_{1-4}$)-alkylsilyloxy, optionally substituted phenoxy, optionally substituted thienyloxy, optionally substituted benzyloxy or optionally substituted thienylmethoxy, or
$R^5$ is optionally substituted phenyl, optionally substituted thienyl or optionally substituted benzyl, in which the optionally substituted phenyl and thienyl rings or moieties of the $R_5$ values are optionally substituted with one, two or three substituents selected from halo, hydroxy, mercapto, $C_{1-4}$ alkyl, $C_{2-4}$, alkenyl, $C_{2-4}$ alkynyl, $C_{1-4}$ alkoxy, $C_{2-4}$ alkenyloxy, $C_{2-4}$ alkynyloxy, halo ($C_{1-4}$)alkyl, halo($C_{1-4}$) alkoxy, —S(O)$_m$($C_{1-4}$)alkyl wherein m is 0, 1 or 2 and the alkyl is optionally substituted with halo, hydroxy($C_{1-4}$)alkyl, $C_{1-4}$ alkoxy($C_{1-4}$)-alkyl, $C_{3-6}$ cycloalkyl, $C_{3-6}$ cycloalkyl ($C_{1-4}$)alkyl, phenoxy, benzyloxy, benzoyloxy, cyano, isocyano, thiocyanato, isothiocyanato, nitro, —NR$^p$R$^q$, —NHCOR$^p$, —NHCONR$^p$R$^q$, —CONR$^p$R$^q$, —SO$_2$NR$^p$R$^q$, —NR$^p$SO$_2$R$^o$, —SO$_2$R$^o$, —OSO$_2$R$^o$, —COR$^p$, —CR$^p$=NR$^q$ or —N=CR$^p$R$^q$, in which R$^o$ is $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy and R$^p$ and R$^q$ are independently hydrogen, $C_{1-4}$ alkyl, halo($C_{1-4}$)alkyl, $C_{1-4}$ alkoxy, halo($C_{1-4}$)-alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; and n is 0, 1 or 2.

For the avoidance of doubt, the unattached single bond shown in the groups of formulae (A), (B1), (B2), (C), (D1) and (D2) indicates the point of attachment of the Ar group in the compound of formula (1) to the rest of the molecule. In the case of the unattached floating bond in the group of formula (D1) and (D2), the group (D1) or (D2) is attached in either of its 5- or 6-positions.

The compounds of the invention contain at least one asymmetric carbon atom (and at least two when $R^3$ and $R^4$ are different) and may exist as enantiomers (or as pairs of diastereoisomers) or as mixtures of such. Further, when n is 1, the compounds of the invention are sulphoxides, which can exists in two enantiomeric forms, and the adjacent carbon can also exists in two enantiomeric forms. Compounds of general formula (1) can therefore exist as racemates, diastereoisomers, or single enantiomers, and the invention includes all possible isomers or isomer mixtures in all proportions. It is to be expected that for any given compound, one isomer may be more fungicidally active than another.

Except where otherwise stated, alkyl groups and alkyl moieties of alkoxy, alkylthio, etc., suitably contain from 1 to 6, typically from 1 to 4, carbon atoms in the form of straight or branched chains. Examples are methyl, ethyl, n- and isopropyl and n-, sec-, iso- and tert-butyl. Where alkyl moieties contain 5 or 6 carbon atoms, examples are n-pentyl and n-hexyl. Examples of suitable optional substituents of alkyl groups and moieties include halo, hydroxy, $C_{1-4}$ alkoxy and $C_{1-4}$ alkoxy($C_{1-4}$)alkoxy, optionally substituted aryl and optionally substituted heteroaryl. Where the optional substituent is halo, the haloalkyl group or moiety is typically trichloromethyl or trifluoromethyl.

Except where otherwise stated, alkenyl and alkynyl moieties also suitably contain from 2 to 6, typically from 2 to 4, carbon atoms in the form of straight or branched chains. Examples are allyl, ethynyl and propargyl. Optional substituents include halo.

Halo includes fluoro, chloro, bromo and iodo. Most commonly it is fluoro, chloro or bromo and usually fluoro or chloro.

Aryl is usually phenyl but also includes naphthyl, anthryl and phenanthryl. Heteroaryl is typically a 5- or 6-membered aromatic ring containing one or more O, N or S heteroatoms, which may be fused to one or more other aromatic or heteroaromatic rings, such as a benzene ring. Examples are thienyl, furyl, pyrrolyl, isoxazolyl, oxazolyl, thiazolyl, oxadiazolyl, pyrazolyl, imidazolyl, triazolyl, isothiazolyl, tetrazolyl, thiadiazolyl, pyridyl, pyrimidinyl, pyrazinyl, pyridazinyl, triazinyl, benzofuryl, benzo-thienyl, dibenzofuryl, benzothiazolyl, benzoxazolyl, benzimidazolyl, indolyl, quinolinyl and quinoxalinyl groups and, where appropriate, N-oxides and salts thereof. Any of the aryl or heteroaryl values are optionally substituted. Except where otherwise stated, substituents which may be present include one or more of the following: halo, hydroxy, mercapto, $C_{1-8}$ alkyl (especially-methyl and ethyl), $C_{2-6}$ alkenyl (especially allyl), $C_{2-6}$ alkynyl (especially propargyl), $C_{1-6}$ alkoxy (especially methoxy), $C_{2-6}$ alkenyloxy (especially allyloxy), $C_{2-6}$ alkynyloxy (especially propargyloxy), halo($C_{1-8}$)alkyl (especially trifluoromethyl), halo ($C_{1-6}$)alkoxy (especially trifluoromethoxy), $C_{1-6}$ alkylthio (especially methylthio), hydroxy($C_{1-6}$)alkyl, $C_{1-4}$ alkoxy ($C_{1-4}$)alkyl, $C_{1-4}$alkoxy($C_{1-4}$)-alkoxy, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted arylthio (especially optionally substituted phenylthio), optionally substituted heteroarylthio (especially optionally substituted pyridylthio or pyrimidinylthio), optionally substituted aryl($C_{1-4}$)-alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)-alkenyl (especially optionally substituted pyridylethenyl or pyrimidinylethenyl), optionally substituted aryl($C_{1-4}$)alkoxy (especially optionally substituted benzyloxy and phenethyloxy), optionally substituted heteroaryl($C_{1-4}$)alkoxy (especially optionally substituted pyridyl- or pyrimidinyl($C_{1-4}$) alkoxy), optionally substituted aryloxy($C_{1-4}$)alkyl (especially phenoxymethyl), optionally substituted heteroaryloxy-($C_{1-4}$)alkyl (especially optionally substituted pyridyloxy or pyrimidinyloxy($C_{1-4}$)alkyl), optionally substituted aryl($C_{1-4}$)alkylthio (especially optionally substituted benzylthio and phenethylthio), optionally substituted heteroaryl($C_{1-4}$)alkylthio (especially optionally substituted pyridyl or pyrimidinyl($C_{1-4}$)alkylthio), optionally substituted arylthio($C_{1-4}$)alkyl (especially phenylthiomethyl), optionally substituted heteroarylthio($C_{1-4}$)alkyl (especially optionally substituted pyridylthio- or pyrimidinylthio($C_{1-4}$)alkyl), acyloxy, including $C_{1-4}$ alkanoyloxy (especially acetyloxy) and benzoyloxy, cyano, isocyano, thiocyanato, isothiocyanato, nitro, $NR^sR^t$, $-NHCOR^s$, $-NHCONR^sR^t$, $-CONR^sR^t$, $-COOR^s$, $-SO_2R^r$, $-OSO_2R^r$, $-COR^s$, $-CR^s=NR^t$ or $-N=CR^sR^t$ in which $R^r$ is $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy and $R^s$ and $R^t$ are independently hydrogen, $C_{1-4}$ alkyl, halo($C_{1-4}$)-alkyl, $C_{1-4}$ alkoxy, halo($C_{1-4}$) alkoxy, $C_{1-4}$ alkylthio, $C_{3-6}$ cycloalkyl, $C_{3-6}$ cycloalkyl($C_{1-4}$)- alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo ($C_{1-4}$)alkyl, halo($C_{1-4}$)alkoxy, $C_{1-4}$ alkylthio, halo($C_{1-4}$)alkylthio, hydroxy($C_{1-4}$)alkyl, $C_{1-4}$alkoxy($C_{1-4}$)alkyl, $C_{3-6}$ cycloalkyl, $C_{3-6}$ cycloalkyl($C_{1-4}$)alkyl, alkanoyloxy, phenoxy, benzyloxy, benzoyloxy, cyano, isocyano, thiocyanato, isothiocyanato, nitro, $-NR^sR^t$, $-NHCOR^s$, $-NHCONR^sR^t$, $-CONR^sR^t$, $-COOR^s$, $-SO_2R^r$, $-OSO_2R^r$, $-COR^s$, $-CR^s=NR^t$ or $-N=CR^sR^t$, in which $R^r$, $R^s$ and $R^t$ have the meanings given above. The substituents $A^1$, $A^2$ and $A^3$ on the phenyl ring of the group of the formula (A) may provide a 3-, 3,5- or 3,4,5-substituted phenyl ring.

Of particular interest are compounds where Ar is a group of the formula (A):

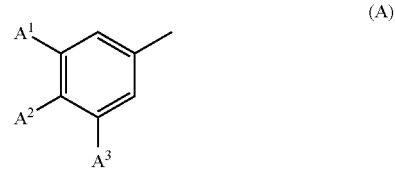

wherein $A^1$, $A^2$ and $A^3$ are independently H, halogen, $C_{1-4}$ alkyl (e.g. methyl), halo($C_{1-4}$)-alkyl (e.g. trifluoromethyl), $C_{2-4}$ alkenyl, halo($C_{2-4}$)alkenyl, $C_{2-4}$ alkynyl, halo($C_{2-4}$)-alkynyl, $C_{1-4}$ alkoxy (e.g. methoxy), halo($C_{1-4}$)alkoxy (e.g. trifluoromethoxy), $-S(O)_m-(C_{1-4})$alkyl wherein m is 0, 1 or 2 and the alkyl group is optionally substituted with fluoro (e.g. methylthio, trifluoromethylsulphonyl), $-OSO_2(C_{1-4})$ alkyl where the alkyl group is optionally substituted with fluoro (e.g. trifluoromethylsulphonyloxy), cyano, nitro, $C_{1-4}$ alkoxycarbonyl, $-CONR^mR^n$, $-COR^m$ or $-NR^mCOR^n$ where $R^m$ and $R^n$ are independently H or $C_{1-4}$ alkyl (e.g. $-NHCOCH_3$); or Ar is a group of the formula (B):

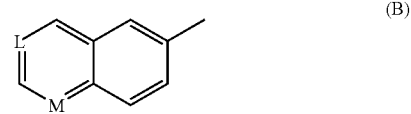

wherein one of L and M is N and the other is CQ or both of L and M are N; Q is H, halo, $C_{1-8}$ alkyl, $C_{3-6}$ cycloalkyl, $C_{2-8}$ alkenyl, $C_{2-8}$ alkynyl, $C_{1-8}$ alkoxy, $C_{1-8}$ alkylthio, halo-($C_{1-8}$) alkyl, halo($C_{1-8}$)alkoxy, nitro, amino, mono- or di-($C_{1-6}$)alkylamino, mono- or di-($C_{2-6}$)alkenylamino, mono- or di-($C_{2-6}$) alkynylamino, formylamino, $C_{1-4}$ alkyl(formyl)-amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl; mono- or di-($C_{1-4}$)alkylamino-carbonyl, carboxy, $C_{1-4}$ alkylcarbonyloxy, aryl($C_{1-4}$)alkylcarbonyloxy, $C_{1-4}$ alkylsulphinyl, $C_{1-4}$ alkylsulphonyl or $C_{1-4}$ alkylsulphonyloxy; or Ar is a group of the formula (C):

wherein $A^4$ and $A^5$ are independently H, halo, $C_{1-8}$ alkyl, $C_{3-6}$ cycloalkyl, $C_{2-8}$ alkenyl, $C_{2-8}$ alkynyl, $C_{1-8}$ alkoxy, $C_{1-8}$ alkylthio, nitro, amino, mono- or di-($C_{1-6}$)alkylamino, mono- or di-($C_{2-6}$)alkenylamino, mono- or di-($C_{2-6}$)alkynylamino, formylamino, $C_{1-4}$ alkyl(formyl)amino, $C_{1-4}$ alkylcarbonylamino, $C_{1-4}$ alkyl($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$)alkyl-aminocarbonyl, carboxy, $C_{1-4}$ alkylcarbonyloxy, aryl($C_{1-4}$)alkylcarbonyloxy, $C_{1-4}$ alkyl-sulphinyl, $C_{1-4}$ alkylsulphonyl, $C_{1-4}$ alkylsulphonyloxy, aryl, heteroaryl, aryloxy, arylthio, heteroaryloxy or heteroarylthio wherein any of the foregoing alkyl, cycloalkyl, alkenyl, alkynyl, aryl, heteroaryl, groups or moieties are optionally substituted; or Ar is a group of the formula (D1)

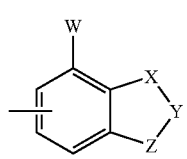

wherein W is H, halo, $C_{1-4}$ alkyl, $C_{1-4}$ alkoxy, halo($C_{1-4}$)alkyl or halo($C_{1-4}$)alkoxy, X is N, NH or N—$C_{1-4}$ alkyl, Y is CH, N, NH, O or S, Z is CH, N, NH, N—$C_{1-4}$ alkyl, O or S, and the bonds joining X, Y, Z and the fused benzene ring are double or single bonds appropriate to the valencies of X, Y and Z, provided that only one of Y and Z may be O or S, that only one of Y and Z may be CH and that only one of X, Y and Z may be NH or N—$C_{1-4}$ alkyl;

$R^1$ is methyl or ethyl;

$R^2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy;

$R^3$ and $R^4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R^3$ and $R^4$ join with the carbon atom to which they are attached to form a 3 or 4 membered carbocyclic ring optionally containing one O, S or N atom and optionally substituted with halo or $C_{1-4}$ alkyl;

$R^5$ is H, $C_{1-4}$ alkyl or $C_{3-6}$ cycloalkyl in which the alkyl or cycloalkyl group is optionally substituted with halo, hydroxy, $C_{1-6}$ alkoxy, cyano, $C_{1-4}$ alkylcarbonyloxy, aminocarbonyloxy or mono- or di($C_{1-4}$)alkylaminocarbonyloxy, tri($C_{1-4}$)-alkylsilyloxy, optionally substituted phenoxy, optionally substituted thienyloxy, optionally substituted benzyloxy or optionally substituted thienylmethoxy, or $R^5$ is optionally substituted phenyl, optionally substituted thienyl or optionally substituted benzyl, in which the optionally substituted phenyl and thienyl rings of the $R^5$ values are optionally substituted with one, two or three substituents selected from halo, hydroxy, mercapto, $C_{1-4}$ alkyl, $C_{2-4}$ alkenyl, $C_{2-4}$ alkyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, halo($C_{1-4}$)alkylthio, hydroxy($C_{1-4}$)alkyl, $C_{1-4}$alkoxy($C_{1-4}$)alkyl, $C_{3-6}$ cycloalkyl, $C_{3-6}$ cycloalkyl($C_{1-4}$) alkyl, phenoxy, benzyloxy, benzoyloxy, cyano, isocyano, thiocyanato, isothiocyanato, nitro, —NR$^p$R$^q$, —NHCOR$^p$, —NHCONR$^p$R$^q$, —CONR$^p$R$^q$, —SO$_2$R$^p$, —OSO$_2$R$^p$, —COR$^p$, —CR$^p$═NR$^q$ or —N═CR$^p$R$^q$, in which R$^p$ and R$^q$ are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; and n is 0, 1 or 2.

When Ar is a group of formula (A), typically $A^1$, $A^2$ and $A^3$ are all chloro or methyl, or $A^1$ and $A^3$ are both chloro, bromo or fluoro and $A^2$ is H or methyl, or $A^1$ and $A^3$ are both methyl or methoxy and $A^2$ is H, chloro, bromo or alkylthio, or $A^1$ is methoxy, $A^2$ is H and $A^3$ is cyano or chloro, or $A^1$ is methyl, $A^2$ is H and $A^3$ is ethyl, or $A^1$ is chloro, bromo, trifluoromethyl, trifluoromethoxy or acetyl and both $A^2$ and $A^3$ are H, or both $A^1$ and $A^3$ are H and $A^2$ is chloro or bromo, or $A^1$ is methyl, $A^2$ is alkylthio and $A^3$ is H.

Of special interest are, when Ar is a group of formula (A), the cases where $A^1$, $A^2$ and $A^3$ are all chloro or methyl, or $A^1$ and $A^3$ are both chloro or bromo and $A^2$ is H or methyl, or $A^1$ and $A^3$ are both methyl or methoxy and $A^2$ is H, chloro, bromo or alkylthio, or $A^1$ is methoxy, $A^2$ is H and $A^3$ is cyano or chloro, or $A^1$ is methyl, $A^2$ is H and $A^3$ is ethyl, or $A^1$ is chloro, bromo or trifluoromethyl and both $A^2$ and $A^3$ are H.

Of particular interest when Ar is a group of the formula (B1) or (B2) are the compounds where, M is N and L is CQ (quinolines) and those compounds where L and M are both N (quinazolines). Also of interest are those compounds where L is N and M is CQ (isoquinolines) and those compounds where L and M are both CQ (naphthyls). Q is typically H or halo, for example, bromo.

Of special interest when Ar is a group of the formula (B) are the compounds where, M is N and L is CQ (quinolines) and those compounds where L and M are both N quinazolines). Also of interest are those compounds where L is N and M is CQ isoquinolines). Q is typically H or halo, for example, bromo.

When Ar is a pyridine group of the formula (C) the alkanoic acid amide side chain in the compound of general formula (1) may be attached to the pyridine ring at the 2-, 3- or 4-position. Preferably it is attached to the 3- or 4-position and more preferably to the 3-position. Typically, in the group of formula (C), $A^4$ is H and $A^5$ is halo, $C_{1-4}$ alkyl, cyclopropyl, $C_{2-4}$ alkenyl, $C_{2-4}$ alkynyl, $C_{1-4}$ alkoxy, $C_{1-4}$ alkylthio, nitro, amino, mono- or di-($C_{1-4}$)alkylamino, formylamino, $C_{1-4}$ alkyl(formyl)amino, $C_{1-4}$ alkylcarbonylamino, $C_{1-4}$ alkyl ($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$) alkylaminocarbonyl, carboxy, $C_{1-4}$ alkylcarbonyloxy, phenyl ($C_{1-4}$)alkylcarbonyloxy, $C_{1-4}$ alkylsulphinyl, $C_{1-4}$ alkylsulphonyl, $C_{1-4}$ alkyl-sulphonyloxy, phenyl, heteroaryl, phenoxy, phenylthio, heteroaryloxy or heteroarylthio wherein any of the foregoing alkyl, cycloalkyl, alkenyl or alkynyl groups or moieties are optionally substituted with halo, hydroxy or $C_{1-4}$ alkoxy and any of the foregoing phenyl or heteroaryl groups or moieties are optionally substituted with halo, $C_{1-4}$ alkyl, $C_{1-4}$ alkoxy, nitro or cyano and heteroaryl is furyl, thienyl, pyridyl or pyrimidinyl. An example of $C_{1-4}$ alkylcarbonylamino is methylcarbonylamino and an example of substituted $C_{1-4}$ alkylsulphonyloxy is trifluoromethylsulphonyloxy.

Of particular interest when Ar is a group of the formula (D1) or (D2) are the groups, linked in the position as shown, of the formula:

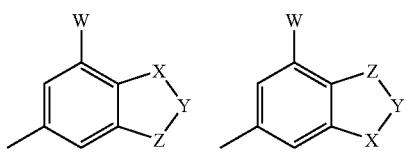

in which W is H, halo, $C_{1-4}$ alkyl, $C_{1-4}$ alkoxy, $C_{1-4}$ alkylthio, $C_{1-4}$ alkylsulphinyl, $C_{1-4}$ alkylsulphonyl, halo($C_{1-4}$)alkyl, halo($C_{1-4}$)alkoxy, halo($C_{1-4}$)alkylthio, halo($C_{1-4}$)alkyl-sulphinyl, halo($C_{1-4}$)alkylsulphonyl, cyano or nitro, and (1) X is N, Y is CR, Z is O, S, NH or N—$C_{1-4}$ alkyl, and R is H, halo, $C_{1-4}$ alkyl, $C_{1-4}$ alkoxy, $C_{1-4}$ alkylthio, $C_{1-4}$ alkylsulphinyl, $C_{1-4}$ alkylsulphonyl, halo($C_{1-4}$)alkyl or halo-($C_{1-4}$)alkoxy, halo($C_{1-4}$)alkylthio, halo($C_{1-4}$)alkylsulphinyl, halo($C_{1-4}$)alkylsulphonyl or mono- or di-($C_{1-4}$) alkylamino, the X—Y bond being a double bond while the Y—Z bond and the bonds joining X and Z td the benzene ring are single bonds; or (2) X and Y are N and Z is O, S, NH or N—$C_{1-4}$ alkyl, the X—Y bond being a double bond while the Y—Z bond and the bonds joining X and Z to the benzene ring are single bonds; or (3) X is N, Y is O, S, NH or N—$C_{1-4}$ alkyl, Z is CR, and R is H, halo, $C_{1-4}$ alkyl, $C_{1-4}$ alkoxy, $C_{1-4}$ alkylthio, $C_{1-4}$ alkylsulphinyl, $C_{1-4}$ alkylsulphonyl, halo($C_{1-4}$)alkyl or halo-($C_{1-4}$)alkoxy, halo($C_{1-4}$)alkylthio, halo($C_{1-4}$)alkylsulphinyl, halo($C_{1-4}$)alkylsulphonyl or mono- or di-($C_{1-4}$) alkylamino, the X—Y and Y—Z bonds being single bonds while the bonds joining X and Z to the benzene ring are double bonds; or (4) X is NH or N—$C_{1-4}$-alkyl, Y is N, Z is CR, and R is H, halo, $C_{1-4}$ alkyl, $C_{1-4}$ alkoxy, $C_{1-4}$ alkylthio, $C_{1-4}$ alkylsulphinyl, $C_{1-4}$ alkylsulphonyl, halo($C_{1-4}$)alkyl or halo($C_{1-4}$)-alkoxy, halo($C_{1-4}$)alkylthio, halo($C_{1-4}$)alkylsulphinyl, halo($C_{1-4}$)alkylsulphonyl or mono- or di-($C_{1-4}$) alkylamino, the Y—Z bond being a double bond while the Y—Z bond and the bonds joining X and Z to the benzene ring are single bonds.

Of special interest where Ar is a group of formula (D1) is the group, linked in the position shown, of the formula:

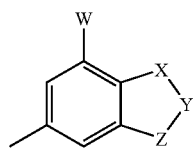

wherein W is H, halo, $C_{1-4}$ alkyl, $C_{1-4}$ alkoxy, halo($C_{1-4}$)alkyl or halo($C_{1-4}$)alkoxy; and (1) X is N, Y is CH, Z is O, S, NH or N—$C_{1-4}$ alkyl, the X—Y bond being a double bond while the Y—Z bond and the bonds joining X and Z to the benzene ring are single bonds; or (2) X and Y are N, Z is O, S, NH or N—$C_{1-4}$ alkyl, the X—Y bond being a double bond while the Y—Z bond and the bonds joining X and Z to the benzene ring are single bonds; or (3) X is N, Y is O, S or NH and Z is CH, the X—Y and Y—Z bonds being single bonds while the bonds joining X and Z to the benzene ring are double bonds; or (4) X is NH, N—$C_{1-4}$ alkyl, Y is N, Z is CH, the Y—Z bond being a double bond while the Y—Z bond and the bonds joining X and Z to the benzene ring are single bonds.

Examples of the group of the formula (D1) and (D2) are 5- and 6-benzothiazolyl optionally bearing a 2-C substituent, 5- and 6-(2,1-benzisothiazolyl) optionally bearing a 3-C substituent, 5- and 6-benzoxazolyl optionally bearing a 2-C substituent, 5- and 6-(2,1-benzisoxazolyl) optionally bearing a 3-C substituent, 5- and 6-(1H-benzimidazolyl) optionally bearing a 2-C substituent and optionally bearing a N—$C_{1-4}$ alkyl substituent, 5- and 6-(1H-indazolyl) optionally bearing a 3-C substituent and optionally bearing a N—$C_{1-4}$ alkyl substituent, 5- and 6-(2H-indazolyl) optionally bearing a 3-C substituent and optionally bearing a N—$C_{1-4}$ alkyl substituent, 5- and 6-(1,2,3-benzothiadiazolyl), 5- and 6-(1,2,3-benzoxadiazolyl), 5- and 6-(1H-benzotriazolyl) optionally bearing a N—$C_{1-4}$ alkyl substituent, 5-(2H-benzotriazolyl) optionally bearing a N—$C_{1-4}$ alkyl substituent, 5-(2,1,3-benzothiadiazolyl) and 5-(2,1,3-benzoxadiazolyl), wherein any of the foregoing optional substitutents are selected from halo, $C_{1-4}$ alkyl, $C_{1-4}$ alkoxy, $C_{1-4}$ alkylthio, $C_{1-4}$ alkyl-sulphinyl, $C_{1-14}$ alkylsulphonyl, halo($C_{1-4}$)alkyl or halo($C_{1-4}$)alkoxy, halo($C_{1-4}$)alkylthio, halo($C_{1-4}$)alkylsulphinyl, halo($C_{1-4}$)alkylsulphonyl or mono- or di-($C_{1-4}$) alkylamino.

Of particular interest are compounds when Ar is a group of the formula (D1) wherein (D1) is selected from the group consisting of 5- and 6-benzothiazolyl, 5- and 6-(2,1-benzisothiazolyl), 5- and 6-benzoxazolyl, 5- and 6-(2,1-benzisoxazolyl), 5- and 6-(1H-benzimidazolyl) optionally bearing a N—$C_{1-4}$ alkyl substituent, 5- and 6-(1H-indazolyl) optionally bearing a N—$C_{1-4}$ alkyl substituent, 5- and 6-(2H-indazolyl), 5- and 6-(1,2,3-benzothiadiazolyl), 5- and 6-(1,2,3-benzoxadiazolyl), 5- and 6-(1H-benzo-triazolyl) optionally bearing a N—$C_{1-4}$ alkyl substituent, 5-(2H-benzotriazolyl), 5-(2,1,3-benzothiadiazolyl) and 5-(2,1,3-benzoxadiazolyl).

Of more particular interest when Ar is a group of the formula (D1) or (D2) are compounds in which the group of the formula (D1) or (D2) is 5- or 6-benzothiazolyl optionally bearing a 2-C substituent, 5-(2,1-benzisothiazolyl) optionally bearing a 3-C substituent, 6-benzoxazolyl optionally bearing a 2-C substituent, 5-(2,1-benzisoxazolyl) optionally bearing a 3-C substituent, 6-(1H-benzimidazolyl) optionally bearing a 2-C substituent and optionally bearing a N—$C_{1-4}$ alkyl substituent, 5-(1H-indazolyl) optionally bearing a 3-C substituent and optionally bearing a N—$C_{1-4}$ alkyl substituent, 6-(1,2,3-benzothiadiazolyl) or 6-(1,2,3-benzoxadiazolyl), wherein any of the foregoing optional substituents are selected from halo, $C_{1-4}$ alkyl, $C_{1-4}$ alkoxy, $C_{1-4}$ alkylthio, $C_{1-4}$ alkyl-sulphinyl, $C_{1-4}$ alkylsulphonyl, halo($C_{1-4}$)alkyl or halo($C_{1-4}$)alkoxy, halo($C_{1-4}$)alkylthio, halo($C_{1-4}$)alkylsulphinyl, halo($C_{1-4}$)alkylsulphonyl or mono- or di-($C_{1-4}$) alkylamino.

Of even further interest when Ar is a group of the formula (D1) are compounds wherein (D1) is 5- or 6-benzothiazolyl, 5-(2,1-benzisothiazolyl), 6-benzoxazolyl, 5-(2,1-benzisoxazolyl), 6-(1H-benzimidazolyl) optionally bearing a N—$C_{1-4}$ alkyl substituent, 5-(1H-indazolyl) optionally bearing a N—$C_{1-4}$ alkyl substituent, 6-(1,2,3-benzothiadiazolyl) or 6-(1,2,3-benzoxadiazolyl).

Of special interest are compounds in which the group of the formula (D1) or (D2) is 6-benzoxazolyl optionally bearing a 2-C substituent or 6-benzothiazolyl optionally bearing a 2-C substituent, particularly the latter, wherein any of the foregoing optional substitutents is selected from halo, $C_{1-4}$ alkyl, $C_{1-4}$ alkoxy, $C_{1-4}$ alkylthio, $C_{1-4}$ alkyl-sulphinyl, $C_{1-4}$ alkylsulphonyl, halo($C_{1-4}$)alkyl or halo($C_{1-4}$)alkoxy, halo($C_{1-4}$)alkylthio, halo($C_{1-4}$)alkylsulphinyl, halo($C_{1-4}$)alkylsulphonyl or mono- or di-($C_{1-4}$) alkylamino.

Of even further interest are compounds in which the group of the formula (D1) is 6-benzoxazolyl or 6-benzothiazolyl, particularly the latter.

$R^1$ is methyl or ethyl.

Typically $R^2$ is H and at least one, but preferably both of $R^3$ and $R^4$ are methyl. When one of $R^3$ and $R^4$ is H, the other may be methyl, ethyl or n- or iso-propyl. When one of $R^3$ and $R^4$ is methyl, the other may be H or ethyl but is preferably also methyl. $R^2$ also includes $C_{1-4}$ alkoxymethyl and benzyloxymethyl in which the phenyl ring of the benzyl group optionally carries an alkoxy substituent, e.g. a methoxy substituent. Such values of $R^2$ provide compounds of formula (1) that are believed to be pro-pesticidal compounds.

Typically $R^5$ is H or methyl, preferably methyl. However, also of particular interest are compounds where $R^5$ is hydroxymethyl, methoxymethyl, 1-methoxyethyl, 3-cyano-n-propyl, 3-chloro-n-propyl, phenyl, p-fluoro-phenyl, m-acetyl-phenyl, 2-thienyl, 3-thienyl and tert-butyldimethylsilyloxymethyl, especially where $R^5$ is hydroxymethyl, methoxymethyl, 1-methoxyethyl, 3-cyano-n-propyl and tert-butyldimethylsilyloxymethyl.

In one aspect the invention provides a compound of the general formula (1) wherein Ar is as hereinbefore defined; $R^1$ is methyl or ethyl; $R^2$ is H; $R^3$ and $R^4$ are both methyl; $R^5$ is H, methyl, hydroxymethyl, methoxymethyl, 1-methoxyethyl, 3-cyano-n-propyl, 3-chloro-n-propyl, phenyl, p-fluoro-phenyl, m-acetyl-phenyl, 2-thienyl, 3-thienyl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl; and n is 0, 1 or 2, typically 0. Preferably $R^5$ is methyl or methoxymethyl.

In another aspect the invention provides a compound of the general formula (1) wherein Ar is a group of the formula (A) wherein $A^1$, $A^2$ and $A^3$ are all chloro or methyl, or $A^1$ and $A^3$ are both chloro, bromo or fluoro and $A^2$ is H or methyl, or $A^1$ and $A^3$ are both methyl or methoxy and $A^2$ is H, chloro, bromo or alkylthio, or $A^1$ is methoxy, $A^2$ is H and $A^3$ is cyano or chloro, or $A^1$ is methyl, $A^2$ is H and $A^3$ is ethyl, or $A^1$ is chloro, bromo, trifluoromethyl, trifluoromethoxy or acetyl and both $A^2$ and $A^3$ are H, or both $A^1$ and $A^3$ are H and $A^2$ is chloro or bromo, or $A^1$ is methyl, $A^2$ is alkylthio and $A^3$ is H; $R^1$ is methyl or ethyl; $R^2$ is H; $R^3$ and $R^4$ are both methyl; $R^5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl; and n is 0, 1 or 2, typically 0. Preferably $R^5$ is methyl or methoxymethyl.

In yet another aspect the invention provides a compound of the general formula (1) wherein Ar is a group of the formula (A) wherein $A^1$, $A^2$ and $A^3$ are all chloro or methyl, or $A^1$ and $A^3$ are both chloro or bromo, particularly chloro, and $A^2$ is H or methyl, or $A^1$ and $A^3$ are both methyl or methoxy and $A^2$ is H, chloro, bromo or alkylthio, or $A^1$ is methoxy, $A^2$ is H and $A^3$ is cyano or chloro, or $A^1$ is methyl, $A^2$ is H and $A^3$ is ethyl, or $A^1$ is chloro, bromo or trifluormrethyl and both $A^2$ and $A^3$ are H; $R^1$ is methyl or ethyl; $R^2$ is H; $R^3$ and $R^4$ are both methyl; $R^5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl; and n is 0, 1 or 2, typically 0. Preferably $R^5$ is methyl or methoxymethyl.

In a further aspect the invention provides a compound of the general formula (1) wherein Ar is a group of the formula (B1) or (B2) wherein L and M are independently N, N-oxide or CQ, except that no more than one of L or M is N-oxide; Q is hydrogen or halo (for example bromo); $R_1$ is methyl or ethyl; $R_2$ is H; $R_3$ and $R_4$ are both methyl; $R_5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl; and n is 0, 1 or 2, typically 0. Preferably $R_5$ is methyl or methoxymethyl.

In yet another aspect the invention provides a compound of the general formula (1) wherein Ar is a group of the formula (B) wherein one of L and M is N and the other is CQ, or both of L and M are N; Q is hydrogen or halo (for example bromo); $R_1$ is methyl or ethyl; $R_2$ is H; $R_3$ and $R_4$ are both methyl; $R_5$ is H, methyl, hydroxymethyl, methoxymethyl, 1-methoxyethyl, 3-cyano-n-propyl, 3-chloro-yl-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl; and n is 0, 1 or 2, typically 0. Preferably $R_5$ is methyl or methoxymethyl.

In a further aspect, the invention provides a compound of the general formula (I) wherein Ar is a group of the formula (C) wherein $A^4$ is H; and $A^5$ is halo, $C_{1-4}$ alkyl, cyclopropyl, $C_{2-4}$ alkenyl, $C_{2-4}$ alkynyl, $C_{1-4}$ alkoxy, $C_{1-4}$ alkylthio, nitro, amino, mono- or di-($C_{1-4}$)alkylamino, formylamino, $C_{1-4}$ alkyl(formyl)amino, $C_{1-4}$ alkylcarbonylamino, $C_{1-4}$ alkyl ($C_{1-4}$ alkylcarbonyl)amino, cyano, formyl, $C_{1-4}$ alkylcarbonyl, $C_{1-4}$ alkoxycarbonyl, aminocarbonyl, mono- or di-($C_{1-4}$) alkylaminocarbonyl, carboxy, $C_{1-4}$ alkylcarbonyloxy, phenyl ($C_{1-4}$)alkylcarbonyloxy, $C_{1-4}$ alkylsulphinyl, $C_{1-4}$ alkylsulphonyl, $C_{1-4}$ alkyl-sulphonyloxy, phenyl, heteroaryl, phenoxy, phenylthio, heteroaryloxy or heteroarylthio, wherein any of the foregoing alkyl, cycloalkyl, alkenyl or alkynyl groups or moieties, which $A^5$ may be, are optionally substituted with halo, hydroxy or $C_{1-4}$ alkoxy; any of the foregoing phenyl or heteroaryl groups or moieties, which $A^5$ may be, are optionally substituted with halo, $C_{1-4}$ alkyl, $C_{1-4}$ alkoxy, nitro or cyano; heteroaryl is furyl, thienyl, pyridyl or pyrimidinyl; $R^1$ is methyl or ethyl; $R^2$ is H; $R^3$ and $R^4$ are both methyl; $R_5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl; and n is 0, 1 or 2, typically 0. Preferably $R_5$ is methyl or methoxymethyl. A further preference is that the alkanoic acid amide side chain is attached to the pyridine ring of the group of formula (C) at the 3-position.

In yet another aspect the invention provides a compound of general formula (1) wherein Ar is a group of the formula (C) wherein $A^4$ is H, $C_{1-4}$ alkyl, halo($C_{1-4}$)alkyl or CN; $A^5$ is H, halo, $C_{1-4}$ alkyl or halo($C_{1-4}$)alkyl; $R^1$ is methyl or ethyl; $R^2$ is H; $R^3$ and $R^4$ are both methyl; $R_5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl, preferably methyl or methoxymethyl; n is 0, 1 or 2, typically 0; and the alkanoic acid amide side chain is attached to the 3-position of the pyridine ring.

In yet another aspect the invention provides a compound of general formula (1) wherein Ar is a group of the formula (C) wherein $A^4$ is H, $C_{1-4}$ alkyl, halo($C_{1-4}$)alkyl or CN; $A^5$ is H, halo, $C_{1-4}$ alkyl or halo($C_{1-4}$)alkyl; $R^1$ is methyl or ethyl; $R^2$ is H; $R^3$ and $R^4$ are both methyl; $R^5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl, preferably methyl or methoxymethyl; n is 0, 1 or 2, typically 0; and the alkanoic acid amide side chain is attached to the 4-position of the pyridine ring.

In still yet another aspect the invention provides a compound of the general formula (1) wherein Ar is 5- or 6-benzothiazolyl optionally bearing a 2-C substituent, 5-(2,1-benzisothiazolyl) optionally bearing a 3-C substituent, 6-benzoxazolyl optionally bearing a 2-C substituent, 5-(2,1-benzisoxazolyl) optionally bearing a 3-C substituent, 6-(1H-benzimidazolyl) optionally bearing a 2-C substituent and optionally bearing a N—$C_{1-4}$ alkyl substituent, 5-(1H-indazolyl) optionally bearing a 3-C substitutent and optionally bearing a N—$C_{1-4}$ alkyl substituent, 6-(1,2,3-benzothiadiazolyl) or 6-(1,2,3-benzoxadiazolyl), wherein any of the foregoing optional substituents are selected from halo, $C_{1-4}$ alkyl, $C_{1-4}$ alkoxy, $C_{1-4}$ alkylthio, $C_{1-4}$ alkylsulphinyl, $C_{1-4}$ alkylsulphonyl, halo($C_{1-4}$)alkyl or halo($C_{1-4}$)alkoxy, halo($C_{1-4}$)alkylthio, halo($C_{1-4}$)alkylsulphinyl, halo($C_{1-4}$)alkyl-sulphonyl or mono- or di-($C_{1-4}$) alkylamino; $R_1$ is methyl or ethyl, $R_2$ is H; $R_3$ and $R_4$ are both methyl; and $R_5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl. Preferably $R_5$ is methyl or methoxymethyl.

In yet another aspect the invention provides a compound of the general formula (1) wherein Ar is 5- or 6-benzothiazolyl, 5-(2,1-benzisothiazolyl), 6-benzoxazolyl, 5-(2,1-benzisoxazolyl), 6-(1H-benzimidazolyl) optionally bearing a N—$C_{1-4}$ alkyl substituent, 5-(1H-indazolyl) optionally bearing a N—$C_{1-4}$ alkyl substituent, 6-(1,2,3-benzothiadiazolyl) or 6-(1,2,3-benzoxadiazolyl); $R_1$ is methyl or ethyl, $R_2$ is H; $R_3$ and $R_4$ are both methyl; and $R_5$ is H, methyl, hydroxymethyl, methoxymethyl, 1-methoxyethyl, 3-cyano-n-propyl, 3-chloro-n-propyl, phenyl, 4-fluoro-phenyl, 3-acetyl-phenyl, thien-2-yl, thien-3-yl and tert-butyldimethylsilyloxymethyl, especially where $R^5$ is H, methyl, hydroxymethyl, methoxymethyl, 1-methoxyethyl, 3-cyano-n-propyl and tert-butyldimethylsilyloxymethyl. Preferably $R_5$ is methyl or methoxymethyl.

Compounds that form part of the invention are illustrated in Tables 1 to 129 below. Characterising data is given in Table 130 after the Examples.

TABLE 1

The compounds in Table 1 are of the general formula (1) where Ar is a group of the formula (A), n is 0, $R^1$ is methyl, $R^2$ is H, $R^3$ and $R^4$ are both methyl, $R^5$ is methyl and $A^1$, $A^2$ and $A^3$ have the values given in the table.

| Compound No | $A^1$ | $A^2$ | $A^3$ |
|---|---|---|---|
| 1 | Cl | Cl | CN |
| 2 | Cl | Cl | Cl |
| 3 | $CH_3$ | $CH_3$ | $CH_3$ |
| 4 | Cl | H | Cl |
| 5 | Cl | $CH_3$ | Cl |
| 6 | Br | H | Br |
| 7 | Br | $CH_3$ | Br |
| 8 | $CH_3$ | H | $CH_3$ |
| 9 | $CH_3$ | Cl | $CH_3$ |
| 10 | $CH_3$ | Br | $CH_3$ |
| 11 | $CH_3$ | $CH_3S$ | $CH_3$ |
| 12 | $CH_3O$ | H | $CH_3O$ |
| 13 | $CH_3O$ | Cl | $CH_3O$ |
| 14 | $CH_3O$ | Br | $CH_3O$ |
| 15 | $CH_3O$ | $CH_3S$ | $CH_3O$ |
| 16 | $CH_3O$ | H | CN |
| 17 | $CH_3O$ | H | Cl |
| 18 | $CH_3$ | H | $C_2H_5$ |
| 19 | Cl | H | H |
| 20 | Br | H | H |
| 21 | $CF_3$ | H | H |
| 22 | H | Cl | H |
| 23 | H | Br | H |
| 24 | H | F | H |
| 25 | H | CN | H |
| 26 | H | $CF_3O$ | H |
| 27 | H | $CH_3S$ | H |
| 28 | H | HC≡C— | H |
| 29 | H | $CH_2$=CH— | H |
| 30 | H | $CH_3O$ | H |
| 31 | H | $COCH_3$ | H |
| 32 | H | $CF_3$ | H |
| 33 | F | H | H |
| 34 | CN | H | H |
| 35 | $CH_3$ | H | H |
| 36 | $CH_3CO$ | H | H |
| 37 | $CH_3O$ | H | H |
| 38 | $CF_3O$ | H | H |
| 39 | $CH_3S$ | H | H |
| 40 | HC≡C— | H | H |
| 41 | $H_2C$=CH— | H | H |
| 42 | F | H | F |
| 43 | F | H | Cl |
| 44 | F | H | Br |
| 45 | F | H | $CH_3O$ |
| 46 | F | H | $CH_3CO$ |
| 47 | F | H | CN |
| 48 | F | H | $CH_3$ |
| 49 | F | H | $CF_3O$ |
| 50 | F | H | $CF_3$ |
| 51 | F | H | $CH_3S$ |
| 52 | F | H | $COOCH_3$ |
| 53 | Cl | H | Br |
| 54 | Cl | H | $CH_3CO$ |
| 55 | Cl | H | $CH_3$ |
| 56 | Cl | H | CN |
| 57 | Cl | H | $CF_3O$ |
| 58 | Cl | H | $CF_3$ |
| 59 | Cl | H | $CH_3S$ |
| 60 | Cl | H | $COOCH_3$ |
| 61 | Cl | H | $CON(CH_3)_2$ |
| 62 | Cl | H | $NHCOOCH_3$ |
| 63 | Cl | H | $OSO_2CH_3$ |
| 64 | Cl | H | HC≡C— |
| 65 | Cl | H | $CH_2$=CH— |
| 66 | Br | H | $CH_3$ |
| 67 | Br | H | CN |
| 68 | CN | H | CN |
| 69 | CN | H | $CH_3$ |
| 70 | CN | H | $CF_3O$ |
| 71 | $CF_3O$ | H | $CF_3O$ |
| 72 | $CF_3$ | H | $CF_3$ |
| 73 | $CH_3$ | H | $CH_3O$ |
| 74 | F | F | H |
| 75 | F | Cl | H |
| 76 | F | Br | H |
| 77 | F | $CH_3O$ | H |
| 78 | F | CN | H |
| 79 | F | $CH_3$ | H |
| 80 | Cl | Cl | H |
| 81 | Cl | F | H |
| 82 | Cl | Br | H |
| 83 | Cl | CN | H |
| 84 | Cl | $CH_3$ | H |
| 85 | Cl | $CH_3O$ | H |

TABLE 1-continued

The compounds in Table 1 are of the general formula (1) where Ar is a group of the formula (A), n is 0, $R^1$ is methyl, $R^2$ is H, $R^3$ and $R^4$ are both methyl, $R^5$ is methyl and $A^1$, $A^2$ and $A^3$ have the values given in the table.

| Compound No | $A^1$ | $A^2$ | $A^3$ |
|---|---|---|---|
| 86 | Cl | $CF_3O$ | H |
| 87 | Cl | $CH_3S$ | H |
| 88 | Cl | $CH_3SO_2O$ | H |
| 89 | Cl | $CH_3CO$ | H |
| 90 | CN | F | H |
| 91 | CN | Cl | H |
| 92 | CN | $CH_3O$ | H |
| 93 | $CH_3O$ | $CH_3O$ | H |
| 94 | $CH_3O$ | Cl | H |
| 95 | $CH_3O$ | CN | H |
| 96 | $CH_3CO$ | Cl | H |
| 97 | $CF_3O$ | Cl | H |
| 98 | $CF_3O$ | CN | H |
| 99 | $CH_3S$ | Cl | H |
| 100 | $CH_3S$ | F | H |
| 101 | $CH_3S$ | $CH_3$ | H |
| 102 | $CH_3SO_2O$ | Cl | H |
| 103 | Cl | Cl | F |
| 104 | Cl | Cl | Br |
| 105 | Cl | Cl | $CH_3O$ |
| 106 | Cl | Cl | $CH_3CO$ |
| 107 | Cl | Cl | $CH_3S$ |
| 108 | Cl | F | Cl |
| 109 | Cl | $CH_3O$ | Cl |
| 110 | Cl | $CF_3O$ | Cl |
| 111 | Cl | $CH_3SO$ | Cl |
| 112 | Cl | $CH_3SO_2$ | Cl |
| 113 | Cl | $OSO_2CH_3$ | Cl |
| 114 | Cl | $CH_3CO$ | Cl |
| 115 | Cl | $CO_2CH_3$ | Cl |
| 116 | Cl | $CON(CH_3)_2$ | Cl |
| 117 | Cl | HC≡C— | Cl |
| 118 | Cl | $CH_2$=CH— | Cl |
| 119 | Cl | $NHCO_2CH_3$ | Cl |
| 120 | F | F | F |
| 121 | F | F | CN |
| 122 | F | F | $CH_3$ |
| 123 | F | F | $CH_3O$ |
| 124 | F | $CH_3O$ | F |
| 125 | F | $CF_3O$ | F |
| 126 | F | $CH_3SO$ | F |
| 127 | F | $CH_3SO_2$ | F |
| 128 | F | $OSO_2CH_3$ | F |
| 129 | F | $CH_3CO$ | F |
| 130 | F | $CO_2CH_3$ | F |
| 131 | $CH_3O$ | $CH_3O$ | $CH_3O$ |
| 132 | $CH_3O$ | $CH_3O$ | Cl |
| 133 | $CH_3O$ | $CH_3O$ | $CH_3$ |
| 134 | Cl | CN | Cl |
| 135 | $CH_3$ | $CH_3S$ | H |
| 136 | $C_6H_5O$ | H | H |

Table 2

Table 2 consists of 136 compounds of the general formula (1), where Ar is a group of the formula (A), n is 0, $R^1$ is ethyl, $R^2$ is hydrogen, $R^3$ and $R^4$ are both methyl, $R^5$ is methyl and $A^1$, $A^2$ and $A^3$ have the values listed in Table 1. Thus compound 1 of Table 2 is the same as compound 1 of Table 1 except that in compound 1 of Table 2 $R^1$ is ethyl instead of methyl. Similarly, compounds 2 to 136 of Table 2 are the same as compounds 2 to 136 of Table 1, respectively, except that in the compounds of Table 2 $R^1$ is ethyl instead of methyl.

Table 3

Table 3 consists of 136 compounds of the general formula (1), where Ar is a group of the formula (A), n is 0, $R^1$ is methyl, $R^2$ is hydrogen, $R^3$ and $R^4$ are both methyl, $R^5$ is H and $A^1$, $A^2$ and $A^3$ have the values listed in Table 1. Thus compound 1 of Table 3 is the same as compound 1 of Table 1 except that in compound 1 of Table 3 $R^5$ is H instead of methyl. Similarly, compounds 2 to 136 of Table 3 are the same as compounds 2 to 136 of Table 1, respectively, except that in the compounds of Table 3 $R^5$ is H instead of methyl.

Table 4

Table 4 consists of 136 compounds of the general formula (1), where Ar is a group of the formula (A), n is 0, $R^1$ is ethyl, $R^2$ is hydrogen, $R^3$ and $R^4$ are both methyl, $R^5$ is H and $A^1$, $A^2$ and $A^3$ have the values listed in Table 1. Thus compound 1 of Table 4 is the same as compound 1 of Table 2 except that in compound 1 of Table 4 $R^5$ is H instead of methyl. Similarly, compounds 2 to 136 of Table 4 are the same as compounds 2 to 136 of Table 2, respectively, except that in the compounds of Table 4 $R^5$ is H instead of methyl.

Table 5

Table 9 consists of 136 compounds of the general formula (1), where Ar is a group of the formula (A), n is 0, $R^1$ is methyl, $R^2$ is hydrogen, $R^3$ and $R^4$ are both methyl, $R^5$ is hydroxymethyl and $A^1$, $A^2$ and $A^3$ have the values listed in Table 1. Thus compound 1 of Table 5 is the same as compound 1 of Table 1 except that in compound 1 of Table 5 $R^5$ is hydroxymethyl instead of methyl. Similarly, compounds 2 to 136 of Table 5 are the same as compounds 2 to 136 of Table 1, respectively, except that in the compounds of Table 5 $R^5$ is hydroxymethyl instead of methyl.

Table 6

Table 6 consists of 136 compounds of the general formula (1), where Ar is a group of the formula (A), n is 0, $R^1$ is ethyl, $R^2$ is hydrogen, $R^3$ and $R^4$ are both methyl, $R^5$ is hydroxymethyl and $A^1$, $A^2$ and $A^3$ have the values listed in Table 1. Thus compound 1 of Table 6 is the same as compound 1 of Table 2 except that in compound 1 of Table 6 $R^5$ is hydroxymethyl instead of methyl. Similarly, compounds 2 to 136 of Table 6 are the same as compounds 2 to 136 of Table 2, respectively, except that in the compounds of Table 6 $R^5$ is hydroxymethyl instead of methyl.

Table 7

Table 7 consists of 136 compounds of the general formula (1), where Ar is a group of the formula (A), n is 0, $R^1$ is methyl, $R^2$ is hydrogen, $R^3$ and $R^4$ are both methyl, $R^5$ is methoxymethyl and $A^1$, $A^2$ and $A^3$ have the values listed in Table 1. Thus compound 1 of Table 7 is the same as compound 1 of Table 1 except that in compound 1 of Table 7 $R^5$ is methoxymethyl instead of methyl. Similarly, compounds 2 to 136 of Table 7 are the same as compounds 2 to 136 of Table 1, respectively, except that in the compounds of Table 7 $R^5$ is methoxymethyl instead of methyl.

Table 8

Table 8 consists of 136 compounds of the general formula (1), where Ar is a group of the formula (A), n is 0, $R^1$ is ethyl, $R^2$ is hydrogen, $R^3$ and $R^4$ are both methyl, $R^5$ is methoxymethyl and $A^1$, $A^2$ and $A^3$ have the values listed in Table 1. Thus compound 1 of Table 8 is the same as compound 1 of Table 2 except that in compound 1 of Table 8 $R^5$ is methoxymethyl instead of methyl. Similarly, compounds 2 to 136 of Table 8 are the same as compounds 2 to 136 of Table 2, respectively, except that in the compounds of Table 8 $R^5$ is methoxymethyl instead of methyl.

Table 9

Table 9 consists of 136 compounds of the general formula (1), where Ar is a group of the formula (A), n is 0, $R^1$ is methyl, $R^2$ is hydrogen, $R^3$ and $R^4$ are both methyl, $R^5$ is tert-butyldimethylsilyloxymethyl and $A^1$, $A^2$ and $A^3$ have the values listed in Table 1. Thus compound 1 of Table 9 is the same as compound 1 of Table 1 except that in compound 1 of Table 9 $R^5$ is tert-butyldimethylsilyloxymethyl instead of methyl. Similarly, compounds 2 to 136 of Table 9 are the same as compounds 2 to 136 of Table 1, respectively, except that in the compounds of Table 9 $R^5$ is tert-butyldimethylsilyloxymethyl instead of methyl.

Table 10

Table 10 consists of 136 compounds of the general formula (1), where Ar is a group of the formula (A), n is 0, $R^1$ is ethyl, $R^2$ is hydrogen, $R^3$ and $R^4$ are both methyl, $R^5$ is tert-butyldimethylsilyloxymethyl and $A^1$, $A^2$ and $A^3$ have the values listed in Table 1. Thus compound 1 of Table 10 is the same as compound 1 of Table 2 except that in compound 1 of Table 10 $R^5$ is tert-butyldimethylsilyloxymethyl instead of methyl. Similarly, compounds 2 to 136 of Table 10 are the same as compounds 2 to 136 of Table 2, respectively, except that in the compounds of Table 10 $R^5$ is tert-butyldimethylsilyloxymethyl instead of methyl.

Table 11

Table 11 consists of 136 compounds of the general formula (1), where Ar is a group of the formula (A), n is 0, $R^1$ is methyl, $R^2$ is hydrogen, $R^3$ and $R^4$ are both methyl, $R^5$ is 1-methoxyethyl and $A^1$, $A^2$ and $A^3$ have the values listed in Table 1. Thus compound 1 of Table 11 is the same as compound 1 of Table 1 except that in compound 1 of Table 11 $R^5$ is 1-methoxyethyl instead of methyl. Similarly, compounds 2 to 136 of Table 11 are the same as compounds 2 to 136 of Table 1, respectively, except that in the compounds of Table 11 $R^5$ is 1-methoxyethyl instead of methyl.

Table 12

Table 12 consists of 136 compounds of the general formula (1), where Ar is a group of the formula (A), n is 0, $R^1$ is ethyl, $R^2$ is hydrogen, $R^3$ and $R^4$ are both methyl, $R^5$ is 1-methoxyethyl and $A^1$, $A^2$ and $A^3$ have the values listed in Table 1. Thus compound 1 of Table 12 is the same as compound 1 of Table 2 except that in compound 1 of Table 12 $R^5$ is 1-methoxyethyl instead of methyl. Similarly, compounds 2 to 136 of Table 12 are the same as compounds 2 to 136 of Table 2, respectively, except that in the compounds of Table 12 $R^5$ is 1-methoxyethyl instead of methyl.

Table 13

Table 13 consists of 136 compounds of the general formula (1), where Ar is a group of the formula (A), n is 0, $R^1$ is methyl, $R^2$ is hydrogen, $R^3$ and $R^4$ are both methyl, $R^5$ is 3-cyanopropyl and $A^1$, $A^2$ and $A^3$ have the values listed in Table 1. Thus compound 1 of Table 12 is the same as compound 1 of Table 2 except that in compound 1 of Table 12 $R^5$ is 1-methoxyethyl instead of methyl. Similarly, compounds 2 to 136 of Table 12 are the same as compounds 2 to 136 of Table 2, respectively, except that in the compounds of Table 12 $R^5$ is 1-methoxyethyl instead of methyl.

TABLE 14

The compounds in Table 14 are of the general formula (1) where Ar is a group of the formula (B1), M is N, L is CH, $K^a$, $K^b$ and V are H, n is 0, $R_1$ is methyl, $R_2$ is H, $R_3$ and $R_4$ are both methyl and $R_5$ has the values given in the table.

| Compound No. | $R_5$ |
|---|---|
| 1 | H |
| 2 | $CH_3$ |
| 3 | $C_2H_5$ |
| 4 | n-$C_3H_7$ |
| 5 | i-$C_3H_7$ |
| 6 | n-$C_4H_9$ |
| 7 | sec-$C_4H_9$ |
| 8 | iso-$C_4H_9$ |
| 9 | tert-$C_4H_9$ |
| 10 | $HOCH_2$ |
| 11 | $HOC_2H_4$ |
| 12 | $CH_3OCH_2$ |
| 13 | $CH_3OCH_2CH_2$ |
| 14 | $C_2H_5OCH_2$ |
| 15 | $CH_3(CH_3O)CH$ |
| 16 | n-$C_3H_7OCH_2$ |
| 17 | n-$C_3H_7OC_2H_4$ |
| 18 | t-$C_4H_9OCH_2$ |
| 19 | t-$C_4H_9OC_2H_4$ |
| 20 | NC—$C_2H_4$ |
| 21 | NC-n-$C_3H_6$ |
| 22 | NC-n-$C_4H_8$ |
| 23 | $(CH_3)_2C(CN)CH_2$ |
| 24 | 2-cyano-cycloprop-1-yl |
| 25 | 4-cyano-cyclohex-1-yl |
| 26 | $C_6H_5CH_2$ |
| 27 | $C_6H_5OC_2H_4$ |
| 28 | 4-t-$C_4H_9$—$C_6H_4OCH_2$ |
| 29 | 4-F—$C_6H_4OCH_2$ |
| 30 | 4-Cl—$C_6H_4OCH_2$ |
| 31 | 4-$CH_3$—$C_6H_4OCH_2$ |
| 32 | 4-Br—$C_6H_4OCH_2$ |
| 33 | 2-F—$C_6H_4OCH_2$ |
| 34 | 3,4-$Cl_2$—$C_6H_3OCH_2$ |
| 35 | 3-$CF_3$—$C_6H_4OCH_2$ |
| 36 | 3,5-$Cl_2$—$C_6H_3OCH_2$ |
| 37 | 4-$CF_3O$—$C_6H_5OCH_2$ |
| 38 | 2-$CF_3$—$C_6H_4OCH_2$ |
| 39 | 4-$CF_3$—$C_6H_4OCH_2$ |
| 40 | 2-Br—$C_6H_4OCH_2$ |
| 41 | 2-Cl—$C_6H_4OCH_2$ |
| 42 | 2-$CH_3$-4-Cl—$C_6H_3OCH_2$ |
| 43 | 2-$CH_3$-5-F—$C_6H_3OCH_2$ |
| 44 | 3-Cl—$C_6H_4OCH_2$ |
| 45 | thien-2-yl-$OCH_2$ |
| 46 | thien-3-yl-$OCH_2$ |
| 47 | $C_6H_5CH_2OCH_2$ |
| 48 | thien-2-yl-$CH_2OCH_2$ |
| 49 | thien-3-yl-$CH_2OCH_2$ |
| 50 | tert-$C_4H_9(CH_3)_2SiOCH_2$ |
| 51 | tert-$C_4H_9(CH_3)_2SiOC_2H_4$ |
| 52 | $C_6H_5$ |
| 53 | 4-t-$C_4H_9$—$C_6H_4$ |
| 54 | 4-F—$C_6H_4$ |
| 55 | 4-Cl—$C_6H_4$ |
| 56 | 4-$CH_3$—$C_6H_4$ |
| 57 | 4-Br—$C_6H_4$ |
| 58 | $3CH_3CO$—$C_6H_4$ |
| 59 | 3,4-$Cl_2$—$C_6H_3$ |
| 60 | 3-$CF_3$—$C_6H_4$ |
| 61 | 3,5-$Cl_2$—$C_6H_3$ |
| 62 | 4-$CF_3O$—$C_6H_4$ |
| 63 | 2-$CF_3$—$C_6H_4$ |
| 64 | 4-$CF_3$—$C_6H_4$ |
| 65 | 2-Br—$C_6H_4$ |
| 66 | 2-Cl—$C_6H_4$ |
| 67 | 2-$CH_3$-4-Cl—$C_6H_3$ |
| 68 | 2-$CH_3$-5-F—$C_6H_3$ |
| 69 | 3-Cl—$C_6H_4$ |
| 70 | thien-2-yl |
| 71 | thien-3-yl |
| 72 | $C_6H_5CH_2$ |
| 73 | 4-t-$C_4H_9$—$C_6H_4CH_2$ |
| 74 | 4-F—$C_6H_4CH_2$ |
| 75 | 4-Cl—$C_6H_4CH_2$ |
| 76 | 4-$CH_3$—$C_6H_4CH_2$ |
| 77 | 4-Br—$C_6H_4CH_2$ |
| 78 | 2-F—$C_6H_4CH_2$ |
| 79 | 3,4-$Cl_2$—$C_6H_3CH_2$ |
| 80 | 3-$CF_3$—$C_6H_4CH_2$ |
| 81 | 3,5-$Cl_2$—$C_6H_3CH_2$ |
| 82 | 4-$CF_3O$—$C_6H_5CH_2$ |
| 83 | 2-$CF_3$—$C_6H_4CH_2$ |
| 84 | 4-$CF_3$—$C_6H_4CH_2$ |
| 85 | 2-Br—$C_6H_4CH_2$ |

TABLE 14-continued

The compounds in Table 14 are of the general formula (1) where Ar is a group of the formula (B1), M is N, L is CH, $K^a$, $K^b$ and V are H, n is 0, $R_1$ is methyl, $R_2$ is H, $R_3$ and $R_4$ are both methyl and $R_5$ has the values given in the table.

| Compound No. | $R_5$ |
|---|---|
| 86 | 2-Cl—$C_6H_4CH_2$ |
| 87 | 2-$CH_3$-4-Cl—$C_6H_3CH_2$ |
| 88 | 2-$CH_3$-5-F—$C_6H_3CH_2$ |
| 89 | 3-Cl—$C_6H_4CH_2$ |
| 90 | Cl-n-$C_3H_6$ |

Table 15

Table 15 consists of 90 compounds of the general formula (1), where Ar is a group of the Formula (B1), M is N, L is CH, $K^a$, $K^b$ and V are H, n is 0, $R_1$ is ethyl, $R_2$ is hydrogen, $R_3$ and $R_4$ are both methyl and $R_5$ has the values listed in Table 14. Thus compound 1 of Table 15 is the same as compound 1 of Table 14 except that in compound 1 of Table 15 $R_1$ is ethyl instead of methyl. Similarly, compounds 2 to 90 of Table 15 are the same as compounds 2 to 90 of Table 14, respectively, except that in the compounds of Table 15 $R_1$ is ethyl instead of methyl.

Table 16

Table 16 consists of 90 compounds of the general formula (1), where Ar is a group of the formula (B1), L and M are both N, $K^a$, $K^b$ and V are H, n is 0, $R_1$ is methyl, $R_2$ is hydrogen, $R_3$ and $R_4$ are both methyl and $R_5$ has the values listed in Table 14. Thus compound 1 of Table 16 is the same as compound 1 of Table 14 except that in compound 1 of Table 16 L is N instead of CH. Similarly, compounds 2 to 90 of Table 16 are the same as compounds 2 to 90 of Table 14, respectively, except that in the compounds of Table 16 L is N instead of CH.

Table 17

Table 17 consists of 90 compounds of the general formula (1), where Ar is a group of the formula (B1), L and M are both N, $K^a$, $K^b$ and V are H, n is 0, $R_1$ is ethyl, $R_2$ is hydrogen, $R_3$ and $R_4$ are both methyl and $R_5$ has the values listed in Table 14. Thus compound 1 of Table 17 is the same as compound 1 of Table 15 except that in compound 1 of Table 17 L is N instead of CH. Similarly, compounds 2 to 90 of Table 17 are the same as compounds 2 to 90 of Table 15, respectively, except that in the compounds of Table 17 L is N instead of CH.

Table 18

Table 18 consists of 90 compounds of the general formula (1), where Ar is a group of the formula (B1), M is CH, L is N, $K^a$, $K^b$ and V are H, n is 0, $R_1$ is methyl, $R_2$ is hydrogen, $R_3$ and $R_4$ are both methyl and $R_5$ has the values listed in Table 14. Thus compound 1 of Table 18 is the same as compound 1 of Table 14 except that in compound 1 of Table 18 L is N instead of CH and M is CH instead of N. Similarly, compounds 2 to 90 of Table 18 are the same as compounds 2 to 90 of Table 14, respectively, except that in the compounds of Table 18 L is N instead of CH and M is CH instead of N.

Table 19

Table 19 consists of 90 compounds of the general formula (1), where Ar is a group of the formula (B1), M is CH, L is N, $K^a$, $K^b$ and V are H, n is 0, $R_1$ is ethyl, $R_2$ is hydrogen, $R_3$ and $R_4$ are both methyl and $R_5$ has the values listed in Table 14. Thus compound 1 of Table 19 is the same as compound 1 of Table 15 except that in compound 1 of Table 19 L is N instead of CH and M is CH instead of N. Similarly, compounds 2 to 90 of Table 19 are the same as compounds 2 to 90 of Table 15, respectively, except that in the compounds of Table 19 L is N instead of CH and M is CH instead of N.

Table 20

Table 20 consists of 90 compounds of the general formula (1), where Ar is a group of the formula (B1), M is N, L is C—Br, $K^a$, $K^b$ and V are H, n is 0, $R_1$ is methyl, $R_2$ is hydrogen, $R_3$ and $R_4$ are both methyl and $R_5$ has the values listed in Table 14. Thus compound 1 of Table 20 is the same as compound 1 of Table 14 except that in compound 1 of Table 20 L is C—Br instead of CH. Similarly, compounds 2 to 90 of Table 20 are the same as compounds 2 to 90 of Table 14, respectively, except that in the compounds of Table 20 L is C—Br instead of CH.

Table 21

Table 21 consists of 90 compounds of the general formula (1), where Ar is a group of the formula (B1), M is N, L is C—Br, $K^a$, $K^b$ and V are H, n is 0, $R_1$ is ethyl, $R_2$ is hydrogen, $R_3$ and $R_4$ are both methyl and $R_5$ has the values listed in Table 14. Thus compound 1 of Table 21 is the same as compound 1 of Table 15 except that in compound 1 of Table 21 L is C—Br instead of CH. Similarly, compounds 2 to 90 of Table 21 are the same as compounds 2 to 90 of Table 15, respectively, except that in the compounds of Table 21 L is C—Br instead of CH.

Table 22

Table 22 consists of 90 compounds of the general formula (1), where Ar is a group of the formula (B1), M is N, L is C—F, $K^a$, $K^b$ and V are H, n is 0, $R_1$ is methyl, $R_2$ is hydrogen, $R_3$ and $R_4$ are both methyl and $R_5$ has the values listed in Table 14. Thus compound 1 of Table 22 is the same as compound 1 of Table 14 except that in compound 1 of Table 22 L is C—F instead of CH. Similarly, compounds 2 to 90 of Table 22 are the same as compounds 2 to 90 of Table 14, respectively, except that in the compounds of Table 22 L is C—F instead of CH.

Table 23

Table 23 consists of 90 compounds of the general formula (1), where Ar is a group of the formula (B1), M is N, L is C—Cl, $K^a$, $K^b$ and V are H, n is 0, $R_1$ is methyl, $R_2$ is hydrogen, $R_3$ and $R_4$ are both methyl and $R_5$ has the values listed in Table 14. Thus compound 1 of Table 23 is the same as compound 1 of Table 14 except that in compound 1 of Table 23 L is C—Cl instead of CH. Similarly, compounds 2 to 90 of Table 23 are the same as compounds 2 to 90 of Table 14, respectively, except that in the compounds of Table 23 L is C—Cl instead of CH.

Table 24

Table 24 consists of 90 compounds of the general formula (1), where Ar is a group of the formula (B1), M is N, L is CH, $K^a$ and $K^b$ are H, V is Br, n is 0, $R_1$ is methyl, $R_2$ is hydrogen, $R_3$ and $R_4$ are both methyl and $R_5$ has the values listed in Table 14. Thus compound 1 of Table 24 is the same as compound 1 of Table 14 except that in compound 1 of Table 24 V is Br instead of H. Similarly, compounds 2 to 90 of Table 24 are the same as compounds 2 to 90 of Table 14, respectively, except that in the compounds of Table 23 V is Br instead of H.

Table 25

Table 25 consists of 90 compounds of the general formula (1), where Ar is a group of the formula (B1), M is N, L is C—Br, $K^a$ and $K^b$ are H, V is Cl, n is 0, $R_1$ is methyl, $R_2$ is hydrogen, $R_3$ and $R_4$ are both methyl and $R_5$ has the values listed in Table 14. Thus compound 1 of Table 25 is the same as compound 1 of Table 21 except that in compound 1 of Table 25 V is Cl instead of H. Similarly, compounds 2 to 90 of Table 25 are the same as compounds 2 to 90 of Table 21, respectively, except that in the compounds of Table 25 V is Cl instead of H.

Table 26

Table 26 consists of 90 compounds of the general formula (1), where Ar is a group of the formula (B1), M is N, L is C—Br, $K^a$ and $K^b$ are H, V is Br, n is 0, $R_1$ is methyl, $R_2$ is hydrogen, $R_3$ and $R_4$ are both methyl and $R_5$ has the values listed in Table 14. Thus compound 1 of Table 26 is the same as compound 1 of Table 21 except that in compound 1 of Table 26 V is Br instead of H. Similarly, compounds 2 to 90 of Table 26 are the same as compounds 2 to 90 of Table 21, respectively, except that in the compounds of Table 26 V is Br instead of H.

Table 27

Table 27 consists of 90 compounds of the general formula (1), where Ar is a group of the formula (B2), M is N, L is CH, $K^a$, $K^b$ and V are H, n is 0, $R_1$ is methyl, $R_2$ is hydrogen, $R_3$ and $R_4$ are both methyl and $R_5$ has the values listed in Table 14. Thus compound 1 of Table 27 is the same as compound 1 of Table 14 except that in compound 1 of Table 27 Ar is (B2) instead of (B1). Similarly, compounds 2 to 90 of Table 27 are the same as compounds 2 to 90 of Table 14, respectively, except that in the compounds of Table 27 Ar is (B2) instead of (B1).

Table 28

Table 28 consists of 90 compounds of the general formula (1), where Ar is a group of the formula (B1), M is CH, L is C—Br, $K^a$, $K^b$ and V are H, n is 0, $R_1$ is methyl, $R_2$ is hydrogen, $R_3$ and $R_4$ are both methyl and $R_5$ has the values listed in Table 14. Thus compound 1 of Table 28 is the same as compound 1 of Table 20 except that in compound 1 of Table 28 M is CH instead of N. Similarly, compounds 2 to 90 of Table 28 are the same as compounds 2 to 90 of Table 20, respectively, except that in the compounds of Table 28 M is CH instead of N.

Table 29

Table 29 consists of 90 compounds of the general formula (1), where Ar is a group of the formula (B1), M is N, L is C—Cl, $K^a$, $K^b$ and V are H, n is 0, $R_1$ is methyl, $R_2$ is ethoxymethyl, $R_3$ and $R_4$ are both methyl and $R_5$ has the values listed in Table 14. Thus compound 1 of Table 29 is the same as compound 1 of Table 23 except that in compound 1 of Table 29 $R_2$ is ethoxymethyl instead of H. Similarly, compounds 2 to 90 of Table 29 are the same as compounds 2 to 90 of Table 23, respectively, except that in the compounds of Table 29 $R_2$ is ethoxymethyl instead of H.

Table 30

Table 30 consists of 90 compounds of the general formula (1), where Ar is a group of the formula (B1), M is N, L is C—F, $K^a$, $K^b$ and V are H, n is 0, $R_1$ is methyl, $R_2$ is benzyloxymethyl, $R_3$ and $R_4$ are both methyl and $R_5$ has the values listed in Table 14. Thus compound 1 of Table 30 is the same as compound 1 of Table 22 except that in compound 1 of Table 30 $R_2$ is benzyloxymethyl instead of H. Similarly, compounds 2 to 90 of Table 30 are the same as compounds 2 to 90 of Table 22, respectively, except that in the compounds of Table 30 $R_2$ is benzyloxymethyl instead of H.

TABLE 31

The compounds in Table 31 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 3-position of the pyridine ring in the group of the formula (C) (referred to as 3-pyridines).

| C'd No | $A^4$ | $A^5$ | $R^1$ | $R^2$ | $R^3$ | $R^4$ | $R^5$ |
|---|---|---|---|---|---|---|---|
| 1 | H | 5-Cl | $C_2H_5$ | H | $CH_3$ | $CH_3$ | $C_2H_5$ |
| 2 | H | 5-Cl | $CH_3$ | H | $CH_3$ | $CH_3$ | H |
| 3 | H | 5-Cl | $CH_3$ | H | $CH_3$ | $CH_3$ | $CH_3$ |
| 4 | H | 5-Cl | $C_2H_5$ | H | $CH_3$ | $CH_3$ | H |
| 5 | H | 5-Cl | $C_2H_5$ | H | $CH_3$ | $CH_3$ | $CH_3$ |
| 6 | H | 5-Cl | $C_2H_5$ | $CH_2OC_2H_5$ | $CH_3$ | $CH_3$ | $CH_3$ |
| 7 | H | 5-Cl | $C_2H_5$ | $CH_3$ | $CH_3$ | $CH_3$ | H |
| 8 | H | 5-Cl | $C_2H_5$ | $CH_3$ | $CH_3$ | $CH_3$ | $CH_3$ |
| 9 | 6-$CH_3$ | H | $C_2H_5$ | H | $CH_3$ | $CH_3$ | H |
| 10 | 6-$CH_3$ | H | $C_2H_5$ | H | $CH_3$ | $CH_3$ | $CH_3$ |
| 11 | H | 5-Br | $C_2H_5$ | H | $CH_3$ | $CH_3$ | H |
| 12 | H | 5-Br | $C_2H_5$ | H | $CH_3$ | $CH_3$ | $CH_3$ |
| 13 | H | 5-Br | $C_2H_5$ | H | $CH_3$ | $CH_3$ | $C_2H_5$ |
| 14 | H | 5-CON(i-$C_3H_7$)$_2$ | $C_2H_5$ | H | $CH_3$ | $CH_3$ | H |
| 15 | H | 5-CON(i-$C_3H_7$)$_2$ | $C_2H_5$ | H | $CH_3$ | $CH_3$ | $C_2H_5$ |
| 16 | H | 5-$CO_2CH_3$ | $C_2H_5$ | H | $CH_3$ | $CH_3$ | H |
| 17 | H | 5-$CO_2CH_3$ | $C_2H_5$ | H | $CH_3$ | $CH_3$ | $C_2H_5$ |
| 18 | H | 5-$CO_2H$ | $C_2H_5$ | H | $CH_3$ | $CH_3$ | H |
| 19 | H | 5-$CO_2H$ | $C_2H_5$ | H | $CH_3$ | $CH_3$ | $C_2H_5$ |
| 20 | H | 5-Cl | $CH_3$ | H | $CH_3$ | $CH_3$ | $C_2H_5$ |
| 21 | H | 5-Cl | $CH_3$ | H | $CH_3$ | $CH_3$ | cyclopropyl |
| 22 | H | 5-Cl | $C_2H_5$ | H | $CH_3$ | $CH_3$ | cyclopropyl |
| 23 | H | 5-Cl | $CH_3$ | H | $CH_3$ | $CH_3$ | $CH_2CF_3$ |
| 24 | H | 5-Cl | $C_2H_5$ | H | $CH_3$ | $CH_3$ | $CH_2CF_3$ |
| 25 | H | 5-Cl | $CH_3$ | H | $CH_3$ | $CH_3$ | $CH_2OCH_3$ |
| 26 | H | 5-Cl | $C_2H_5$ | H | $CH_3$ | $CH_3$ | $CH_2OCH_3$ |
| 27 | H | 5-Cl | $CH_3$ | $CH_3$ | $CH_3$ | $CH_3$ | $CH_3$ |
| 28 | H | 5-Cl | $CH_3$ | $CH_3$ | $CH_3$ | $CH_3$ | $C_2H_5$ |
| 29 | H | 5-Cl | $C_2H_5$ | $CH_3$ | $CH_3$ | $CH_3$ | $C_2H_5$ |
| 30 | H | 5-Cl | $CH_3$ | $CH_2OC_2H_5$ | $CH_3$ | $CH_3$ | H |
| 31 | H | 5-Cl | $CH_3$ | $CH_2OC_2H_5$ | $CH_3$ | $CH_3$ | $CH_3$ |
| 32 | H | 5-Cl | $CH_3$ | $CH_2OC_2H_5$ | $CH_3$ | $CH_3$ | $C_2H_5$ |
| 33 | H | 5-Cl | $C_2H_5$ | $CH_2OC_2H_5$ | $CH_3$ | $CH_3$ | H |
| 34 | H | 5-Cl | $C_2H_5$ | $CH_2OC_2H_5$ | $CH_3$ | $CH_3$ | $C_2H_5$ |
| 35 | H | 5-Cl | $CH_3$ | H | $CH_2CH=CH_2$ | $CH_3$ | H |
| 36 | H | 5-Cl | $CH_3$ | H | $CH_2CH=CH_2$ | $CH_3$ | $CH_3$ |
| 37 | H | 5-Cl | $C_2H_5$ | H | $CH_2CH=CH_2$ | $CH_3$ | H |

TABLE 31-continued

The compounds in Table 31 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 3-position of the pyridine ring in the group of the formula (C) (referred to as 3-pyridines).

| C'd No | $A^4$ | $A^5$ | $R^1$ | $R^2$ | $R^3$ | $R^4$ | $R^5$ |
|---|---|---|---|---|---|---|---|
| 38 | H | 5-Cl | $C_2H_5$ | H | $CH_2CH=CH_2$ | $CH_3$ | $CH_3$ |
| 39 | H | 5-Cl | $CH_3$ | H | $CH_2CH=CH_2$ | $CH_3$ | $C_2H_5$ |
| 40 | H | 5-Cl | $C_2H_5$ | H | $CH_2CH=CH_2$ | $CH_3$ | $C_2H_5$ |
| 41 | 6-$CH_3$ | 5-Cl | $CH_3$ | H | $CH_3$ | $CH_3$ | H |
| 42 | 6-$CH_3$ | 5-Cl | $CH_3$ | H | $CH_3$ | $CH_3$ | $CH_3$ |
| 43 | 6-$CH_3$ | 5-Cl | $C_2H_5$ | H | $CH_3$ | $CH_3$ | H |
| 44 | 6-$CH_3$ | 5-Cl | $C_2H_5$ | H | $CH_3$ | $CH_3$ | $CH_3$ |
| 45 | 6-$CH_3$ | 5-Cl | $CH_3$ | H | $CH_3$ | $CH_3$ | $C_2H_5$ |
| 46 | 6-$CH_3$ | 5-Cl | $C_2H_5$ | H | $CH_3$ | $CH_3$ | $C_2H_5$ |
| 47 | H | 5-Cl | $CH_3$ | H | $CH_3$ | $CH_3$ | n-$C_3H_7$ |
| 48 | H | 5-Cl | $C_2H_5$ | H | $CH_3$ | $CH_3$ | n-$C_3H_7$ |
| 49 | H | 5-Br | $CH_3$ | H | $CH_3$ | $CH_3$ | n-$C_3H_7$ |
| 50 | H | 5-Br | $C_2H_5$ | H | $CH_3$ | $CH_3$ | n-$C_3H_7$ |
| 51 | H | 5-Cl | $CH_3$ | H | $CH_3$ | $C_2H_5$ | H |
| 52 | H | 5-Cl | $CH_3$ | H | $CH_3$ | $C_2H_5$ | $CH_3$ |
| 53 | H | 5-Cl | $C_2H_5$ | H | $CH_3$ | $C_2H_5$ | H |
| 54 | H | 5-Cl | $C_2H_5$ | H | $CH_3$ | $C_2H_5$ | $CH_3$ |
| 55 | H | 5-Cl | $CH_3$ | H | $CH_3$ | $C_2H_5$ | $C_2H_5$ |
| 56 | H | 5-Cl | $C_2H_5$ | H | $CH_3$ | $C_2H_5$ | $C_2H_5$ |
| 57 | 6-Cl | 5-Cl | $CH_3$ | H | $CH_3$ | $C_2H_5$ | $CH_2OSi(CH_3)_2$(t-$C_4H_9$) |
| 58 | 6-Cl | 5-Cl | $C_2H_5$ | H | $CH_3$ | $C_2H_5$ | $CH_2OSi(CH_3)_2$(t-$C_4H_9$) |
| 59 | H | 5-Cl | $CH_3$ | H | $CH_3$ | $C_2H_5$ | cyclopropyl |
| 60 | H | 5-Cl | $C_2H_5$ | H | $CH_3$ | $C_2H_5$ | cyclopropyl |
| 61 | H | 5-Cl | $CH_3$ | H | $CH_3$ | $CH_3$ | $CH_2OSi(CH_3)_2$(t-$C_4H_9$) |
| 62 | H | 5-Cl | $C_2H_5$ | H | $CH_3$ | $CH_3$ | $CH_2OSi(CH_3)_2$(t-$C_4H_9$) |
| 63 | H | 5-Cl | $CH_3$ | H | $CH_3$ | $C_2H_5$ | $CH_2CF_3$ |
| 64 | H | 5-Cl | $C_2H_5$ | H | $CH_3$ | $C_2H_5$ | $CH_2CF_3$ |
| 65 | H | 5-Cl | $CH_3$ | H | $CH_3$ | $C_2H_5$ | $CH_2OCH_3$ |
| 66 | H | 5-Cl | $C_2H_5$ | H | $CH_3$ | $C_2H_5$ | $CH_2OCH_3$ |
| 67 | H | 5-Cl | $CH_3$ | H | $CH_3$ | $CF_3$ | H |
| 68 | H | 5-Cl | $CH_3$ | H | $CH_3$ | $CF_3$ | $CH_3$ |
| 69 | H | 5-Cl | $C_2H_5$ | H | $CH_3$ | $CF_3$ | H |
| 70 | H | 5-Cl | $C_2H_5$ | H | $CH_3$ | $CF_3$ | $CH_3$ |
| 71 | H | 5-Cl | $CH_3$ | H | $CH_3$ | $CF_3$ | $C_2H_5$ |
| 72 | H | 5-Cl | $C_2H_5$ | H | $CH_3$ | $CF_3$ | $C_2H_5$ |
| 73 | H | 5-Cl | $CH_3$ | H | $CH_2CH_2$ | | H |
| 74 | H | 5-Cl | $CH_3$ | H | $CH_2CH_2$ | | $CH_3$ |
| 75 | H | 5-Cl | $C_2H_5$ | H | $CH_2CH_2$ | | H |
| 76 | H | 5-Cl | $C_2H_5$ | H | $CH_2CH_2$ | | $CH_3$ |
| 77 | H | 5-Cl | $CH_3$ | H | $CH_2CH_2$ | | $C_2H_5$ |
| 78 | H | 5-Cl | $C_2H_5$ | H | $CH_2CH_2$ | | $C_2H_5$ |
| 79 | H | 5-Cl | $CH_3$ | H | $CH_2CH_2$ | | cyclopropyl |
| 80 | H | 5-Cl | $C_2H_5$ | H | $CH_2CH_2$ | | cyclopropyl |
| 81 | H | 5-Cl | $CH_3$ | H | $CH_2CH_2$ | | $CH_2CF_3$ |
| 82 | H | 5-Cl | $C_2H_5$ | H | $CH_2CH_2$ | | $CH_2CF_3$ |
| 83 | H | 5-Cl | $CH_3$ | H | $CH_2CH_2$ | | $CH_2OCH_3$ |
| 84 | H | 5-Cl | $CH_3$ | H | $CH_2CH_2$ | | cyclopropyl |
| 85 | H | 5-Cl | $C_2H_5$ | H | $CH_2CH_2$ | | cyclopropyl |
| 86 | H | 5-Cl | $CH_3$ | H | $CH_2CH_2$ | | $CH_2CF_3$ |
| 87 | H | 5-Cl | $C_2H_5$ | H | $CH_2CH_2$ | | $CH_2CF_3$ |
| 88 | H | 5-Cl | $CH_3$ | H | $CH_2CH_2$ | | $CH_2OCH_3$ |
| 89 | H | 5-Cl | $C_2H_5$ | H | $CH_2CH_2$ | | $CH_2OCH_3$ |
| 90 | H | 5-Br | $CH_3$ | H | $CH_3$ | $CH_3$ | H |
| 91 | H | 5-Br | $CH_3$ | H | $CH_3$ | $CH_3$ | $CH_3$ |
| 92 | H | 5-Br | $CH_3$ | H | $CH_3$ | $CH_3$ | $C_2H_5$ |
| 93 | 6-Cl | 5-Cl | $CH_3$ | H | $CH_3$ | $CH_3$ | H |
| 94 | 6-Cl | 5-Cl | $C_2H_5$ | H | $CH_3$ | $CH_3$ | H |
| 95 | 6-Cl | 5-Cl | $CH_3$ | H | $CH_3$ | $CH_3$ | $CH_3$ |
| 96 | 6-Cl | 5-Cl | $C_2H_5$ | H | $CH_3$ | $CH_3$ | $CH_3$ |
| 97 | 6-Cl | 5-Cl | $CH_3$ | H | $CH_3$ | $CH_3$ | $C_2H_5$ |
| 98 | 6-Cl | 5-Cl | $C_2H_5$ | H | $CH_3$ | $CH_3$ | $C_2H_5$ |
| 99 | 6-Cl | 5-Cl | $CH_3$ | H | $CH_3$ | $CH_3$ | $CH_2OCH_3$ |
| 100 | 6-Cl | 5-Cl | $C_2H_5$ | H | $CH_3$ | $CH_3$ | $CH_2OCH_3$ |
| 101 | 4-$SCH_3$ | 5-$OC_6H_5$ | $CH_3$ | H | $CH_3$ | $CH_3$ | H |
| 102 | 4-$SCH_3$ | 5-$OC_6H_5$ | $C_2H_5$ | H | $CH_3$ | $CH_3$ | H |

TABLE 31-continued

The compounds in Table 31 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 3-position of the pyridine ring in the group of the formula (C) (referred to as 3-pyridines).

| C'd No | $A^4$ | $A^5$ | $R^1$ | $R^2$ | $R^3$ | $R^4$ | $R^5$ |
|---|---|---|---|---|---|---|---|
| 103 | 4-SCH$_3$ | 5-OC$_6$H$_5$ | CH$_3$ | H | CH$_3$ | CH$_3$ | CH$_3$ |
| 104 | 4-SCH$_3$ | 5-OC$_6$H$_5$ | C$_2$H$_5$ | H | CH$_3$ | CH$_3$ | CH$_3$ |
| 105 | 4-SCH$_3$ | 5-OC$_6$H$_5$ | CH$_3$ | H | CH$_3$ | CH$_3$ | C$_2$H$_5$ |
| 106 | 4-SCH$_3$ | 5-OC$_6$H$_5$ | C$_2$H$_5$ | H | CH$_3$ | CH$_3$ | C$_2$H$_5$ |
| 107 | H | 5-CON(i-C$_3$H$_7$)$_2$ | CH$_3$ | H | CH$_3$ | CH$_3$ | H |
| 108 | H | 5-CON(i-C$_3$H$_7$)$_2$ | C$_2$H$_5$ | H | CH$_3$ | CH$_3$ | H |
| 109 | H | 5-CON(i-C$_3$H$_7$)$_2$ | CH$_3$ | H | CH$_3$ | CH$_3$ | CH$_3$ |
| 110 | H | 5-CON(i-C$_3$H$_7$)$_2$ | C$_2$H$_5$ | H | CH$_3$ | CH$_3$ | CH$_3$ |
| 111 | H | 5-CON(i-C$_3$H$_7$)$_2$ | CH$_3$ | H | CH$_3$ | CH$_3$ | C$_2$H$_5$ |
| 112 | H | 5-CO$_2$—CH$_2$C$_6$H$_5$ | CH$_3$ | H | CH$_3$ | CH$_3$ | H |
| 113 | H | 5-CO$_2$—CH$_2$C$_6$H$_5$ | C$_2$H$_5$ | H | CH$_3$ | CH$_3$ | H |
| 114 | H | 5-CO$_2$—CH$_2$C$_6$H$_5$ | CH$_3$ | H | CH$_3$ | CH$_3$ | CH$_3$ |
| 115 | H | 5-CO$_2$—CH$_2$C$_6$H$_5$ | C$_2$H$_5$ | H | CH$_3$ | CH$_3$ | CH$_3$ |
| 116 | H | 5-CO$_2$—CH$_2$C$_6$H$_5$ | CH$_3$ | H | CH$_3$ | CH$_3$ | C$_2$H$_5$ |
| 117 | H | 5-CO$_2$—CH$_2$C$_6$H$_5$ | C$_2$H$_5$ | H | CH$_3$ | CH$_3$ | C$_2$H$_5$ |
| 118 | H | 5-CON(i-C$_3$H$_7$)$_2$ | CH$_3$ | H | CH$_3$ | C$_2$H$_5$ | H |
| 119 | H | 5-CON(i-C$_3$H$_7$)$_2$ | C$_2$H$_5$ | H | CH$_3$ | C$_2$H$_5$ | H |
| 120 | H | 5-CON(i-C$_3$H$_7$)$_2$ | CH$_3$ | H | CH$_3$ | C$_2$H$_5$ | CH$_3$ |
| 121 | H | 5-CON(i-C$_3$H$_7$)$_2$ | C$_2$H$_5$ | H | CH$_3$ | C$_2$H$_5$ | CH$_3$ |
| 122 | H | 5-CON(i-C$_3$H$_7$)$_2$ | CH$_3$ | H | CH$_3$ | C$_2$H$_5$ | C$_2$H$_5$ |
| 123 | H | 5-CON(i-C$_3$H$_7$)$_2$ | C$_2$H$_5$ | H | CH$_3$ | C$_2$H$_5$ | C$_2$H$_5$ |
| 124 | H | 5-COCH$_3$ | CH$_3$ | H | CH$_3$ | CH$_3$ | H |
| 125 | H | 5-COCH$_3$ | C$_2$H$_5$ | H | CH$_3$ | CH$_3$ | H |
| 126 | H | 5-COCH$_3$ | CH$_3$ | H | CH$_3$ | CH$_3$ | CH$_3$ |
| 127 | H | 5-COCH$_3$ | C$_2$H$_5$ | H | CH$_3$ | CH$_3$ | CH$_3$ |
| 128 | H | 5-COCH$_3$ | CH$_3$ | H | CH$_3$ | CH$_3$ | C$_2$H$_5$ |
| 129 | H | 5-COCH$_3$ | C$_2$H$_5$ | H | CH$_3$ | CH$_3$ | C$_2$H$_5$ |
| 130 | H | 5-CN | CH$_3$ | H | CH$_3$ | CH$_3$ | H |
| 131 | H | 5-CN | C$_2$H$_5$ | H | CH$_3$ | CH$_3$ | H |
| 132 | H | 5-CN | CH$_3$ | H | CH$_3$ | CH$_3$ | CH$_3$ |
| 133 | H | 5-CN | C$_2$H$_5$ | H | CH$_3$ | CH$_3$ | CH$_3$ |
| 134 | H | 5-CN | CH$_3$ | H | CH$_3$ | CH$_3$ | C$_2$H$_5$ |
| 135 | H | 5-CN | C$_2$H$_5$ | H | CH$_3$ | CH$_3$ | C$_2$H$_5$ |
| 136 | H | 5-C≢CH | CH$_3$ | H | CH$_3$ | CH$_3$ | CH$_3$ |
| 137 | H | 5-C≢CH | C$_2$H$_5$ | H | CH$_3$ | CH$_3$ | CH$_3$ |
| 138 | H | 5-C≢CH | CH$_3$ | H | CH$_3$ | CH$_3$ | C$_2$H$_5$ |
| 139 | H | 5-C≢CH | C$_2$H$_5$ | H | CH$_3$ | CH$_3$ | C$_2$H$_5$ |
| 140 | H | 5-CH=CH$_2$ | CH$_3$ | H | CH$_3$ | CH$_3$ | H |
| 141 | H | 5-CH=CH$_2$ | C$_2$H$_5$ | H | CH$_3$ | CH$_3$ | H |
| 142 | H | 5-CH=CH$_2$ | CH$_3$ | H | CH$_3$ | CH$_3$ | CH$_3$ |
| 143 | H | 5-CH=CH$_2$ | C$_2$H$_5$ | H | CH$_3$ | CH$_3$ | CH$_3$ |
| 144 | H | 5-Cl | CH$_3$ | H | CH$_3$ | CH$_3$ | CH$_2$OC$_2$H$_5$ |
| 145 | H | 5-Cl | C$_2$H$_5$ | H | CH$_3$ | CH$_3$ | CH$_2$OC$_2$H$_5$ |
| 146 | H | 5-Cl | CH$_3$ | H | CH$_3$ | CH$_3$ | CH(OCH$_3$)CH$_3$ |
| 147 | H | 5-Cl | C$_2$H$_5$ | H | CH$_3$ | CH$_3$ | CH(OCH$_3$)CH$_3$ |
| 148 | H | 5-Cl | CH$_3$ | H | CH$_3$ | CH$_3$ | n-C$_3$H$_6$—CN |
| 149 | H | 5-Cl | CH$_3$ | H | CH$_3$ | CH$_3$ | n-C$_3$H$_6$—Cl |
| 150 | H | 5-Br | C$_2$H$_5$ | H | CH$_3$ | CH$_3$ | i-C$_3$H$_7$ |
| 151 | H | 5-Br | C$_2$H$_5$ | H | CH$_3$ | CH$_3$ | n-C$_4$H$_9$ |
| 152 | H | 5-Br | C$_2$H$_5$ | H | CH$_3$ | CH$_3$ | sec-C$_4$H$_9$ |
| 153 | H | 5-Br | C$_2$H$_5$ | H | CH$_3$ | CH$_3$ | iso-C$_4$H$_9$ |
| 154 | H | 5-Br | C$_2$H$_5$ | H | CH$_3$ | CH$_3$ | tert-C$_4$H$_9$ |
| 155 | H | 5-Br | C$_2$H$_5$ | H | CH$_3$ | CH$_3$ | HOCH$_2$ |
| 156 | H | 5-Br | C$_2$H$_5$ | H | CH$_3$ | CH$_3$ | HOC$_2$H$_4$ |
| 157 | H | 5-Br | C$_2$H$_5$ | H | CH$_3$ | CH$_3$ | CH$_3$OCH$_2$ |
| 158 | H | 5-Br | C$_2$H$_5$ | H | CH$_3$ | CH$_3$ | CH$_3$OCH$_2$CH$_2$ |
| 159 | H | 5-Br | C$_2$H$_5$ | H | CH$_3$ | CH$_3$ | C$_2$H$_5$OCH$_2$ |

TABLE 31-continued

The compounds in Table 31 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 3-position of the pyridine ring in the group of the formula (C) (referred to as 3-pyridines).

| C'd No | $A^4$ | $A^5$ | $R^1$ | $R^2$ | $R^3$ | $R^4$ | $R^5$ |
|---|---|---|---|---|---|---|---|
| 160 | H | 5-Br | $C_2H_5$ | H | $CH_3$ | $CH_3$ | $CH_3(CH_3O)CH$ |
| 161 | H | 5-Br | $C_2H_5$ | H | $CH_3$ | $CH_3$ | $n-C_3H_7OCH_2$ |
| 162 | H | 5-Br | $C_2H_5$ | H | $CH_3$ | $CH_3$ | $n-C_3H_7OC_2H_4$ |
| 163 | H | 5-Br | $C_2H_5$ | H | $CH_3$ | $CH_3$ | $t-C_4H_9OCH_2$ |
| 164 | H | 5-Br | $C_2H_5$ | H | $CH_3$ | $CH_3$ | $t-C_4H_9OC_2H_4$ |
| 165 | H | 5-Br | $C_2H_5$ | H | $CH_3$ | $CH_3$ | $NC-C_2H_4$ |
| 166 | H | 5-Br | $C_2H_5$ | H | $CH_3$ | $CH_3$ | $NC-n-C_3H_6$ |
| 167 | H | 5-Br | $C_2H_5$ | H | $CH_3$ | $CH_3$ | $NC-n-C_4H_8$ |
| 168 | H | 5-Br | $C_2H_5$ | H | $CH_3$ | $CH_3$ | $(CH_3)_2C(CN)CH_2$ |
| 169 | H | 5-Br | $C_2H_5$ | H | $CH_3$ | $CH_3$ | 2-cyano-cycloprop-1-yl |
| 170 | H | 5-Br | $C_2H_5$ | H | $CH_3$ | $CH_3$ | 4-cyano-cyclohex-1-yl |
| 171 | H | 5-Br | $C_2H_5$ | H | $CH_3$ | $CH_3$ | $C_6H_5OCH_2$ |
| 172 | H | 5-Br | $C_2H_5$ | H | $CH_3$ | $CH_3$ | $C_6H_5OC_2H_4$ |
| 173 | H | 5-Br | $C_2H_5$ | H | $CH_3$ | $CH_3$ | $4-t-C_4H_9-C_6H_4OCH_2$ |
| 174 | H | 5-Br | $C_2H_5$ | H | $CH_3$ | $CH_3$ | $4-F-C_6H_4OCH_2$ |
| 175 | H | 5-Br | $C_2H_5$ | H | $CH_3$ | $CH_3$ | $4-Cl-C_6H_4OCH_2$ |
| 176 | H | 5-Br | $C_2H_5$ | H | $CH_3$ | $CH_3$ | $4-CH_3-C_6H_4OCH_2$ |
| 177 | H | 5-Br | $C_2H_5$ | H | $CH_3$ | $CH_3$ | $4-Br-C_6H_4OCH_2$ |
| 178 | H | 5-Br | $C_2H_5$ | H | $CH_3$ | $CH_3$ | $2-F-C_6H_4OCH_2$ |
| 179 | H | 5-Br | $C_2H_5$ | H | $CH_3$ | $CH_3$ | $3,4-Cl_2-C_6H_3OCH_2$ |
| 180 | H | 5-Br | $C_2H_5$ | H | $CH_3$ | $CH_3$ | $3-CF_3-C_6H_4OCH_2$ |
| 181 | H | 5-Br | $C_2H_5$ | H | $CH_3$ | $CH_3$ | $3,5-Cl_2-C_6H_3OCH_2$ |
| 182 | H | 5-Br | $C_2H_5$ | H | $CH_3$ | $CH_3$ | $4-CF_3O-C_6H_5OCH_2$ |
| 183 | H | 5-Br | $C_2H_5$ | H | $CH_3$ | $CH_3$ | $2-CF_3-C_6H_4OCH_2$ |
| 184 | H | 5-Br | $C_2H_5$ | H | $CH_3$ | $CH_3$ | $4-CF_3-C_6H_4OCH_2$ |
| 185 | H | 5-Br | $C_2H_5$ | H | $CH_3$ | $CH_3$ | $2-Br-C_6H_4OCH_2$ |
| 186 | H | 5-Br | $C_2H_5$ | H | $CH_3$ | $CH_3$ | $2-Cl-C_6H_4OCH_2$ |
| 187 | H | 5-Br | $C_2H_5$ | H | $CH_3$ | $CH_3$ | $2-CH_3-4-Cl-C_6H_3OCH_2$ |
| 188 | H | 5-Br | $C_2H_5$ | H | $CH_3$ | $CH_3$ | $2-CH_3-5-F-C_6H_3OCH_2$ |
| 189 | H | 5-Br | $C_2H_5$ | H | $CH_3$ | $CH_3$ | $3-Cl-C_6H_4OCH_2$ |
| 190 | H | 5-Br | $C_2H_5$ | H | $CH_3$ | $CH_3$ | thien-2-yl-$OCH_2$ |
| 191 | H | 5-Br | $C_2H_5$ | H | $CH_3$ | $CH_3$ | thien-3-yl-$OCH_2$ |
| 192 | H | 5-Br | $C_2H_5$ | H | $CH_3$ | $CH_3$ | $C_6H_5CH_2OCH_2$ |
| 193 | H | 5-Br | $C_2H_5$ | H | $CH_3$ | $CH_3$ | thien-2-yl-$CH_2OCH_2$ |
| 194 | H | 5-Br | $C_2H_5$ | H | $CH_3$ | $CH_3$ | thien-3-yl-$CH_2OCH_2$ |
| 195 | H | 5-Br | $C_2H_5$ | H | $CH_3$ | $CH_3$ | tert-$C_4H_9(CH_3)_2SiOCH_2$ |
| 196 | H | 5-Br | $C_2H_5$ | H | $CH_3$ | $CH_3$ | tert-$C_4H_9(CH_3)_2SiOC_2H_4$ |
| 197 | H | 5-Br | $C_2H_5$ | H | $CH_3$ | $CH_3$ | $C_6H_5$ |
| 198 | H | 5-Br | $C_2H_5$ | H | $CH_3$ | $CH_3$ | $4-t-C_4H_9-C_6H_4$ |
| 199 | H | 5-Br | $C_2H_5$ | H | $CH_3$ | $CH_3$ | $4-F-C_6H_4$ |
| 200 | H | 5-Br | $C_2H_5$ | H | $CH_3$ | $CH_3$ | $4-Cl-C_6H_4$ |
| 201 | H | 5-Br | $C_2H_5$ | H | $CH_3$ | $CH_3$ | $4-CH_3-C_6H_4$ |
| 202 | H | 5-Br | $C_2H_5$ | H | $CH_3$ | $CH_3$ | $4-Br-C_6H_4$ |
| 203 | H | 5-Br | $C_2H_5$ | H | $CH_3$ | $CH_3$ | $3CH_3CO-C_6H_4$ |
| 204 | H | 5-Br | $C_2H_5$ | H | $CH_3$ | $CH_3$ | $3,4-Cl_2-C_6H_3$ |
| 205 | H | 5-Br | $C_2H_5$ | H | $CH_3$ | $CH_3$ | $3-CF_3-C_6H_4$ |
| 206 | H | 5-Br | $C_2H_5$ | H | $CH_3$ | $CH_3$ | $3,5-Cl_2-C_6H_3$ |
| 207 | H | 5-Br | $C_2H_5$ | H | $CH_3$ | $CH_3$ | $4-CF_3O-C_6H_4$ |
| 208 | H | 5-Br | $C_2H_5$ | H | $CH_3$ | $CH_3$ | $2-CF_3-C_6H_4$ |
| 209 | H | 5-Br | $C_2H_5$ | H | $CH_3$ | $CH_3$ | $4-CF_3-C_6H_4$ |
| 210 | H | 5-Br | $C_2H_5$ | H | $CH_3$ | $CH_3$ | $2-Br-C_6H_4$ |
| 211 | H | 5-Br | $C_2H_5$ | H | $CH_3$ | $CH_3$ | $2-Cl-C_6H_4$ |
| 212 | H | 5-Br | $C_2H_5$ | H | $CH_3$ | $CH_3$ | $2-CH_3-4-Cl-C_6H_3$ |
| 213 | H | 5-Br | $C_2H_5$ | H | $CH_3$ | $CH_3$ | $2-CH_3-5-F-C_6H_3$ |
| 214 | H | 5-Br | $C_2H_5$ | H | $CH_3$ | $CH_3$ | $3-Cl-C_6H_4$ |
| 215 | H | 5-Br | $C_2H_5$ | H | $CH_3$ | $CH_3$ | thien-2-yl |
| 216 | H | 5-Br | $C_2H_5$ | H | $CH_3$ | $CH_3$ | thien-3-yl |
| 217 | H | 5-Br | $C_2H_5$ | H | $CH_3$ | $CH_3$ | $C_6H_5CH_2$ |
| 218 | H | 5-Br | $C_2H_5$ | H | $CH_3$ | $CH_3$ | $4-t-C_4H_9-C_6H_4CH_2$ |
| 219 | H | 5-Br | $C_2H_5$ | H | $CH_3$ | $CH_3$ | $4-F-C_6H_4CH_2$ |
| 220 | H | 5-Br | $C_2H_5$ | H | $CH_3$ | $CH_3$ | $4-Cl-C_6H_4CH_2$ |
| 221 | H | 5-Br | $C_2H_5$ | H | $CH_3$ | $CH_3$ | $4-CH_3-C_6H_4CH_2$ |
| 222 | H | 5-Br | $C_2H_5$ | H | $CH_3$ | $CH_3$ | $4-Br-C_6H_4CH_2$ |
| 223 | H | 5-Br | $C_2H_5$ | H | $CH_3$ | $CH_3$ | $2-F-C_6H_4CH_2$ |
| 224 | H | 5-Br | $C_2H_5$ | H | $CH_3$ | $CH_3$ | $3,4-Cl_2-C_6H_3CH_2$ |

TABLE 31-continued

The compounds in Table 31 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 3-position of the pyridine ring in the group of the formula (C) (referred to as 3-pyridines).

| C'd No | $A^4$ | $A^5$ | $R^1$ | $R^2$ | $R^3$ | $R^4$ | $R^5$ |
|---|---|---|---|---|---|---|---|
| 225 | H | 5-Br | $C_2H_5$ | H | $CH_3$ | $CH_3$ | 3-$CF_3$—$C_6H_4CH_2$ |
| 226 | H | 5-Br | $C_2H_5$ | H | $CH_3$ | $CH_3$ | 3,5-$Cl_2$—$C_6H_3CH_2$ |
| 227 | H | 5-Br | $C_2H_5$ | H | $CH_3$ | $CH_3$ | 4-$CF_3O$—$C_6H_5CH_2$ |
| 228 | H | 5-Br | $C_2H_5$ | H | $CH_3$ | $CH_3$ | 2-$CF_3$—$C_6H_4CH_2$ |
| 229 | H | 5-Br | $C_2H_5$ | H | $CH_3$ | $CH_3$ | 4-$CF_3$—$C_6H_4CH_2$ |
| 230 | H | 5-Br | $C_2H_5$ | H | $CH_3$ | $CH_3$ | 2-Br—$C_6H_4CH_2$ |
| 231 | H | 5-Br | $C_2H_5$ | H | $CH_3$ | $CH_3$ | 2-Cl—$C_6H_4CH_2$ |
| 232 | H | 5-Br | $C_2H_5$ | H | $CH_3$ | $CH_3$ | 2-$CH_3$-4-Cl—$C_6H_3CH_2$ |
| 233 | H | 5-Br | $C_2H_5$ | H | $CH_3$ | $CH_3$ | 2-$CH_3$-5-F—$C_6H_3CH_2$ |
| 234 | H | 5-Br | $C_2H_5$ | H | $CH_3$ | $CH_3$ | 3-Cl—$C_6H_4CH_2$ |
| 235 | H | 5-Br | $C_2H_5$ | H | $CH_3$ | $CH_3$ | Cl-n-$C_3H_6$ |
| 236 | H | 5-Cl | $C_2H_5$ | H | $CH_3$ | $CH_3$ | i-$C_3H_7$ |
| 237 | H | 5-Cl | $C_2H_5$ | H | $CH_3$ | $CH_3$ | n-$C_4H_9$ |
| 238 | H | 5-Cl | $C_2H_5$ | H | $CH_3$ | $CH_3$ | sec-$C_4H_9$ |
| 239 | H | 5-Cl | $C_2H_5$ | H | $CH_3$ | $CH_3$ | iso-$C_4H_9$ |
| 240 | H | 5-Cl | $C_2H_5$ | H | $CH_3$ | $CH_3$ | tert-$C_4H_9$ |
| 241 | H | 5-Cl | $C_2H_5$ | H | $CH_3$ | $CH_3$ | $HOCH_2$ |
| 242 | H | 5-Cl | $C_2H_5$ | H | $CH_3$ | $CH_3$ | $HOC_2H_4$ |
| 243 | H | 5-Cl | $C_2H_5$ | H | $CH_3$ | $CH_3$ | $CH_3OCH_2CH_2$ |
| 244 | H | 5-Cl | $C_2H_5$ | H | $CH_3$ | $CH_3$ | n-$C_3H_7OCH_2$ |
| 245 | H | 5-Cl | $C_2H_5$ | H | $CH_3$ | $CH_3$ | n-$C_3H_7OC_2H_4$ |
| 246 | H | 5-Cl | $C_2H_5$ | H | $CH_3$ | $CH_3$ | t-$C_4H_9OCH_2$ |
| 247 | H | 5-Cl | $C_2H_5$ | H | $CH_3$ | $CH_3$ | t-$C_4H_9OC_2H_4$ |
| 248 | H | 5-Cl | $C_2H_5$ | H | $CH_3$ | $CH_3$ | NC—$C_2H_4$ |
| 249 | H | 5-Cl | $C_2H_5$ | H | $CH_3$ | $CH_3$ | NC-n-$C_3H_6$ |
| 250 | H | 5-Cl | $C_2H_5$ | H | $CH_3$ | $CH_3$ | NC-n-$C_4H_8$ |
| 251 | H | 5-Cl | $C_2H_5$ | H | $CH_3$ | $CH_3$ | $(CH_3)_2C(CN)CH_2$ |
| 252 | H | 5-Cl | $C_2H_5$ | H | $CH_3$ | $CH_3$ | 2-cyano-cycloprop-1-yl |
| 253 | H | 5-Cl | $C_2H_5$ | H | $CH_3$ | $CH_3$ | 4-cyano-cyclohex-1-yl |
| 254 | H | 5-Cl | $C_2H_5$ | H | $CH_3$ | $CH_3$ | $C_6H_5OCH_2$ |
| 255 | H | 5-Cl | $C_2H_5$ | H | $CH_3$ | $CH_3$ | $C_6H_5OC_2H_4$ |
| 256 | H | 5-Cl | $C_2H_5$ | H | $CH_3$ | $CH_3$ | 4-t-$C_4H_9$—$C_6H_4OCH_2$ |
| 257 | H | 5-Cl | $C_2H_5$ | H | $CH_3$ | $CH_3$ | 4-F—$C_6H_4OCH_2$ |
| 258 | H | 5-Cl | $C_2H_5$ | H | $CH_3$ | $CH_3$ | 4-Cl—$C_6H_4OCH_2$ |
| 259 | H | 5-Cl | $C_2H_5$ | H | $CH_3$ | $CH_3$ | 4-$CH_3$—$C_6H_4OCH_2$ |
| 260 | H | 5-Cl | $C_2H_5$ | H | $CH_3$ | $CH_3$ | 4-Br—$C_6H_4OCH_2$ |
| 261 | H | 5-Cl | $C_2H_5$ | H | $CH_3$ | $CH_3$ | 2-F—$C_6H_4OCH_2$ |
| 262 | H | 5-Cl | $C_2H_5$ | H | $CH_3$ | $CH_3$ | 3,4-$Cl_2$—$C_6H_3OCH_2$ |
| 263 | H | 5-Cl | $C_2H_5$ | H | $CH_3$ | $CH_3$ | 3-$CF_3$—$C_6H_4OCH_2$ |
| 264 | H | 5-Cl | $C_2H_5$ | H | $CH_3$ | $CH_3$ | 3,5-$Cl_2$—$C_6H_3OCH_2$ |
| 265 | H | 5-Cl | $C_2H_5$ | H | $CH_3$ | $CH_3$ | 4-$CF_3O$—$C_6H_5OCH_2$ |
| 266 | H | 5-Cl | $C_2H_5$ | H | $CH_3$ | $CH_3$ | 2-$CF_3$—$C_6H_4OCH_2$ |
| 267 | H | 5-Cl | $C_2H_5$ | H | $CH_3$ | $CH_3$ | 4-$CF_3$—$C_6H_4OCH_2$ |
| 268 | H | 5-Cl | $C_2H_5$ | H | $CH_3$ | $CH_3$ | 2-Br—$C_6H_4OCH_2$ |
| 269 | H | 5-Cl | $C_2H_5$ | H | $CH_3$ | $CH_3$ | 2-Cl—$C_6H_4OCH_2$ |
| 270 | H | 5-Cl | $C_2H_5$ | H | $CH_3$ | $CH_3$ | 2-$CH_3$-4-Cl—$C_6H_3OCH_2$ |
| 271 | H | 5-Cl | $C_2H_5$ | H | $CH_3$ | $CH_3$ | 2-$CH_3$-5-F—$C_6H_3OCH_2$ |
| 272 | H | 5-Cl | $C_2H_5$ | H | $CH_3$ | $CH_3$ | 3-Cl—$C_6H_4OCH_2$ |
| 273 | H | 5-Cl | $C_2H_5$ | H | $CH_3$ | $CH_3$ | thien-2-yl-$OCH_2$ |
| 274 | H | 5-Cl | $C_2H_5$ | H | $CH_3$ | $CH_3$ | thien-3-yl-$OCH_2$ |
| 275 | H | 5-Cl | $C_2H_5$ | H | $CH_3$ | $CH_3$ | $C_6H_5CH_2OCH_2$ |
| 276 | H | 5-Cl | $C_2H_5$ | H | $CH_3$ | $CH_3$ | thien-2-yl-$CH_2OCH_2$ |
| 277 | H | 5-Cl | $C_2H_5$ | H | $CH_3$ | $CH_3$ | thien-3-yl-$CH_2OCH_2$ |
| 278 | H | 5-Cl | $C_2H_5$ | H | $CH_3$ | $CH_3$ | tert-$C_4H_9(CH_3)_2SiOC_2H_4$ |
| 279 | H | 5-Cl | $C_2H_5$ | H | $CH_3$ | $CH_3$ | $C_6H_5$ |
| 280 | H | 5-Cl | $C_2H_5$ | H | $CH_3$ | $CH_3$ | 4-t-$C_4H_9$—$C_6H_4$ |
| 281 | H | 5-Cl | $C_2H_5$ | H | $CH_3$ | $CH_3$ | 4-F—$C_6H_4$ |
| 282 | H | 5-Cl | $C_2H_5$ | H | $CH_3$ | $CH_3$ | 4-Cl—$C_6H_4$ |
| 283 | H | 5-Cl | $C_2H_5$ | H | $CH_3$ | $CH_3$ | 4-$CH_3$—$C_6H_4$ |
| 284 | H | 5-Cl | $C_2H_5$ | H | $CH_3$ | $CH_3$ | 4-Br—$C_6H_4$ |
| 285 | H | 5-Cl | $C_2H_5$ | H | $CH_3$ | $CH_3$ | 3$CH_3CO$—$C_6H_4$ |
| 286 | H | 5-Cl | $C_2H_5$ | H | $CH_3$ | $CH_3$ | 3,4-$Cl_2$—$C_6H_3$ |
| 287 | H | 5-Cl | $C_2H_5$ | H | $CH_3$ | $CH_3$ | 3-$CF_3$—$C_6H_4$ |
| 288 | H | 5-Cl | $C_2H_5$ | H | $CH_3$ | $CH_3$ | 3,5-$Cl_2$—$C_6H_3$ |
| 289 | H | 5-Cl | $C_2H_5$ | H | $CH_3$ | $CH_3$ | 4-$CF_3O$—$C_6H_4$ |
| 290 | H | 5-Cl | $C_2H_5$ | H | $CH_3$ | $CH_3$ | 2-$CF_3$—$C_6H_4$ |
| 291 | H | 5-Cl | $C_2H_5$ | H | $CH_3$ | $CH_3$ | 4-$CF_3$—$C_6H_4$ |

TABLE 31-continued

The compounds in Table 31 are of the general formula (1) where Ar is a group of the formula (C), n is 0 and the values of $A^4, A^5, R^1, R^2, R^3, R^4$ and $R^5$ are given in the table. The alkanoic acid amide side chain is attached to the 3-position of the pyridine ring in the group of the formula (C) (referred to as 3-pyridines).

| C'd No | $A^4$ | $A^5$ | $R^1$ | $R^2$ | $R^3$ | $R^4$ | $R^5$ |
|---|---|---|---|---|---|---|---|
| 292 | H | 5-Cl | $C_2H_5$ | H | $CH_3$ | $CH_3$ | 2-Br—$C_6H_4$ |
| 293 | H | 5-Cl | $C_2H_5$ | H | $CH_3$ | $CH_3$ | 2-Cl—$C_6H_4$ |
| 294 | H | 5-Cl | $C_2H_5$ | H | $CH_3$ | $CH_3$ | 2-$CH_3$-4-Cl—$C_6H_3$ |
| 295 | H | 5-Cl | $C_2H_5$ | H | $CH_3$ | $CH_3$ | 2-$CH_3$-5-F—$C_6H_3$ |
| 296 | H | 5-Cl | $C_2H_5$ | H | $CH_3$ | $CH_3$ | 3-Cl—$C_6H_4$ |
| 297 | H | 5-Cl | $C_2H_5$ | H | $CH_3$ | $CH_3$ | thien-2-yl |
| 298 | H | 5-Cl | $C_2H_5$ | H | $CH_3$ | $CH_3$ | thien-3-yl |
| 299 | H | 5-Cl | $C_2H_5$ | H | $CH_3$ | $CH_3$ | $C_6H_5CH_2$ |
| 300 | H | 5-Cl | $C_2H_5$ | H | $CH_3$ | $CH_3$ | 4-t-$C_4H_9$—$C_6H_4CH_2$ |
| 301 | H | 5-Cl | $C_2H_5$ | H | $CH_3$ | $CH_3$ | 4-F—$C_6H_4CH_2$ |
| 302 | H | 5-Cl | $C_2H_5$ | H | $CH_3$ | $CH_3$ | 4-Cl—$C_6H_4CH_2$ |
| 303 | H | 5-Cl | $C_2H_5$ | H | $CH_3$ | $CH_3$ | 4-$CH_3$—$C_6H_4CH_2$ |
| 304 | H | 5-Cl | $C_2H_5$ | H | $CH_3$ | $CH_3$ | 4-Br—$C_6H_4CH_2$ |
| 305 | H | 5-Cl | $C_2H_5$ | H | $CH_3$ | $CH_3$ | 2-F—$C_6H_4CH_2$ |
| 306 | H | 5-Cl | $C_2H_5$ | H | $CH_3$ | $CH_3$ | 3,4-$Cl_2$—$C_6H_3CH_2$ |
| 307 | H | 5-Cl | $C_2H_5$ | H | $CH_3$ | $CH_3$ | 3-$CF_3$—$C_6H_4CH_2$ |
| 308 | H | 5-Cl | $C_2H_5$ | H | $CH_3$ | $CH_3$ | 3,5-$Cl_2$—$C_6H_3CH_2$ |
| 309 | H | 5-Cl | $C_2H_5$ | H | $CH_3$ | $CH_3$ | 4-$CF_3O$—$C_6H_5CH_2$ |
| 310 | H | 5-Cl | $C_2H_5$ | H | $CH_3$ | $CH_3$ | 2-$CF_3$—$C_6H_4CH_2$ |
| 311 | H | 5-Cl | $C_2H_5$ | H | $CH_3$ | $CH_3$ | 4-$CF_3$—$C_6H_4CH_2$ |
| 312 | H | 5-Cl | $C_2H_5$ | H | $CH_3$ | $CH_3$ | 2-Br—$C_6H_4CH_2$ |
| 313 | H | 5-Cl | $C_2H_5$ | H | $CH_3$ | $CH_3$ | 2-Cl—$C_6H_4CH_2$ |
| 314 | H | 5-Cl | $C_2H_5$ | H | $CH_3$ | $CH_3$ | 2-$CH_3$-4-Cl—$C_6H_3CH_2$ |
| 315 | H | 5-Cl | $C_2H_5$ | H | $CH_3$ | $CH_3$ | 2-$CH_3$-5-F—$C_6H_3CH_2$ |
| 316 | H | 5-Cl | $C_2H_5$ | H | $CH_3$ | $CH_3$ | 3-Cl—$C_6H_4CH_2$ |
| 317 | H | 5-Cl | $C_2H_5$ | H | $CH_3$ | $CH_3$ | Cl-n-$C_3H_6$ |
| 318 | | | | | | | The N-oxide of Compound No. 2 |
| 319 | | | | | | | The N-oxide of Compound No. 3 |
| 320 | | | | | | | The N-oxide of Compound No. 5 |

TABLE 32

The compounds in Table 32 are of the general formula (1) where Ar is a group of the formula (C), n is 0 and the values of $A^4, A^5, R^1, R^2, R^3, R^4$ and $R^5$ are given in the table. The alkanoic acid amide side chain is attached to the 4-position of the pyridine ring in the group of the formula (C) (referred to as 4-pyridines).

| Compound No. | $A^4$ | $A^5$ | $R^1$ | $R^2$ | $R^3$ | $R^4$ | $R^5$ |
|---|---|---|---|---|---|---|---|
| 1 | H | H | $C_2H_5$ | H | $CH_3$ | $CH_3$ | $CH_3$ |
| 2 | H | H | $CH_3$ | H | $CH_3$ | $CH_3$ | $CH_3$ |
| 3 | H | H | $C_2H_5$ | H | $CH_3$ | $CH_3$ | H |
| 4 | H | H | $CH_3$ | H | $CH_3$ | $CH_3$ | H |
| 5 | H | 2-Cl | $CH_3$ | H | $CH_3$ | $CH_3$ | $CH_3$ |
| 6 | H | 2-Cl | $C_2H_5$ | H | $CH_3$ | $CH_3$ | $CH_3$ |
| 7 | H | 2-Cl | $CH_3$ | H | $CH_3$ | $CH_3$ | H |
| 8 | H | 2-Cl | $C_2H_5$ | H | $CH_3$ | $CH_3$ | H |
| 9 | H | 2-Cl | $CH_3$ | H | $CH_3$ | $CH_3$ | $C_2H_5$ |
| 10 | H | 2-Cl | $C_2H_5$ | H | $CH_3$ | $CH_3$ | $C_2H_5$ |
| 11 | 6-Cl | 2-Cl | $CH_3$ | H | $CH_3$ | $CH_3$ | $CH_3$ |
| 12 | 6-Cl | 2-Cl | $C_2H_5$ | H | $CH_3$ | $CH_3$ | $CH_3$ |
| 13 | 6-Cl | 2-Cl | $CH_3$ | H | $CH_3$ | $CH_3$ | H |
| 14 | 6-Cl | 2-Cl | $C_2H_5$ | H | $CH_3$ | $CH_3$ | H |
| 15 | 6-Cl | 2-Cl | $CH_3$ | H | $CH_3$ | $CH_3$ | $C_2H_5$ |
| 16 | 6-Cl | 2-Cl | $C_2H_5$ | H | $CH_3$ | $CH_3$ | $C_2H_5$ |
| 17 | 6-Cl | 2-Cl | $C_2H_5$ | H | $CH_3$ | $CH_3$ | n-$C_3H_7$ |
| 18 | H | 2-Cl | $CH_3$ | H | $CH_3$ | $CH_3$ | n-$C_3H_7$ |
| 19 | H | 2-Cl | $CH_3$ | H | $CH_3$ | $CH_3$ | $CH_2OCH_3$ |
| 20 | H | 2-Cl | $C_2H_5$ | H | $CH_3$ | $CH_3$ | n-$C_3H_6$—CN |
| 21 | H | 2-Cl | $CH_3$ | H | $CH_3$ | $CH_3$ | n-$C_3H_6$—Cl |
| 22 | H | 2-Cl | $C_2H_5$ | H | $CH_3$ | $CH_3$ | $CH_2CF_3$ |
| 23 | H | 2-Cl | $CH_3$ | H | $CH_3$ | $CH_3$ | cyclopropyl |
| 24 | 6-Cl | 2-Cl | $CH_3$ | H | $CH_3$ | $CH_3$ | $CH_2OCH_3$ |
| 25 | 6-Cl | 2-Cl | $C_2H_5$ | H | $CH_3$ | $CH_3$ | n-$C_3H_6$—CN |
| 26 | 6-Cl | 2-Cl | $CH_3$ | H | $CH_3$ | $CH_3$ | n-$C_3H_6$—Cl |
| 27 | 6-Cl | 2-Cl | $C_2H_5$ | H | $CH_3$ | $CH_3$ | $CH_2CF_3$ |
| 28 | 6-Cl | 2-Cl | $CH_3$ | H | $CH_3$ | $CH_3$ | cyclopropyl |
| 29 | H | 2-Cl | $C_2H_5$ | H | $CH_3$ | $CH_3$ | n-$C_3H_7$ |

TABLE 32-continued

The compounds in Table 32 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 4-position of the pyridine ring in the group of the formula (C) (referred to as 4-pyridines).

| Compound No. | $A^4$ | $A^5$ | $R^1$ | $R^2$ | $R^3$ | $R^4$ | $R^5$ |
|---|---|---|---|---|---|---|---|
| 30 | H | 2-Cl | $C_2H_5$ | H | $CH_3$ | $CH_3$ | $i\text{-}C_3H_7$ |
| 31 | H | 2-Cl | $C_2H_5$ | H | $CH_3$ | $CH_3$ | $n\text{-}C_4H_9$ |
| 32 | H | 2-Cl | $C_2H_5$ | H | $CH_3$ | $CH_3$ | $sec\text{-}C_4H_9$ |
| 33 | H | 2-Cl | $C_2H_5$ | H | $CH_3$ | $CH_3$ | $iso\text{-}C_4H_9$ |
| 34 | H | 2-Cl | $C_2H_5$ | H | $CH_3$ | $CH_3$ | $tert\text{-}C_4H_9$ |
| 35 | H | 2-Cl | $C_2H_5$ | H | $CH_3$ | $CH_3$ | $HOCH_2$ |
| 36 | H | 2-Cl | $C_2H_5$ | H | $CH_3$ | $CH_3$ | $HOC_2H_4$ |
| 37 | H | 2-Cl | $C_2H_5$ | H | $CH_3$ | $CH_3$ | $CH_3OCH_2$ |
| 38 | H | 2-Cl | $C_2H_5$ | H | $CH_3$ | $CH_3$ | $CH_3OCH_2CH_2$ |
| 39 | H | 2-Cl | $C_2H_5$ | H | $CH_3$ | $CH_3$ | $C_2H_5OCH_2$ |
| 40 | H | 2-Cl | $C_2H_5$ | H | $CH_3$ | $CH_3$ | $CH_3(CH_3O)CH$ |
| 41 | H | 2-Cl | $C_2H_5$ | H | $CH_3$ | $CH_3$ | $n\text{-}C_3H_7OCH_2$ |
| 42 | H | 2-Cl | $C_2H_5$ | H | $CH_3$ | $CH_3$ | $n\text{-}C_3H_7OC_2H_4$ |
| 43 | H | 2-Cl | $C_2H_5$ | H | $CH_3$ | $CH_3$ | $t\text{-}C_4H_9OCH_2$ |
| 44 | H | 2-Cl | $C_2H_5$ | H | $CH_3$ | $CH_3$ | $t\text{-}C_4H_9OC_2H_4$ |
| 45 | H | 2-Cl | $C_2H_5$ | H | $CH_3$ | $CH_3$ | $NC\text{—}C_2H_4$ |
| 46 | H | 2-Cl | $C_2H_5$ | H | $CH_3$ | $CH_3$ | $NC\text{-}n\text{-}C_4H_8$ |
| 47 | H | 2-Cl | $C_2H_5$ | H | $CH_3$ | $CH_3$ | $(CH_3)_2C(CN)CH_2$ |
| 48 | H | 2-Cl | $C_2H_5$ | H | $CH_3$ | $CH_3$ | 2-cyano-cycloprop-1-yl |
| 49 | H | 2-Cl | $C_2H_5$ | H | $CH_3$ | $CH_3$ | 4-cyano-cyclohex-1-yl |
| 50 | H | 2-Cl | $C_2H_5$ | H | $CH_3$ | $CH_3$ | $C_6H_5OCH_2$ |
| 51 | H | 2-Cl | $C_2H_5$ | H | $CH_3$ | $CH_3$ | $C_6H_5OC_2H_4$ |
| 52 | H | 2-Cl | $C_2H_5$ | H | $CH_3$ | $CH_3$ | $4\text{-}t\text{-}C_4H_9\text{—}C_6H_4OCH_2$ |
| 53 | H | 2-Cl | $C_2H_5$ | H | $CH_3$ | $CH_3$ | $4\text{-}F\text{—}C_6H_4OCH_2$ |
| 54 | H | 2-Cl | $C_2H_5$ | H | $CH_3$ | $CH_3$ | $4\text{-}Cl\text{—}C_6H_4OCH_2$ |
| 55 | H | 2-Cl | $C_2H_5$ | H | $CH_3$ | $CH_3$ | $4\text{-}CH_3\text{—}C_6H_4OCH_2$ |
| 56 | H | 2-Cl | $C_2H_5$ | H | $CH_3$ | $CH_3$ | $4\text{-}Br\text{—}C_6H_4OCH_2$ |
| 57 | H | 2-Cl | $C_2H_5$ | H | $CH_3$ | $CH_3$ | $2\text{-}F\text{—}C_6H_4OCH_2$ |
| 58 | H | 2-Cl | $C_2H_5$ | H | $CH_3$ | $CH_3$ | $3,4\text{-}Cl_2\text{—}C_6H_3OCH_2$ |
| 59 | H | 2-Cl | $C_2H_5$ | H | $CH_3$ | $CH_3$ | $3\text{-}CF_3\text{—}C_6H_4OCH_2$ |
| 60 | H | 2-Cl | $C_2H_5$ | H | $CH_3$ | $CH_3$ | $3,5\text{-}Cl_2\text{—}C_6H_3OCH_2$ |
| 61 | H | 2-Cl | $C_2H_5$ | H | $CH_3$ | $CH_3$ | $4\text{-}CF_3O\text{—}C_6H_5OCH_2$ |
| 62 | H | 2-Cl | $C_2H_5$ | H | $CH_3$ | $CH_3$ | $2\text{-}CF_3\text{—}C_6H_4OCH_2$ |
| 63 | H | 2-Cl | $C_2H_5$ | H | $CH_3$ | $CH_3$ | $4\text{-}CF_3\text{—}C_6H_4OCH_2$ |
| 64 | H | 2-Cl | $C_2H_5$ | H | $CH_3$ | $CH_3$ | $2\text{-}Br\text{—}C_6H_4OCH_2$ |
| 65 | H | 2-Cl | $C_2H_5$ | H | $CH_3$ | $CH_3$ | $2\text{-}Cl\text{—}C_6H_4OCH_2$ |
| 66 | H | 2-Cl | $C_2H_5$ | H | $CH_3$ | $CH_3$ | $2\text{-}CH_3\text{-}4\text{-}Cl\text{—}C_6H_3OCH_2$ |
| 67 | H | 2-Cl | $C_2H_5$ | H | $CH_3$ | $CH_3$ | $2\text{-}CH_3\text{-}5\text{-}F\text{—}C_6H_3OCH_2$ |
| 68 | H | 2-Cl | $C_2H_5$ | H | $CH_3$ | $CH_3$ | $3\text{-}Cl\text{—}C_6H_4OCH_2$ |
| 69 | H | 2-Cl | $C_2H_5$ | H | $CH_3$ | $CH_3$ | thien-2-yl-$OCH_2$ |
| 70 | H | 2-Cl | $C_2H_5$ | H | $CH_3$ | $CH_3$ | thien-3-yl-$OCH_2$ |
| 71 | H | 2-Cl | $C_2H_5$ | H | $CH_3$ | $CH_3$ | $C_6H_5CH_2OCH_2$ |
| 72 | H | 2-Cl | $C_2H_5$ | H | $CH_3$ | $CH_3$ | thien-2-yl-$CH_2OCH_2$ |
| 73 | H | 2-Cl | $C_2H_5$ | H | $CH_3$ | $CH_3$ | thien-3-yl-$CH_2OCH_2$ |
| 74 | H | 2-Cl | $C_2H_5$ | H | $CH_3$ | $CH_3$ | $tert\text{-}C_4H_9(CH_3)_2SiOCH_2$ |
| 75 | H | 2-Cl | $C_2H_5$ | H | $CH_3$ | $CH_3$ | $tert\text{-}C_4H_9(CH_3)_2SiOC_2H_4$ |
| 76 | H | 2-Cl | $C_2H_5$ | H | $CH_3$ | $CH_3$ | $C_6H_5$ |
| 77 | H | 2-Cl | $C_2H_5$ | H | $CH_3$ | $CH_3$ | $4\text{-}t\text{-}C_4H_9\text{—}C_6H_4$ |
| 78 | H | 2-Cl | $C_2H_5$ | H | $CH_3$ | $CH_3$ | $4\text{-}F\text{—}C_6H_4$ |
| 79 | H | 2-Cl | $C_2H_5$ | H | $CH_3$ | $CH_3$ | $4\text{-}Cl\text{—}C_6H_4$ |
| 80 | H | 2-Cl | $C_2H_5$ | H | $CH_3$ | $CH_3$ | $4\text{-}CH_3\text{—}C_6H_4$ |
| 81 | H | 2-Cl | $C_2H_5$ | H | $CH_3$ | $CH_3$ | $4\text{-}Br\text{—}C_6H_4$ |
| 82 | H | 2-Cl | $C_2H_5$ | H | $CH_3$ | $CH_3$ | $3CH_3CO\text{—}C_6H_4$ |
| 83 | H | 2-Cl | $C_2H_5$ | H | $CH_3$ | $CH_3$ | $3,4\text{-}Cl_2\text{—}C_6H_3$ |
| 84 | H | 2-Cl | $C_2H_5$ | H | $CH_3$ | $CH_3$ | $3\text{-}CF_3\text{—}C_6H_4$ |
| 85 | H | 2-Cl | $C_2H_5$ | H | $CH_3$ | $CH_3$ | $3,5\text{-}Cl_2\text{—}C_6H_3$ |
| 86 | H | 2-Cl | $C_2H_5$ | H | $CH_3$ | $CH_3$ | $4\text{-}CF_3O\text{—}C_6H_4$ |
| 87 | H | 2-Cl | $C_2H_5$ | H | $CH_3$ | $CH_3$ | $2\text{-}CF_3\text{—}C_6H_4$ |
| 88 | H | 2-Cl | $C_2H_5$ | H | $CH_3$ | $CH_3$ | $4\text{-}CF_3\text{—}C_6H_4$ |
| 89 | H | 2-Cl | $C_2H_5$ | H | $CH_3$ | $CH_3$ | $2\text{-}Br\text{—}C_6H_4$ |
| 90 | H | 2-Cl | $C_2H_5$ | H | $CH_3$ | $CH_3$ | $2\text{-}Cl\text{—}C_6H_4$ |
| 91 | H | 2-Cl | $C_2H_5$ | H | $CH_3$ | $CH_3$ | $2\text{-}CH_3\text{-}4\text{-}Cl\text{—}C_6H_3$ |
| 92 | H | 2-Cl | $C_2H_5$ | H | $CH_3$ | $CH_3$ | $2\text{-}CH_3\text{-}5\text{-}F\text{—}C_6H_3$ |
| 93 | H | 2-Cl | $C_2H_5$ | H | $CH_3$ | $CH_3$ | $3\text{-}Cl\text{—}C_6H_4$ |
| 94 | H | 2-Cl | $C_2H_5$ | H | $CH_3$ | $CH_3$ | thien-2-yl |
| 95 | H | 2-Cl | $C_2H_5$ | H | $CH_3$ | $CH_3$ | thien-3-yl |

TABLE 32-continued

The compounds in Table 32 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 4-position of the pyridine ring in the group of the formula (C) (referred to as 4-pyridines).

| Compound No. | $A^4$ | $A^5$ | $R^1$ | $R^2$ | $R^3$ | $R^4$ | $R^5$ |
|---|---|---|---|---|---|---|---|
| 96 | H | 2-Cl | $C_2H_5$ | H | $CH_3$ | $CH_3$ | $C_6H_5CH_2$ |
| 97 | H | 2-Cl | $C_2H_5$ | H | $CH_3$ | $CH_3$ | 4-t-$C_4H_9$—$C_6H_4CH_2$ |
| 98 | H | 2-Cl | $C_2H_5$ | H | $CH_3$ | $CH_3$ | 4-F—$C_6H_4CH_2$ |
| 99 | H | 2-Cl | $C_2H_5$ | H | $CH_3$ | $CH_3$ | 4-Cl—$C_6H_4CH_2$ |
| 100 | H | 2-Cl | $C_2H_5$ | H | $CH_3$ | $CH_3$ | 4-$CH_3$—$C_6H_4CH_2$ |
| 101 | H | 2-Cl | $C_2H_5$ | H | $CH_3$ | $CH_3$ | 4-Br—$C_6H_4CH_2$ |
| 102 | H | 2-Cl | $C_2H_5$ | H | $CH_3$ | $CH_3$ | 2-F—$C_6H_4CH_2$ |
| 103 | H | 2-Cl | $C_2H_5$ | H | $CH_3$ | $CH_3$ | 3,4-$Cl_2$—$C_6H_3CH_2$ |
| 104 | H | 2-Cl | $C_2H_5$ | H | $CH_3$ | $CH_3$ | 3-$CF_3$—$C_6H_4CH_2$ |
| 105 | H | 2-Cl | $C_2H_5$ | H | $CH_3$ | $CH_3$ | 3,5-$Cl_2$—$C_6H_3CH_2$ |
| 106 | H | 2-Cl | $C_2H_5$ | H | $CH_3$ | $CH_3$ | 4-$CF_3O$—$C_6H_5CH_2$ |
| 107 | H | 2-Cl | $C_2H_5$ | H | $CH_3$ | $CH_3$ | 2-$CF_3$—$C_6H_4CH_2$ |
| 108 | H | 2-Cl | $C_2H_5$ | H | $CH_3$ | $CH_3$ | 4-$CF_3$—$C_6H_4CH_2$ |
| 109 | H | 2-Cl | $C_2H_5$ | H | $CH_3$ | $CH_3$ | 2-Br—$C_6H_4CH_2$ |
| 110 | H | 2-Cl | $C_2H_5$ | H | $CH_3$ | $CH_3$ | 2-Cl—$C_6H_4CH_2$ |
| 111 | H | 2-Cl | $C_2H_5$ | H | $CH_3$ | $CH_3$ | 2-$CH_3$-4-Cl—$C_6H_3CH_2$ |
| 112 | H | 2-Cl | $C_2H_5$ | H | $CH_3$ | $CH_3$ | 2-$CH_3$-5-F—$C_6H_3CH_2$ |
| 113 | H | 2-Cl | $C_2H_5$ | H | $CH_3$ | $CH_3$ | 3-Cl—$C_6H_4CH_2$ |
| 114 | H | 2-Cl | $C_2H_5$ | H | $CH_3$ | $CH_3$ | Cl-n-$C_3H_6$ |
| 115 | 6-Cl | 2-Cl | $C_2H_5$ | H | $CH_3$ | $CH_3$ | i-$C_3H_7$ |
| 116 | 6-Cl | 2-Cl | $C_2H_5$ | H | $CH_3$ | $CH_3$ | n-$C_4H_9$ |
| 117 | 6-Cl | 2-Cl | $C_2H_5$ | H | $CH_3$ | $CH_3$ | sec-$C_4H_9$ |
| 118 | 6-Cl | 2-Cl | $C_2H_5$ | H | $CH_3$ | $CH_3$ | iso-$C_4H_9$ |
| 119 | 6-Cl | 2-Cl | $C_2H_5$ | H | $CH_3$ | $CH_3$ | tert-$C_4H_9$ |
| 120 | 6-Cl | 2-Cl | $C_2H_5$ | H | $CH_3$ | $CH_3$ | $HOCH_2$ |
| 121 | 6-Cl | 2-Cl | $C_2H_5$ | H | $CH_3$ | $CH_3$ | $HOC_2H_4$ |
| 122 | 6-Cl | 2-Cl | $C_2H_5$ | H | $CH_3$ | $CH_3$ | $CH_3OCH_2$ |
| 123 | 6-Cl | 2-Cl | $C_2H_5$ | H | $CH_3$ | $CH_3$ | $CH_3OCH_2CH_2$ |
| 124 | 6-Cl | 2-Cl | $C_2H_5$ | H | $CH_3$ | $CH_3$ | $C_2H_5OCH_2$ |
| 125 | 6-Cl | 2-Cl | $C_2H_5$ | H | $CH_3$ | $CH_3$ | $CH_3(CH_3O)CH$ |
| 126 | 6-Cl | 2-Cl | $C_2H_5$ | H | $CH_3$ | $CH_3$ | n-$C_3H_7OCH_2$ |
| 127 | 6-Cl | 2-Cl | $C_2H_5$ | H | $CH_3$ | $CH_3$ | n-$C_3H_7OC_2H_4$ |
| 128 | 6-Cl | 2-Cl | $C_2H_5$ | H | $CH_3$ | $CH_3$ | t-$C_4H_9OCH_2$ |
| 129 | 6-Cl | 2-Cl | $C_2H_5$ | H | $CH_3$ | $CH_3$ | t-$C_4H_9OC_2H_4$ |
| 130 | 6-Cl | 2-Cl | $C_2H_5$ | H | $CH_3$ | $CH_3$ | NC—$C_2H_4$ |
| 131 | 6-Cl | 2-Cl | $C_2H_5$ | H | $CH_3$ | $CH_3$ | NC-n-$C_4H_8$ |
| 132 | 6-Cl | 2-Cl | $C_2H_5$ | H | $CH_3$ | $CH_3$ | $(CH_3)_2C(CN)CH_2$ |
| 133 | 6-Cl | 2-Cl | $C_2H_5$ | H | $CH_3$ | $CH_3$ | 2-cyano-cycloprop-1-yl |
| 134 | 6-Cl | 2-Cl | $C_2H_5$ | H | $CH_3$ | $CH_3$ | 4-cyano-cyclohex-1-yl |
| 135 | 6-Cl | 2-Cl | $C_2H_5$ | H | $CH_3$ | $CH_3$ | $C_6H_5OCH_2$ |
| 136 | 6-Cl | 2-Cl | $C_2H_5$ | H | $CH_3$ | $CH_3$ | $C_6H_5OC_2H_4$ |
| 137 | 6-Cl | 2-Cl | $C_2H_5$ | H | $CH_3$ | $CH_3$ | 4-t-$C_4H_9$—$C_6H_4OCH_2$ |
| 138 | 6-Cl | 2-Cl | $C_2H_5$ | H | $CH_3$ | $CH_3$ | 4-F—$C_6H_4OCH_2$ |
| 139 | 6-Cl | 2-Cl | $C_2H_5$ | H | $CH_3$ | $CH_3$ | 4-Cl—$C_6H_4OCH_2$ |
| 140 | 6-Cl | 2-Cl | $C_2H_5$ | H | $CH_3$ | $CH_3$ | 4-$CH_3$—$C_6H_4OCH_2$ |
| 141 | 6-Cl | 2-Cl | $C_2H_5$ | H | $CH_3$ | $CH_3$ | 4-Br—$C_6H_4OCH_2$ |
| 142 | 6-Cl | 2-Cl | $C_2H_5$ | H | $CH_3$ | $CH_3$ | 2-F—$C_6H_4OCH_2$ |
| 143 | 6-Cl | 2-Cl | $C_2H_5$ | H | $CH_3$ | $CH_3$ | 3,4-$Cl_2$—$C_6H_3OCH_2$ |
| 144 | 6-Cl | 2-Cl | $C_2H_5$ | H | $CH_3$ | $CH_3$ | 3-$CF_3$—$C_6H_4OCH_2$ |
| 145 | 6-Cl | 2-Cl | $C_2H_5$ | H | $CH_3$ | $CH_3$ | 3,5-$Cl_2$—$C_6H_3OCH_2$ |
| 146 | 6-Cl | 2-Cl | $C_2H_5$ | H | $CH_3$ | $CH_3$ | 4-$CF_3O$—$C_6H_5OCH_2$ |
| 147 | 6-Cl | 2-Cl | $C_2H_5$ | H | $CH_3$ | $CH_3$ | 2-$CF_3$—$C_6H_4OCH_2$ |
| 148 | 6-Cl | 2-Cl | $C_2H_5$ | H | $CH_3$ | $CH_3$ | 4-$CF_3$—$C_6H_4OCH_2$ |
| 149 | 6-Cl | 2-Cl | $C_2H_5$ | H | $CH_3$ | $CH_3$ | 2-Br—$C_6H_4OCH_2$ |
| 150 | 6-Cl | 2-Cl | $C_2H_5$ | H | $CH_3$ | $CH_3$ | 2-Cl—$C_6H_4OCH_2$ |
| 151 | 6-Cl | 2-Cl | $C_2H_5$ | H | $CH_3$ | $CH_3$ | 2-$CH_3$-4-Cl—$C_6H_3OCH_2$ |
| 152 | 6-Cl | 2-Cl | $C_2H_5$ | H | $CH_3$ | $CH_3$ | 2-$CH_3$-5-F—$C_6H_3OCH_2$ |
| 153 | 6-Cl | 2-Cl | $C_2H_5$ | H | $CH_3$ | $CH_3$ | 3-Cl—$C_6H_4OCH_2$ |
| 154 | 6-Cl | 2-Cl | $C_2H_5$ | H | $CH_3$ | $CH_3$ | thien-2-yl-$OCH_2$ |
| 155 | 6-Cl | 2-Cl | $C_2H_5$ | H | $CH_3$ | $CH_3$ | thien-3-yl-$OCH_2$ |
| 156 | 6-Cl | 2-Cl | $C_2H_5$ | H | $CH_3$ | $CH_3$ | $C_6H_5CH_2OCH_2$ |
| 157 | 6-Cl | 2-Cl | $C_2H_5$ | H | $CH_3$ | $CH_3$ | thien-2-yl-$CH_2OCH_2$ |
| 158 | 6-Cl | 2-Cl | $C_2H_5$ | H | $CH_3$ | $CH_3$ | thien-3-yl-$CH_2OCH_2$ |
| 159 | 6-Cl | 2-Cl | $C_2H_5$ | H | $CH_3$ | $CH_3$ | tert-$C_4H_9(CH_3)_2SiOCH_2$ |
| 160 | 6-Cl | 2-Cl | $C_2H_5$ | H | $CH_3$ | $CH_3$ | tert-$C_4H_9(CH_3)_2SiOC_2H_4$ |
| 161 | 6-Cl | 2-Cl | $C_2H_5$ | H | $CH_3$ | $CH_3$ | $C_6H_5$ |

TABLE 32-continued

The compounds in Table 32 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 4-position of the pyridine ring in the group of the formula (C) (referred to as 4-pyridines).

| Compound No. | $A^4$ | $A^5$ | $R^1$ | $R^2$ | $R^3$ | $R^4$ | $R^5$ |
|---|---|---|---|---|---|---|---|
| 162 | 6-Cl | 2-Cl | $C_2H_5$ | H | $CH_3$ | $CH_3$ | $4\text{-}t\text{-}C_4H_9\text{—}C_6H_4$ |
| 163 | 6-Cl | 2-Cl | $C_2H_5$ | H | $CH_3$ | $CH_3$ | $4\text{-}F\text{—}C_6H_4$ |
| 164 | 6-Cl | 2-Cl | $C_2H_5$ | H | $CH_3$ | $CH_3$ | $4\text{-}Cl\text{—}C_6H_4$ |
| 165 | 6-Cl | 2-Cl | $C_2H_5$ | H | $CH_3$ | $CH_3$ | $4\text{-}CH_3\text{—}C_6H_4$ |
| 166 | 6-Cl | 2-Cl | $C_2H_5$ | H | $CH_3$ | $CH_3$ | $4\text{-}Br\text{—}C_6H_4$ |
| 167 | 6-Cl | 2-Cl | $C_2H_5$ | H | $CH_3$ | $CH_3$ | $3CH_3CO\text{—}C_6H_4$ |
| 168 | 6-Cl | 2-Cl | $C_2H_5$ | H | $CH_3$ | $CH_3$ | $3,4\text{-}Cl_2\text{—}C_6H_3$ |
| 169 | 6-Cl | 2-Cl | $C_2H_5$ | H | $CH_3$ | $CH_3$ | $3\text{-}CF_3\text{—}C_6H_4$ |
| 170 | 6-Cl | 2-Cl | $C_2H_5$ | H | $CH_3$ | $CH_3$ | $3,5\text{-}Cl_2\text{—}C_6H_3$ |
| 171 | 6-Cl | 2-Cl | $C_2H_5$ | H | $CH_3$ | $CH_3$ | $4\text{-}CF_3O\text{—}C_6H_4$ |
| 172 | 6-Cl | 2-Cl | $C_2H_5$ | H | $CH_3$ | $CH_3$ | $2\text{-}CF_3\text{—}C_6H_4$ |
| 173 | 6-Cl | 2-Cl | $C_2H_5$ | H | $CH_3$ | $CH_3$ | $4\text{-}CF_3\text{—}C_6H_4$ |
| 174 | 6-Cl | 2-Cl | $C_2H_5$ | H | $CH_3$ | $CH_3$ | $2\text{-}Br\text{—}C_6H_4$ |
| 175 | 6-Cl | 2-Cl | $C_2H_5$ | H | $CH_3$ | $CH_3$ | $2\text{-}Cl\text{—}C_6H_4$ |
| 176 | 6-Cl | 2-Cl | $C_2H_5$ | H | $CH_3$ | $CH_3$ | $2\text{-}CH_3\text{-}4\text{-}Cl\text{—}C_6H_3$ |
| 177 | 6-Cl | 2-Cl | $C_2H_5$ | H | $CH_3$ | $CH_3$ | $2\text{-}CH_3\text{-}5\text{-}F\text{—}C_6H_3$ |
| 178 | 6-Cl | 2-Cl | $C_2H_5$ | H | $CH_3$ | $CH_3$ | $3\text{-}Cl\text{—}C_6H_4$ |
| 179 | 6-Cl | 2-Cl | $C_2H_5$ | H | $CH_3$ | $CH_3$ | thien-2-yl |
| 180 | 6-Cl | 2-Cl | $C_2H_5$ | H | $CH_3$ | $CH_3$ | thien-3-yl |
| 181 | 6-Cl | 2-Cl | $C_2H_5$ | H | $CH_3$ | $CH_3$ | $C_6H_5CH_2$ |
| 182 | 6-Cl | 2-Cl | $C_2H_5$ | H | $CH_3$ | $CH_3$ | $4\text{-}t\text{-}C_4H_9\text{—}C_6H_4CH_2$ |
| 183 | 6-Cl | 2-Cl | $C_2H_5$ | H | $CH_3$ | $CH_3$ | $4\text{-}F\text{—}C_6H_4CH_2$ |
| 184 | 6-Cl | 2-Cl | $C_2H_5$ | H | $CH_3$ | $CH_3$ | $4\text{-}Cl\text{—}C_6H_4CH_2$ |
| 185 | 6-Cl | 2-Cl | $C_2H_5$ | H | $CH_3$ | $CH_3$ | $4\text{-}CH_3\text{—}C_6H_4CH_2$ |
| 186 | 6-Cl | 2-Cl | $C_2H_5$ | H | $CH_3$ | $CH_3$ | $4\text{-}Br\text{—}C_6H_4CH_2$ |
| 187 | 6-Cl | 2-Cl | $C_2H_5$ | H | $CH_3$ | $CH_3$ | $2\text{-}F\text{—}C_6H_4CH_2$ |
| 188 | 6-Cl | 2-Cl | $C_2H_5$ | H | $CH_3$ | $CH_3$ | $3,4\text{-}Cl_2\text{—}C_6H_3CH_2$ |
| 189 | 6-Cl | 2-Cl | $C_2H_5$ | H | $CH_3$ | $CH_3$ | $3\text{-}CF_3\text{—}C_6H_4CH_2$ |
| 190 | 6-Cl | 2-Cl | $C_2H_5$ | H | $CH_3$ | $CH_3$ | $3,5\text{-}Cl_2\text{—}C_6H_3CH_2$ |
| 191 | 6-Cl | 2-Cl | $C_2H_5$ | H | $CH_3$ | $CH_3$ | $4\text{-}CF_3O\text{—}C_6H_5CH_2$ |
| 192 | 6-Cl | 2-Cl | $C_2H_5$ | H | $CH_3$ | $CH_3$ | $2\text{-}CF_3\text{—}C_6H_4CH_2$ |
| 193 | 6-Cl | 2-Cl | $C_2H_5$ | H | $CH_3$ | $CH_3$ | $4\text{-}CF_3\text{—}C_6H_4CH_2$ |
| 194 | 6-Cl | 2-Cl | $C_2H_5$ | H | $CH_3$ | $CH_3$ | $2\text{-}Br\text{—}C_6H_4CH_2$ |
| 195 | 6-Cl | 2-Cl | $C_2H_5$ | H | $CH_3$ | $CH_3$ | $2\text{-}Cl\text{—}C_6H_4CH_2$ |
| 196 | 6-Cl | 2-Cl | $C_2H_5$ | H | $CH_3$ | $CH_3$ | $2\text{-}CH_3\text{-}4\text{-}Cl\text{—}C_6H_3CH_2$ |
| 197 | 6-Cl | 2-Cl | $C_2H_5$ | H | $CH_3$ | $CH_3$ | $2\text{-}CH_3\text{-}5\text{-}F\text{—}C_6H_3CH_2$ |
| 198 | 6-Cl | 2-Cl | $C_2H_5$ | H | $CH_3$ | $CH_3$ | $3\text{-}Cl\text{—}C_6H_4CH_2$ |
| 199 | 6-Cl | 2-Cl | $C_2H_5$ | H | $CH_3$ | $CH_3$ | $Cl\text{-}n\text{-}C_3H_6$ |
| 200 | 6-Cl | 2-Cl | $C_2H_5$ | H | $CH_3$ | $CH_3$ | cyclopropyl |

TABLE 33

The compounds in Table 33 are of the general formula (1) where Ar is a group of the formula (C), n is 0 and the values of $A^4$, $A^5$, $R^1$, $R^2$, $R^3$, $R^4$ and $R^5$ are given in the table. The alkanoic acid amide side chain is attached to the 2-position of the pyridine ring in the group of the formula (C) (referred to as 2-pyridines).

| Compound No. | $A^4$ | $A^5$ | $R^1$ | $R^2$ | $R^3$ | $R^4$ | $R^5$ |
|---|---|---|---|---|---|---|---|
| 1 | H | 4-Cl | $CH_3$ | H | $CH_3$ | $CH_3$ | $CH_3$ |
| 2 | H | 4-Cl | $C_2H_5$ | H | $CH_3$ | $CH_3$ | $CH_3$ |
| 3 | H | 4-Cl | $CH_3$ | H | $CH_3$ | $CH_3$ | H |
| 4 | H | 4-Cl | $C_2H_5$ | H | $CH_3$ | $CH_3$ | H |
| 5 | H | 4-Cl | $CH_3$ | H | $CH_3$ | $CH_3$ | $C_2H_5$ |
| 6 | H | 4-Cl | $C_2H_5$ | H | $CH_3$ | $CH_3$ | $C_2H_5$ |
| 7 | 4-Cl | 6-Cl | $CH_3$ | H | $CH_3$ | $CH_3$ | $CH_3$ |
| 8 | 4-Cl | 6-Cl | $C_2H_5$ | H | $CH_3$ | $CH_3$ | $CH_3$ |
| 9 | 4-Cl | 6-Cl | $CH_3$ | H | $CH_3$ | $CH_3$ | H |
| 10 | 4-Cl | 6-Cl | $C_2H_5$ | H | $CH_3$ | $CH_3$ | H |
| 11 | 4-Cl | 6-Cl | $CH_3$ | H | $CH_3$ | $CH_3$ | $C_2H_5$ |
| 12 | 4-Cl | 6-Cl | $C_2H_5$ | H | $CH_3$ | $CH_3$ | $C_2H_5$ |
| 13 | H | H | $CH_3$ | H | $CH_3$ | $CH_3$ | $CH_3$ |
| 14 | H | H | $C_2H_5$ | H | $CH_3$ | $CH_3$ | $CH_3$ |
| 15 | H | H | $CH_3$ | H | $CH_3$ | $CH_3$ | H |
| 16 | H | H | $C_2H_5$ | H | $CH_3$ | $CH_3$ | H |
| 17 | 3-CN | 6-$CH_3$ | $CH_3$ | H | $CH_3$ | $CH_3$ | $CH_3$ |
| 18 | 3-CN | 6-$CH_3$ | $C_2H_5$ | H | $CH_3$ | $CH_3$ | $CH_3$ |
| 19 | 3-CN | 6-$CH_3$ | $CH_3$ | H | $CH_3$ | $CH_3$ | H |
| 20 | 3-CN | 6-$CH_3$ | $C_2H_5$ | H | $CH_3$ | $CH_3$ | H |
| 21 | 4-$CF_3$ | 6-$CH_3$ | $CH_3$ | H | $CH_3$ | $CH_3$ | $CH_3$ |
| 22 | 4-$CF_3$ | 6-$CH_3$ | $C_2H_5$ | H | $CH_3$ | $CH_3$ | $CH_3$ |
| 23 | 4-$CF_3$ | 6-$CH_3$ | $CH_3$ | H | $CH_3$ | $CH_3$ | H |
| 24 | 4-$CF_3$ | 6-$CH_3$ | $C_2H_5$ | H | $CH_3$ | $CH_3$ | H |

Table 34

The compounds in Table 34 are of the general formula (1) where Ar is 6-benzothiazolyl (a group of the formula (D1), n is 0, $R_1$ is methyl, $R_2$ is H, $R_3$ and $R_4$ are both methyl and $R_5$ has the values given in Table 14. Thus there are 90 compounds in Table 34, Compound No. 1 having the same value of $R^5$ as Compound No. 1 in Table 14, Compound No. 2 having the same value of $R^5$ as Compound No. 2 in Table 14, and so on.

Table 35

Table 35 consists of 90 compounds of the general formula (1), where Ar is 6-benzothiazolyl, n is 0, $R_1$ is ethyl, $R_2$ is hydrogen, $R_3$ and $R_4$ are both methyl and $R_5$ has the values listed in Table 14. Thus compound 1 of Table 35 is the same as compound 1 of Table 34 except that in compound 1 of Table 35 $R_1$ is ethyl instead of methyl. Similarly, compounds 2 to 90 of Table 35 are the same as compounds 2 to 90 of Table 34, respectively, except that in the compounds of Table 35 $R_1$ is ethyl instead of methyl.

Table 36

Table 36 consists of 90 compounds of the general formula (1), where Ar is 5-benzothiazolyl, n is 0, $R_1$ is methyl, $R_2$ is hydrogen, $R_3$ and $R_4$ are both methyl and $R_5$ has the values listed in Table 14. Thus compound 1 of Table 36 is the same as compound 1 of Table 34 except that in compound 1 of Table 36 Ar is 5-benzothiazolyl instead of 6-benzothiazolyl. Similarly, compounds 2 to 90 of Table 36 are the same as compounds 2 to 90 of Table 34, respectively, except that in the compounds of Table 36 Ar is 5-benzothiazolyl instead of 6-benzothiazolyl.

Table 37

Table 37 consists of 90 compounds of the general formula (1), where Ar is 5-benzothiazolyl, n is 0, $R_1$ is ethyl, $R_2$ is hydrogen, $R_3$ and $R_4$ are both methyl and $R_5$ has the values listed in Table 14. Thus compound 1 of Table 37 is the same as compound 1 of Table 35 except that in compound 1 of Table 37 Ar is 5-benzothiazolyl instead of 6-benzothiazolyl. Similarly, compounds 2 to 90 of Table 37 are the same as compounds 2 to 90 of Table 35, respectively, except that in the compounds of Table 37 Ar is 5-benzothiazolyl instead of 6-benzothiazolyl.

Table 38

Table 38 consists of 90 compounds of the general formula (1), where Ar is 6-benzoxazolyl, n is 0, $R_1$ is methyl, $R_2$ is hydrogen, $R_3$ and $R_4$ are both methyl and $R_5$ has the values listed in Table 14. Thus compound 1 of Table 38 is the same as compound 1 of Table 34 except that in compound 1 of Table 38 Ar is 6-benzoxazolyl instead of 6-benzothiazolyl. Similarly, compounds 2 to 90 of Table 38 are the same as compounds 2 to 90 of Table 34, respectively, except that in the compounds of Table 38 Ar is 6-benzoxazolyl instead of 6-benzothiazolyl.

Table 39

Table 39 consists of 90 compounds of the general formula (1), where Ar is 6-benzoxazolyl, n is 0, $R_1$ is ethyl, $R_2$ is hydrogen, $R_3$ and $R_4$ are both methyl and $R_5$ has the values listed in Table 14. Thus compound 1 of Table 39 is the same as compound 1 of Table 35 except that in compound 1 of Table 39 Ar is 6-benzoxazolyl instead of 6-benzothiazolyl. Similarly, compounds 2 to 90 of Table 39 are the same as compounds 2 to 90 of Table 35, respectively, except that in the compounds of Table 39 Ar is 6-benzoxazolyl instead of 6-benzothiazolyl.

Table 40

Table 40 consists of 90 compounds of the general formula (1), where Ar is 5-benzoisoxazolyl, n is 0, $R_1$ is methyl, $R_2$ is hydrogen, $R_3$ and $R_4$ are both methyl and $R_5$ has the values listed in Table 14. Thus compound 1 of Table 40 is the same as compound 1 of Table 34 except that in compound 1 of Table 40 Ar is 5-benzoisoxazolyl instead of 6-benzothiazolyl. Similarly, compounds 2 to 90 of Table 40 are the same as compounds 2 to 90 of Table 34, respectively, except that in the compounds of Table 40 Ar is 5-benzoisoxazolyl instead of 6-benzothiazolyl.

Table 41

Table 41 consists of 90 compounds of the general formula (1), where Ar is 5-(2,1,3-benzoxadiazolyl), n is 0, $R_1$ is methyl, $R_2$ is hydrogen, $R_3$ and $R_4$ are both methyl and $R_5$ has the values listed in Table 14. Thus compound 1 of Table 41 is the same as compound 1 of Table 34 except that in compound 1 of Table 41 Ar is 5-(2,1,3)-benzoxadiazolyl instead of 6-benzothiazolyl. Similarly, compounds 2 to 90 of Table 41 are the same as compounds 2 to 90 of Table 34, respectively, except that in the compounds of Table 41 Ar is 5-(2,1,3-benzoxadiazolyl) instead of 6-benzothiazolyl.

Table 42

Table 42 consists of 90 compounds of the general formula (1), where Ar is 2-chloro-6-benzothiazolyl, n is 0, $R_1$ is methyl, $R_2$ is hydrogen, $R_3$ and $R_4$ are both methyl and $R_5$ has the values listed in Table 14. Thus compound 1 of Table 42 is the same as compound 1 of Table 34 except that in compound 1 of Table 42 Ar is 2-chloro-6-benzothiazolyl instead of 6-benzothiazolyl. Similarly, compounds 2 to 90 of Table 42 are the same as compounds 2 to 90 of Table 34, respectively, except that in the compounds of Table 42 Ar is 2-chloro-6-benzothiazolyl instead of 6-benzothiazolyl.

Table 43

Table 43 consists of 90 compounds of the general formula (1), where Ar is 2-bromo-6-benzothiazolyl, n is 0, $R_1$ is methyl, $R_2$ is hydrogen, $R_3$ and $R_4$ are both methyl and $R_5$ has the values listed in Table 14. Thus compound 1 of Table 43 is the same as compound 1 of Table 34 except that in compound 1 of Table 43 Ar is 2-bromo-6-benzothiazolyl instead of 6-benzothiazolyl. Similarly, compounds 2 to 90 of Table 43 are the same as compounds 2 to 90 of Table 34, respectively, except that in the compounds of Table 43 Ar is 2-bromo-6-benzothiazolyl instead of 6-benzothiazolyl.

Table 44

Table 44 consists of 90 compounds of the general formula (1), where Ar is 2-methyl-amino-6-benzothiazolyl, n is 0, $R_1$ is methyl, $R_2$ is hydrogen, $R_3$ and $R_4$ are both methyl and $R_5$ has the values listed in Table 14. Thus compound 1 of Table 44 is the same as compound 1 of Table 34 except that in compound 1 of Table 44 Ar is 2-methylamino-6-benzothiazolyl instead of 6-benzothiazolyl. Similarly, compounds 2 to 90 of Table 44 are the same as compounds 2 to 90 of Table 34, respectively, except that in the compounds of Table 44 Ar is 2-methylamino-6-benzothiazolyl instead of 6-benzothiazolyl.

Table 45

Table 45 consists of 90 compounds of the general formula (1), where Ar is 1-methyl-5-indazolyl, n is 0, $R_1$ is methyl, $R_2$ is hydrogen, $R_3$ and $R_4$ are both methyl and $R_5$ has the values listed in Table 14. Thus compound 1 of Table 45 is the same as compound 1 of Table 34 except that in compound 1 of Table 45 Ar is 5-1-methylindazolyl instead of 6-benzothiazolyl. Similarly, compounds 2 to 90 of Table 45 are the same as compounds 2 to 90 of Table 34, respectively, except that in the compounds of Table 45 Ar is 1-methyl-5-indazolyl instead of 6-benzothiazolyl.

Table 46

Table 46 consists of 90 compounds of the general formula (1), where Ar is 2-methyl-5-indazolyl, n is 0, $R_1$ is methyl, $R_2$ is hydrogen, $R_3$ and $R_4$ are both methyl and $R_5$ has the values listed in Table 14. Thus compound 1 of Table 46 is the same as compound 1 of Table 34 except that in compound 1 of Table 46 Ar is 5-2-methylindazolyl instead of 6-benzothiazolyl. Similarly, compounds 2 to 90 of Table 46 are the same as compounds 2 to 90 of Table 34, respectively, except that in the compounds of Table 46 Ar is 2-methyl-5-indazolyl instead of 6-benzothiazolyl.

Table 47

Table 47 consists of 90 compounds of the general formula (1), where Ar is 2-methyl-5-benzothiazolyl, n is 0, $R_1$ is methyl, $R_2$ is hydrogen, $R_3$ and $R_4$ are both methyl and $R_5$ has the values listed in Table 14. Thus compound 1 of Table 47 is the same as compound 1 of Table 34 except that in compound 1 of Table 47 Ar is 2-methyl-5-benzothiazolyl instead of 6-benzothiazolyl. Similarly, compounds 2 to 90 of Table 47 are the same as compounds 2 to 90 of Table 34, respectively, except that in the compounds of Table 47 Ar is 2-methyl-5-benzothiazolyl instead of 6-benzothiazolyl.

Tables 48 to 94

Tables 48 to 94 correspond exactly to Tables 1 to 47 (i.e. Table 48 corresponds exactly to Table 1, Table 49 corresponds exactly to Table 2, and so on) the only difference being that in each of Tables 48 to 94 n is 1 instead of 0.

Tables 95 to 141

Tables 95 to 141 correspond exactly to Tables 1 to 47 (i.e. Table 95 corresponds exactly to Table 1, Table 96 corresponds where Hal is a halogen atom such as bromine, chlorine or iodine, by reaction with a halogenating agent such as N-bromosuccinimide, in a suitable solvent such as carbon tetrachloride or acetonitrile, in the presence of a radical initiator such as AIBN (azo-isobutyronitrile), and a light source, at between ambient temperature and the reflux temperature of the solvent. Compounds of general formula (3) are then reacted with alkanethiols of general formula $R^1SH$, in the presence of a base such as sodium hydride, in a suitable solvent such as DMF, to give compounds of general formula (6), or are reacted with alkanethiol salts $R^1S^-M^+$, where M is a metal such as sodium or lithium, in a suitable solvent such as DMF, to give compounds of general formula (6).

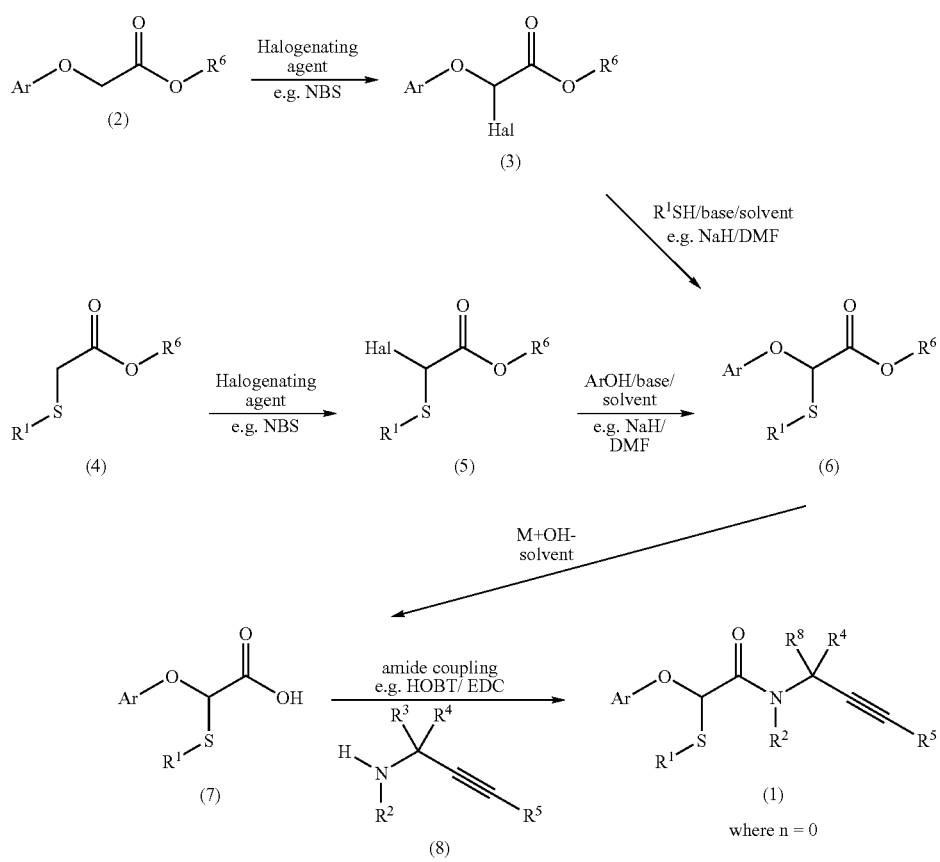

exactly to Table 2, and so on) the only difference being that in each of Tables 95 to 141 n is 2 instead of 0.

The compounds of general formula (1) may be prepared as outlined in Schemes 1 to 4 below, in which Ar, $R^1$, $R^2$, $R^3$, $R^4$ and $R^5$ have the meanings given above, $R^6$ is H or $C_{1-4}$ alkyl, as indicated, $R^a$ is H or $C_{1-3}$ alkyl, $R^b$ is H or $C_{1-3}$ alkyl, provided that when $R^a$ and $R^b$ are both alkyl their total number of carbon atoms does not exceed 3, $R^c$ is $C_{1-6}$ alkyl, optionally substituted benzyl or optionally substituted thienylmethyl, DMF is N,N-dimethylformamide, NBS is N-bromosuccinimide, NCS is N-chlorosuccinimide and MCPBA is m-chloroperbenzoic acid. Other abbreviations are defined in the text.

Compounds of formula (1), where n is 0, may be prepared as shown in Scheme 1. Esters of formula (2), where $R^6$ is $C_{1-4}$ alkyl, may be halogenated to give haloesters of formula (3), Alternatively esters of general formula (4) are halogenated to give haloesters of formula (5), where Hal is a halogen atom such as bromine, chlorine or iodine, by reaction with a halogenating agent such as N-chlorosuccinimide or N-bromosuccinimide, in a suitable solvent such as carbon tetrachloride or acetonitrile, at between 0° C. and the reflux temperature of the solvent. Haloesters of formula (5) are reacted with hydroxy (hetero)aryls ArOH, where Ar is as defined above, in the presence of a base such as potassium t-butoxide, potassium carbonate, or sodium hydride in a suitable solvent such as t-butanol, 1,4-dioxane or DMF, at between ambient temperature and the reflux temperature of the solvent, to give compounds of formula (6). Compounds of formula (6) are hydrolysed to acids of formula (7) by reaction with an alkali metal hydroxide $M^+OH^-$, in a suitable solvent such as aqueous methanol, ethanol, or THF (tetrahydrofuran) at between ambient temperature and the reflux temperature of the solvent. Acids of formula (7) can be condensed with amines of formula (8), using suitable activating agents such as HOBT (1-hydroxybenzotriazole) and EDC (1-ethyl-3-N,N-dimethylaminopropyl-carbodiimide hydrochloride), at between 0° C. and ambient temperature, to give compounds of general formula (1) where n is 0.

Compounds of general formula (1), where n is 1 or 2, are prepared by oxidation to the sulphoxide (n is 1) or sulphone (n is 2) oxidation state, as shown in Scheme 2. For example, esters of the general formula (6) can be oxidised to sulphoxides of formula (9) with an oxidising agent such as sodium periodate in a suitable solvent such ethanol, between 0° C. and ambient temperature. Sulphones of formula (10) can be made either directly from compounds of formula (6) with two or more equivalents of an oxidising agent such as m-chloroperbenzoic acid (MCPBA), in a suitable solvent such as dichloromethane between 0° C. and the reflux temperature of the solvent, or from sulphoxides of formula (9) with one or more equivalents of m-chloroperbenzoic acid. Sulphides of formula (6), sulphoxides of formula (9) or sulphones of formula (10) can be hydrolysed to the corresponding acids (7), (11) or (12) by reaction with an alkali metal hydroxide in a suitable solvent such as ethanol at between 0° C. and the reflux temperature of the solvent followed by acidification. The acids of formula (7), (11) or (12) can be condensed with amines of formula (8), using suitable activating agents such as HOBT and EDC, at between 0° C. and ambient temperature, to give compounds of general formula (1) where n is 0, 1 or 2.

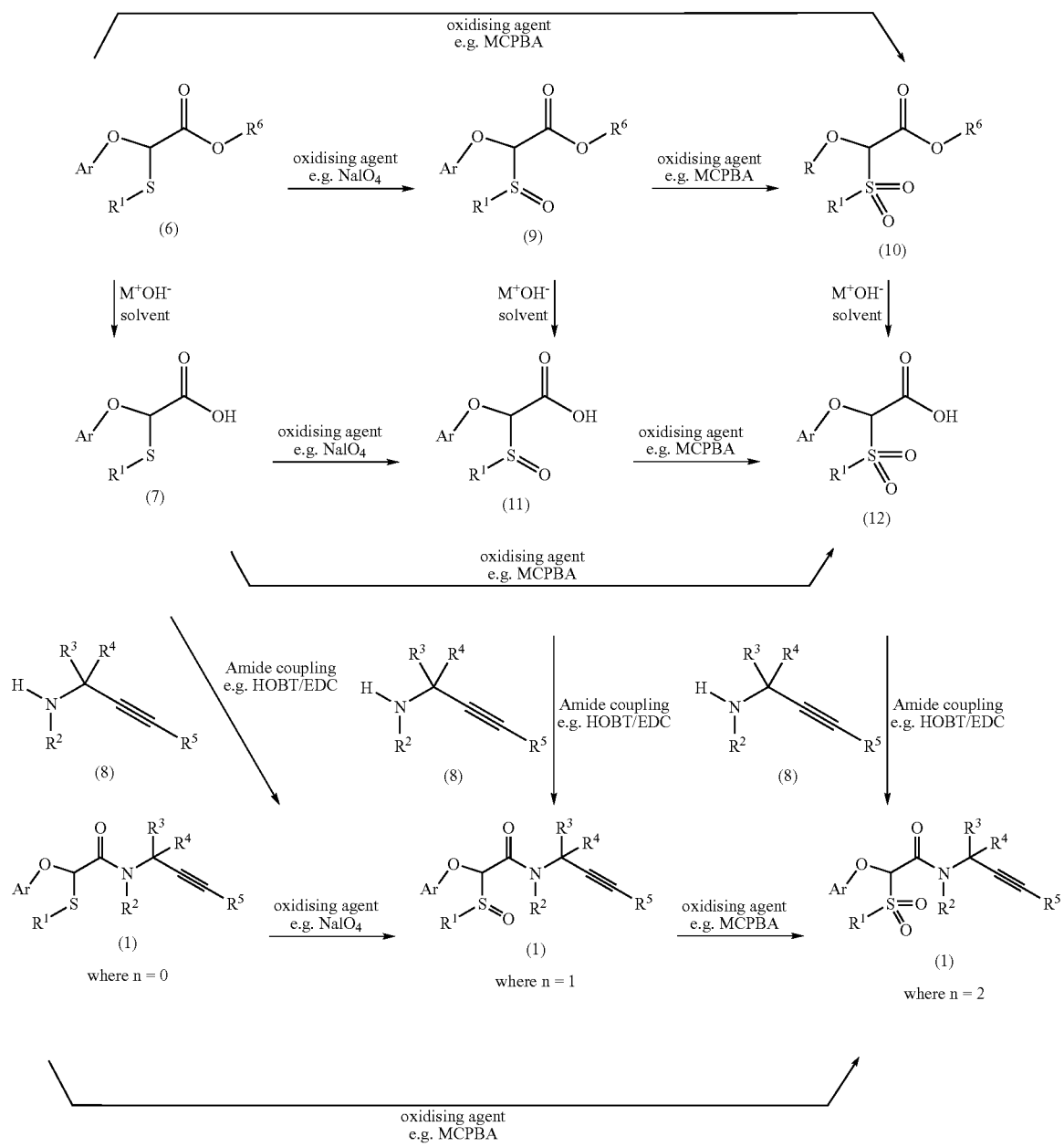

Similarly, sulphoxides of formula (11) and of formula (1) where n is 1 can be prepared from sulphides of formula (7) and of formula (1) where n is 0 respectively, using oxidising agents such as sodium metaperiodate or m-chloroperbenzoic acid as described above. Sulphones of formula (12) and of formula (1) where n is 2, can be prepared either from sulphides of formula (7) and of formula (1) where n is 0, by using at least two equivalents of oxidising agents such as m-chloroperbenzoic acid, or from sulphoxides of formula (11) and of formula (1) where n is 1, using one or more equivalents of oxidising agents such as m-chloroperbenzoic acid, as described above.

Compounds of formula (1) can also be prepared as shown in Scheme 3. Acids of formula (13) can be condensed with amines of formula (8), using suitable activating agents such as HOBT and EDC, at between 0° C. and ambient temperature, to give compounds of formula (14). Compounds of formula (14) can be halogenated to compounds of formula (16) using a halogenating agent such as N-chlorosuccinimide, in a suitable solvent such as carbon tetrachloride or acetonitrile, at between 0° C. and ambient temperature. Amides of formula (16) can also be prepared from acid halides of formula (15) by reaction with amines of formula (8) in the presence of a base such as triethylamine in a suitable solvent such as dichloromethane, at between 0° C. and ambient temperature.

As shown in Scheme 4, amines of the general formula (20), which are examples of amines of the general formula (8) wherein $R^2$ is H, may be prepared by alkylation of a silyl-protected aminoalkyne of the general formula (18) using a suitable base, such as n-butyl lithium, followed by reaction with a suitable alkylating reagent $R^5LG$, such as an alkyl iodide, for example, methyl iodide, to form an alkylated compound of the general formula (19). In a similar procedure, a silyl-protected aminoalkyne of the general formula (18) may be reacted with a carbonyl derivative $R^aCOR^b$, for example formaldehyde, using a suitable base, such as n-butyl lithium, to provide an aminoalkyne (19) containing a hydroxyalkyl moiety. The silyl protecting group may then be removed from a compound of the general formula (19) with, for example, an aqueous acid to form an aminoalkyne of the general formula (20). Aminoalkynes of the general formula (20) may be further derivatised, for instance when $R^5$ is a hydroxyalkyl group, for example, by reacting a compound of the general formula (20) with a silylating agent, for example t-butyldimethylsilyl chloride, to give a derivative silylated on oxygen of the general formula (21). In addition, a compound of the general formula (20) may be treated with a base, such as sodium hydride or potassium bis(trimethylsilyl)amide followed by a compound $R^cLG$, to give a compound of the

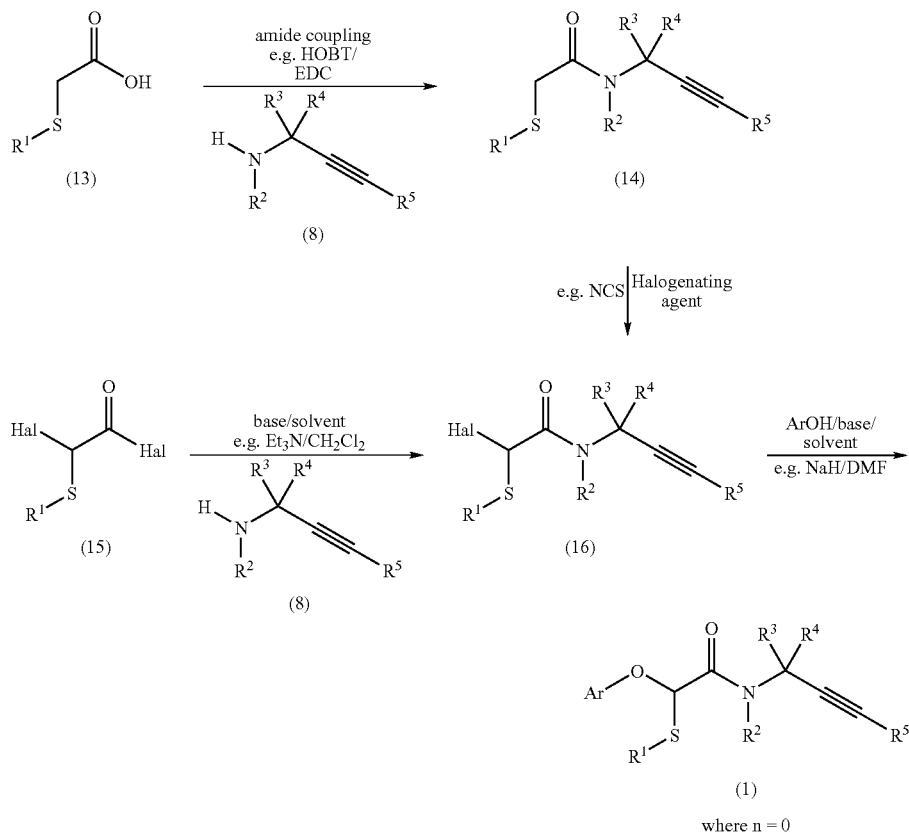

Halosulphides of formula (16) can be reacted with hydroxy (hetero)aryls ArOH, in the presence of a base such as potassium carbonate or sodium hydride, in a suitable solvent such as DMF, at between 0° C. and 80° C., to give compounds of formula (1) where n is 0.

general formula (22). In an alternative sequence, a compound of general formula (19) may be treated with a base, such as sodium or potassium bis(trimethylsilyl)amide, followed by a compound $R^cLG$, where LG represents a leaving group such as a halogen, or sulphonate ester such as $OSO_2Me$, or $OSO_2$-

4-tolyl, for example ethyl iodide, to give, after removal of the silyl protecting group, compounds of general formula (22).

wheat and other *Pyricularia* spp. on other hosts; *Puccinia triticina* (or *recondita*), *Puccinia striiformis* and other rusts

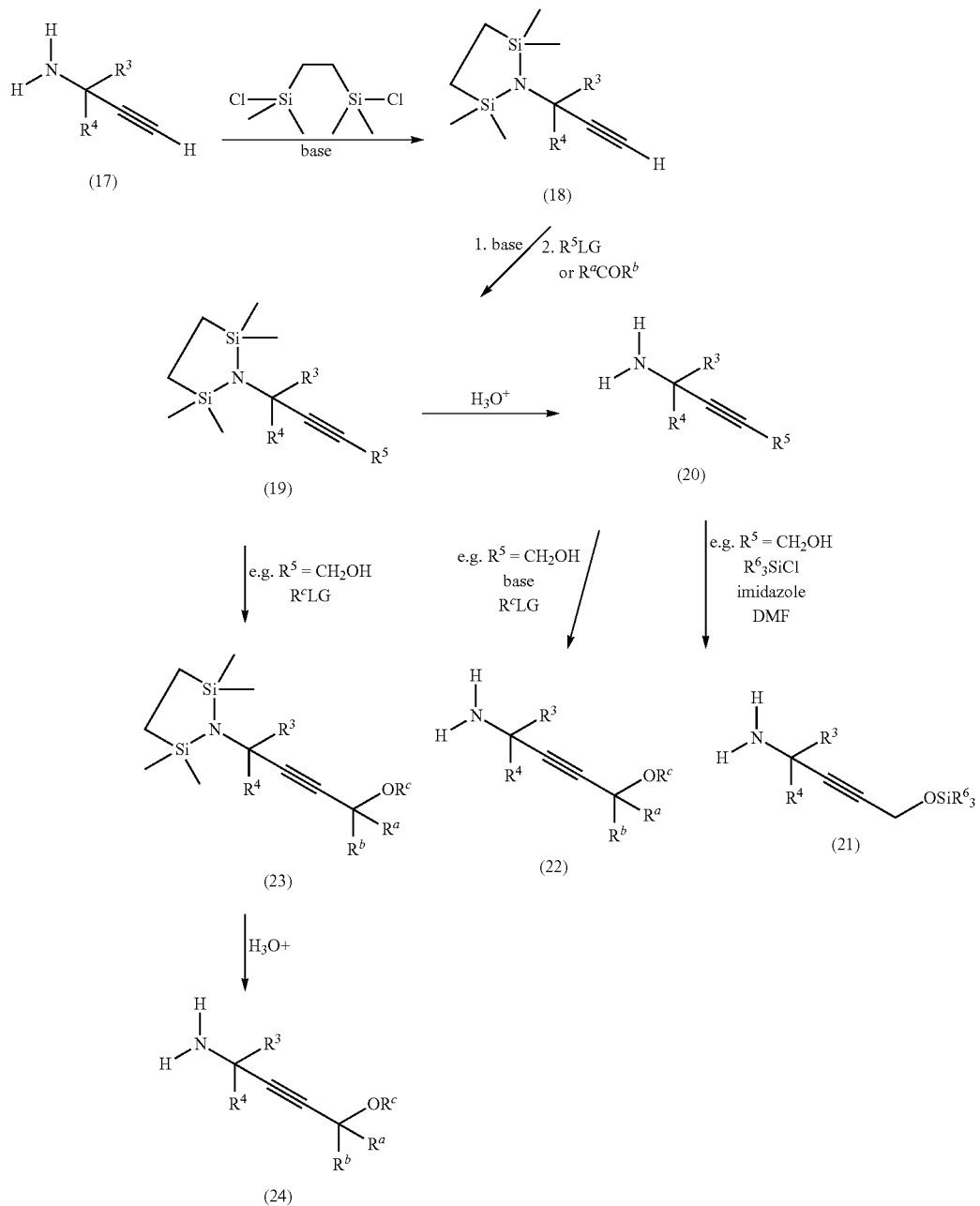

Scheme 4

Silyl-protected aminoalkynes of the general formula (18) may be obtained by reacting amines of general formula (17) with 1,2-bis-(chlorodimethylsilyl)ethane in the presence of a suitable base, such as a tertiary organic amine base, for example, triethylamine.

Amines of the general formula (17) are either commercially available or may be prepared by standard literature methods (see, for example, EP-A-0834498).

The compounds of formula (1) are active fungicides and may be used to control one or more of the following pathogens: *Pyricularia oryzae* (*Magnaporthe grisea*) on rice and on wheat, *Puccinia hordei*, *Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphiaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryospiraeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean; melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostomna piceae, Penicillium* spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

The compounds of formula (1) show particularly good activity against the Oomycete class of pathogens such as *Phytophthora infestans, Plasmopara* species, e.g. *Plasmopara viticola* and *Pythium* species e.g. *Pythium ultimum*.

A compound of formula (1) may move acropetally, basipetally or locally in plant tissue to be active against one or more fungi. Moreover, a compound of formula (1) may be volatile enough to be active in the vapour phase against one or more fungi on the plant.

The invention therefore provides a method of combating or controlling phytopathogenic fungi which comprises applying a fungicidally effective amount of a compound of formula (1), or a composition containing a compound of formula (1), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (1) are preferably used for agricultural, horticultural and turfgrass purposes in the form of a composition.

In order to apply a compound of formula (1) to a plant, to a seed of a plant, to the locus of the plant or seed or to soil or any other growth medium, a compound of formula (1) is usually formulated into a composition which includes, in addition to the compound of formula (1), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (1). The composition is generally used for the control of fungi such that a compound of formula (1) is applied at a rate of from 0.1 g to 10 kg per hectare, preferably from 1 g to 6 kg per hectare, more preferably from 1 g to 1 kg per hectare.

When used in a seed dressing, a compound of formula (1) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (1) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (1).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/ smoke formulations, capsule suspensions (CS) and seed treatment formulations. The formulation type chosen in any instance will depend upon the particular purpose envisaged and the physical, chemical and biological properties of the compound of formula (1).

Dustable powders (DP) may be prepared by mixing a compound of formula (1) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (1) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (1) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (1) and one or more powdered solid diluents or carriers, or from pre-formed blank granules by absorbing a compound of formula (1) (or a solution thereof, in a suitable agent) in a porous granular material (such as pumice, attapulgite clays, fuller's earth, kieselguhr, diatomaceous earths or ground corn cobs) or by adsorbing a compound of formula (1) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (1) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (1) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octyl-pyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (1) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (1) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (1). SCs may be prepared by ball or bead milling the solid compound of formula (1) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (1) may be dry milled and added to water, containing agents hereinbefore described, to produce the desired end product.

Aerosol formulations comprise a compound of formula (1) and a suitable propellant (for example n-butane). A compound of formula (1) may also be dissolved or dispersed in a suitable medium (for example water or a water miscible liquid, such as n-propanol) to provide compositions for use in non-pressurised, hand-actuated spray pumps.

A compound of formula (1) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (1) and, optionally, a carrier or diluent therefor. The polymeric shell may be produced by either an interfacial polycondensation reaction or by a coacervation procedure. The compositions may provide for controlled release of the compound of formula (1) and they may be used for seed treatment. A compound of formula (1) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (1)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (1)).

A compound of formula (1) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuc-cinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (1) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (1) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (1) (for example 0.0001 to 10%, by weight) depending upon the purpose for which they are to be used.

A compound of formula (1) may be used in mixtures with fertilisers (for example nitrogen-, potassium- or phosphorus-containing fertilisers). Suitable formulation types include granules of fertiliser. The mixtures suitably contain up to 25% by weight of the compound of formula (1).

The invention therefore also provides a fertiliser composition comprising a fertiliser and a compound of formula (1).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (1) alone. Further the other fungicide may have a synergistic effect on the fungicidal activity of the compound of formula (1).

The compound of formula (1) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (1); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) propionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone; CGA 41396, CGA 41397, chinomethionate, chlorbenzthiazone, chlorothalonil, chlorozolinate, clozylacon, copper containing compounds such as copper oxychloride, copper oxyquino-late, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dichloran, diethofencarb, difenoconazole, difenzoquat, diflumetorim, O,O-di-iso-propyl-S-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N([methyl(methyl-thioethylideneaminooxy-carbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

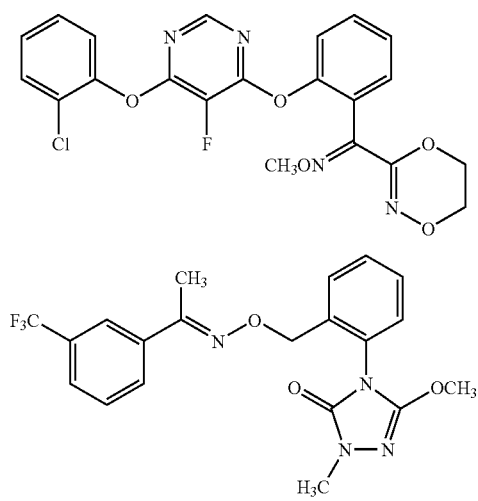

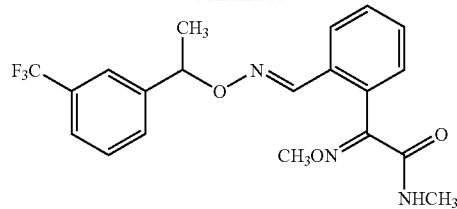

The compounds of formula (1) may be mixed with soil, peat or other rooting media for the protection of plants against seed-borne, soil-borne or foliar fungal diseases.

Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:
ml=millilitres m.p.=melting point (uncorrected)
g=grammes b.p.=boiling point
THF=tetrahydrofuran DMSO=dimethylsulphoxide
M⁺=mass ion DMF=N,N-dimethylformamide
s=singlet HOBT=1-hydroxybenzotriazole
d=doublet EDC=1-ethyl-3-N,N-dimethylamino propylcarbodiimide hydrochloride
bs=broad singlet NMR=nuclear magnetic resonance
t=triplet HPLC=high performance liquid chromatography
q=quartet TLC=thin layer chromatography
m=multiplet glc=gas-liquid chromatography
ppm=parts per million dec.=decomposition
M=molar

EXAMPLE 1

This Example illustrates the preparation of 2-(3,5-dichlorophenoxy)-2-(methylthio)-N-(2-methylpent-3-yn-2-yl)acetamide (Compound No. 4 of Table 1)
Step 1
t-Butyl 2-bromo-2-(3,5-dichlorophenoxy)acetate (1.0 g) was dissolved in 1,4-dioxane (3 ml), and sodium thiomethoxide (0.218 g) was added to the mixture. The resulting pale yellow suspension was stirred at ambient temperature for 5 hours and then stored for 18 hours. The solvent was evaporated, water was added and the aqueous layer was extracted twice with ethyl acetate (100 ml). The organic layers were combined, washed with brine, dried over magnesium sulphate, filtered and evaporated to give t-butyl 2-methylthio-2-(3,5-dichlorophenoxy)acetate as a pale yellow solid (0.80 g) which was used in the next step without further purification.
¹H NMR (CDCl₃) δ ppm: 1.52 (9H, s); 2.19 (3H, s), 5.39 (1H, s); 6.92 (2H, d); 7.04 (1H, t).
Step 2
To the product of Step 1 (0.2 g) in methanol (3 ml) at ambient temperature was added a solution of sodium hydroxide (0.050 g) in water (1 ml). The reaction was stirred for 2 hours, the solvent evaporated then water and ethyl acetate were added. The aqueous phase was separated, acidified with dilute aqueous hydrochloric acid then extracted with ethyl acetate. The organic phases were combined, dried over magnesium sulphate, filtered and evaporated to give 2-methylthio-2-(3,5-dichlorophenoxy)acetic acid as a pale yellow gum (0.153 g) that was used in the next step without further purification.

$^1$H NMR (CDCl$_3$) δ ppm: 2.21 (3H, s); 5.59 (1H, s); 6.95 (2H, s); 7.08 (1H, s).

Step 3

Triethylamine (0.1 ml) was added to a stirred solution of the 4-amino-4-methylpent-2-yne hydrochloride (0.077 g) in DMF (2 ml) giving a white suspension. The product from Step 2 (0.153 g) was added in DMF (1 ml) followed by the 1-hydroxybenzotriazole (HOBT, 0.078 g) and finally the N-(3-dimethylaminopropyl)-N'-ethyl carbodiimide hydrochloride (EDC, 0.110 g). The white suspension was stirred at ambient temperature for 1 hour, and stored for 18 hours. Water was added and the aqueous phase was extracted with ethyl acetate. The organic phases were combined, washed with water, dried over magnesium sulphate, filtered and evaporated to give a yellow solid (0.148 g), that was purified by flash column chromatography on silica gel eluting with 1:4 by volume ethyl acetate/hexane to give the title compound as a colourless solid (0.145 g), m.p. 120-122° C.

$^1$H NMR (CDCl$_3$) δ ppm: 1.68 (6H, s); 1.83 (3H, s); 2.16 (3H, s); 5.42 (1H, s); 6.58 (1H, bs); 6.94 (2H, d); 7.09 (1H, t).

4-Amino-4-methyl-pent-2-yne was prepared as follows:

Step 1

3-Amino-3-methylbutyne (commercially available as 90% aqueous solution; 16.6 g) was dissolved in dichloromethane (150 ml), dried over sodium sulphate and filtered to give a solution containing 14.9 g of amine. To the stirred solution of amine under an atmosphere of nitrogen at ambient temperature was added dry triethylamine (48.4 ml). 1,2-Bis-(chlorodimethylsilyl)ethane (38.98 g) in dichloromethane (100 ml) was then added dropwise, maintaining the reaction temperature at 15° C. by cooling. The mixture was stirred for 3 hours, the colourless solid, which had formed during the reaction, was filtered from solution and the filtrate was evaporated to give a paste. The paste was extracted into hexane and refiltered. The filtrate was evaporated and the oil obtained was distilled to give 1-(1,1-dimethyl-2-propynyl)-2,2,5,5-tetramethyl-1-aza-2,5-disilacyclopentane, (21.5 g), b.p. 41° C. at 0.06 mm Hg pressure.

$^1$H NMR (CDCl$_3$) δ ppm: 0.16 (12H, s); 0.60 (4H, s); 1.48 (6H, s); 2.24 (1H, s).

Step 2

The product from Step 1 (13.0 g) in dry THF (140 ml) was cooled to −70° C. under an atmosphere of nitrogen with stirring and a solution of n-butyl lithium (23.1 ml of 2.5M solution in hexanes) was added at −65 to −70° C. during 5 minutes. The mixture was allowed to warm to −5° C. and methyl iodide (3.93 ml) was added dropwise over 10 minutes. The reaction mixture was allowed to warm to 10° C. when an exothermic reaction occurred. The mixture was maintained at 20° C. by cooling for 2 hours then evaporated to a small volume. The residue was dissolved in hexane, filtered to remove the insoluble material and evaporated to give 1-(1,1-dimethyl-2-butynyl)-2,2,5,5-tetramethyl-1-aza-2,5-disilacyclopentane as a yellow oil, (13.0 g).

$^1$H NMR (CDCl$_3$) δ ppm: 0.10 (12H, s); 0.56 (4H, s); 1.40 (6H, s); 1.72 (3H, s).

Step 3

The product from Step 2 (13.0 g) was added slowly to aqueous hydrochloric acid (35 ml, 4M) at 0° C. with stirring. The emulsion formed was stirred for 0.5 hours then taken to pH14 with aqueous sodium hydroxide (4M) while maintaining the reaction mixture at 0° C. by cooling in ice. The aqueous mixture was extracted into dichloromethane (three times) and the extracts combined, dried over sodium sulphate and filtered. The filtrate was made acidic by adding an excess of a saturated solution of hydrogen chloride in 1,4-dioxan. The mixture was concentrated under reduced pressure until a colourless precipitate was formed. Hexane was added to the suspension and the solid was filtered from solution. The solid was washed with dry diethyl ether and placed under vacuum to remove any residual solvents to give 4-amino-4-methylpent-2-yne as a colourless solid, (5.0 g).

$^1$H NMR (d$_6$-DMSO) δ ppm: 1.74 (6H, s); 1.82 (3H, s); 8.74 (3H, broad signal).

In a similar procedure to Step 3 of Example 1, 2-(benzothiazoyl-6-oxy)-2-methylthioacetic acid was condensed with 1-chloro-6-methylhept-4-yn-6-ylamine hydrochloride to give 2-(benzothiazoyl-6-oxy)-2-methylthio-N-(1-chloro-6-methylhept-4-yn-6-yl) acetamide (Compound No. 90 of Table 34) as a yellow oil.

$^1$H NMR (CDCl$_3$) δ ppm: 1.68 (6H, s); 1.92-2.00 (2H, m); 2.20 (3H, s); 2.40 (2H, t); 3.66 (2H, t); 5.54 (1H, s); 6.72 (1H, s); 7.22-7.26 (1H, dd); 7.58 (1H, d); 8.09 (1H, d); 8.92 (1H, s).

In a similar procedure to Step 3 of Example 1, 2-(5-chloropyridyl-3-oxy)-2-methylthioacetic acid was condensed with 1-chloro-6-methylhept-4-yn-6-ylamine hydrochloride to give 2-(5-chloropyridyl-3-oxy)-2-methylthio-N-(1-chloro-6-methylhept-4-yn-6-yl) acetamide (Compound 149 of Table 31) as a colourless gum.

$^1$H NMR (CDCl$_3$) δ ppm: 1.04 (3H, t); 1.62 (6H, s); 1.92-2.04 (4H, m); 2.38-2.42 (2H, t); 3.68 (2H, t); 4.46 (1H, t); 6.30 (1H, s); 7.26 (1H, m); 8.28 (2H, m).

EXAMPLE 2

This Example illustrates the preparation of 2-(3,5-dichlorophenoxy)-2-(methanesulphinyl)-N-(2-methylpent-3-yn-2-yl) acetamide (Compound No. 4 of Table-48)

To a solution of 2-(3,5-dichlorophenoxy)-2-(methylthio)-N-(2-methylpent-3-yn-2-yl) acetamide (0.080 g) in dichloromethane (3 ml) at 0° C. was added portionwise m-chloroperbenzoic acid (0.077 g, 70% pure). The resulting white suspension was stirred at ambient temperature for 4-5 hours, then stored for 18 hours. The suspension was dissolved in more dichloromethane, washed with saturated aqueous sodium bicarbonate, dried and evaporated to give a colourless oil (0.20 g). This was purified by flash column chromatography on silica gel (40-60 mesh) eluting with ethyl acetate/hexane (1:1 to 2:1 volume), to give the title compound (0.064 g) as a 1:1 mixture of diastereoisomers: $^1$H NMR data is given for the mixture of diastereoisomers.

$^1$H NMR (CDCl$_3$) δ ppm: 1.62, 1.64, 1.65 (4×3H, 3s); 1.80 and 1.81 (2×3H, 2s); 2.67 and 2.77 (2×3H, 2s); 5.18 and 5.40 (2H, 2s); 6.64 and 6.82 (2H, 2bs); 6.98 and 7.06 (2×2H, 2s); 7.10 and 7.12 (2H, 2s).

EXAMPLE 3

This Example illustrates the preparation of 2-(3,5-dichlorophenoxy)-2-(methanesulphonyl)-N-(2-methylpent-3-yn-2-yl) acetamide (Compound No. 4 of Table 95)

To a solution of 2-(3,5-dichlorophenoxy)-2-(methylthio)-N-(2-methylpent-3-yn-2-yl) acetamide (0.042 g) in dichloromethane (2 ml) at 0° C. was added portionwise m-chloroperbenzoic acid (0.125 g, 70% pure). The resulting white suspension was stirred at ambient temperature for 4-5 hours and then stored for 18 hours. The suspension was dissolved in more dichloromethane, washed with saturated aqueous sodium bicarbonate solution, dried over magnesium sulphate then evaporated to give a colourless oil (0.070 g). This was purified by flash column chromatography on silica gel (40-60 mesh) eluting with ethyl acetate/hexane (1:2 by volume) to give the title compound as a colourless solid (0.026 g).

$^1$H NMR (CDCl$_3$) δ ppm: 1.66 (3H, s); 1.67 (3H, s); 1.82 (3H, s); 3.14 (3H, s); 5.27 (1H, s); 6.73 (1H, bs); 7.04 (2H, d); 7.15 (1H, t).

EXAMPLE 4

This Example illustrates the preparation of 2-(methylthio)-2-(quinolinyl-6-oxy)-N-(2-methylpent-3-yn-2-yl) acetamide (Compound No. 2 of Table 14)

Step 1

N-Bromosuccinimide (NBS, 4.37 g) and azo-isobutyronitrile (AIBN, catalytic amount) were added to ethyl 2-methylthioacetate (3.0 g) in carbon tetrachloride (20 ml) and stirred at ambient temperature for 2 hours. Further NBS was added (0.30 g) and the reaction stirred for a further 3 hours. The reaction mixture was filtered and the filtrate evaporated to give ethyl 2-bromo-2-methylthioacetate (6.5 g), that was used without further purification.

$^1$H NMR (CDCl$_3$) δ ppm: 1.30 (3H, s); 2.34 (3H, s); 4.26 (2H, q); 5.39 (1H, s).

Step 2

Potassium t-butoxide was dissolved in t-butanol (8 ml) and the mixture was stirred for 20 minutes at ambient temperature. The 6-hydroxyquinoline (1.5 g) was added and to the dark green solution was added the product from Step 1 (2.0 g). The reaction was stirred for 20 minutes and stored for 18 hours, then stirred for 5 hours. The mixture was poured into water, extracted with chloroform and the organic phase washed with brine, dried over magnesium sulphate, filtered then evaporated to give a dark brown oil (1.75 g). The oil was purified by flash column chromatography on silica gel (40-60 mesh) eluting with ethyl acetate/hexane (1:2 by volume), to give ethyl 2-methylthio-2-quinolin-6-oxyacetate as an orange oil (0.66 g).

$^1$H NMR (CDCl$_3$) δ ppm: 1.35 (3H, t); 2.25 (3H, s); 4.34 (2H, m); 5.73 (1H, s); 7.25 (1H, d); 7.39 (1H, dd); 7.51 (1H, dd); 8.05 (1H, m); 8.08 (1H, m); 8.82 (1H, dd).

Steps 3

In a similar procedure to Step 2 of Example 1, ethyl 2-methylthio-2-quinolin-6-oxyacetate was hydrolyzed to give 2-methylthio-2-quinolinyl-6-oxyacetic acid.

Step 4

In a similar procedure to Step 3 of Example 1, the acid from Step 3 was condensed with 4-amino-4-methyl-pent-2-yne hydrochloride to give the title compound.

$^1$H NMR (CDCl$_3$) δ ppm: 1.69 (3H, s); 1.70 (3H, s); 1.82 (3H, s); 2.22 (3H, s); 5.64 (1H, s); 6.76 (1H, s); 7.28 (1H, d); 7.40 (1H, dd); 7.47 (1H, dd); 8.09 (1H, m); 8.84 (1H, dd).

EXAMPLE 5

This Example illustrates the preparation of 2-(5-chloropyridyl-3-oxy)-2-(methylthio)-N-(2-methylpent-3-yn-2-yl) acetamide (Compound No. 3 of Table 31)

Step 1

5-Chloro-3-hydroxypyridine (1.30 g), ethyl 2-bromo-2-methylthioacetate (2.43 g, 70% pure) and anhydrous potassium carbonate (1.38 g) were stirred in dry DMF (15 ml) and heated to 80° C. with stirring for 1 hour. The mixture was cooled to ambient temperature, poured into water then extracted with diethyl ether (three times). The extracts were combined, washed with water, dried over magnesium sulphate then evaporated to give an oil, which was purified by flash chromatography on silica gel (40-60 mesh) eluting with hexane/ethyl acetate (1:1 by volume), to give ethyl 2-(5-chloropyridyl-3-oxy)-2-(methylthio)acetate as an orange oil (0.65 g).

$^1$H NMR (CDCl$_3$) δ ppm: 1.34-1.38 (3H, t); 2.20 (3H, s); 4.30-4.38 (2H, m); 5.58 (1H, s); 7.38 (1H, m); 8.30-8.32 (2H, d).

Step 2

The product from Step 1 (0.62 g) in THF (10 ml) and water (3 ml) containing sodium hydroxide (0.19 g) were stirred at 60° C. for 1.5 hours then cooled to ambient temperature and stored for 18 hours. The mixture was evaporated and the residue was diluted with water then washed with diethyl ether. The aqueous fraction was acidified with dilute hydrochloric acid and extracted with ethyl acetate. The extracts were combined, washed with water, dried over magnesium sulphate, then evaporated to give 2-(5-chloropyridyl-3-oxy)-2-(methylthio)acetic acid, 0.48 g, as a dark yellow gum.

$^1$H NMR (CDCl$_3$) δ ppm: 2.24 (3H, s); 5.72 (1H, s); 7.54 (1H, m); 8.34 (1H, s); 8.40 (1H, s); 9.52 (1H, bs).

Step 3

Triethylamine (0.40 ml) was added to a stirred solution of 4-amino-4-methyl-pent-2-yne hydrochloride (0.25 g) in DMF (10 ml) giving a white suspension. 2-(5-Chloropyridyl-3-oxy)-2-(methylthio)acetic acid (0.46 g) in dry DMF (10 ml) was added followed by HOBT (0.28 g) and EDC (0.40 g). The white suspension was stirred at ambient temperature for 3 hours then stored for 18 hours. The mixture was added to water and extracted with ethyl acetate. The extracts were combined, washed with water, dried over magnesium sulphate then evaporated to give a yellow gum. The gum was purified by flash column chromatography on silica gel (40-60 mesh) eluting with ethyl acetate/hexane (2:1 by volume) to give the title compound as a yellow gum (0.33 g).

$^1$H NMR (CDCl$_3$) δ ppm: 1.70 (6H, s); 1.84 (3H, s); 2.18 (3H, s); 5.48 (1H, s); 6.62 (1H, bs); 7.38 (1H, m); 8.30-8.32 (2H, m).

In a similar procedure to Step 3 of Example 5, 2-(3-bromoquinolinyl-6-oxy)-2-methylthioacetic acid was condensed with 4-amino-4-methyl-1-methoxypent-2-yne hydrochloride to give 2-(3-bromoquinolinyl-6-oxy)-2-(methylthio)-N-(5-methoxy-2-methylpent-3-yn-2-yl) acetamide (Compound No. 12 of Table 20) as a pale yellow oil.

$^1$H NMR (CDCl$_3$) δ ppm: 1.73 (6H, s); 2.21 (3H, s); 3.38 (3H, s); 4.12 (2H, s); 5.62 (1H, s); 6.72 (1H, s); 7.18 (1H, d); 7.74 (1H, dd); 8.06 (1H, d); 8.25 (1H, d); 8.82 (1H, d).

In a similar procedure to Step 3 of Example 5, 2-(5-chloropyridyl-3-oxy)-2-methylthioacetic acid was condensed with 4-amino-4-methyl-1-methoxypent-2-yne hydrochloride to give 2-(5-chloropyridyl-3-oxy)-2-methylthio-N-(5-methoxy-2-methylpent-3-yn-2-yl) acetamide (Compound No. 25 of Table 31) as an oil.

$^1$H NMR (CDCl$_3$) δ ppm: 1.73 (6H, s); 2.17 (3H, s); 3.38 (3H, s); 4.12 (2H, s); 5.50 (1H, s); 6.63 (1H, bs); 7.38 (1H, t); 8.31 (1H, d); 8.33 (1H, d).

In a similar procedure to Step 3 of Example 5, 2-(5-chloropyridyl-3-oxy)-2-methylthioacetic acid was condensed with 3-amino-3-methyl-butyne hydrochloride to give 2-(5-chloropyridyl-3-oxy)-2-methylthio-N-(2-methylbut-3-yn-2-yl) acetamide (Compound No. 2 of Table 31) as a pale brown solid.

¹H NMR (CDCl₃) δ ppm: 1.72 (6H, s); 2.18 (3H, s); 2.40 (1H, s); 5.52 (1H, s); 6.64 (1H, s); 7.38 (1H, m); 8.32 (2H, m).

EXAMPLE 6

This Example illustrates the preparation of 2-(5-bromopyridyl-3-oxy)-2-(methylthio)-N-(2-methylpent-3-yn-2-yl) acetamide (Compound No. 91 of Table 31)
Step 1
3,5-Dibromopyridine (30.0 g) was added to a stirred solution of sodium methoxide (prepared from 11.6 g of sodium) in methanol (120 ml) and heated to reflux for 70 hours under an atmosphere of nitrogen. The mixture was cooled to ambient temperature, poured into water (1000 ml), extracted with diethyl ether and the extracts combined, washed with water and dried over magnesium sulphate. The solvent was evaporated to give 3-bromo-5-methoxypyridine as a colourless liquid, which slowly crystallised on storing (19.3 g).
¹H NMR (CDCl₃) δ ppm: 3.86 (3H, s); 7.35-7.37 (1H, m); 8.24-8.30 (2H, m).
Step 2
The product from Step 1 (11.58 g) was mixed with aqueous hydrobromic acid (60 ml; 48% w/v) and heated to 120° C. for 48 hours with stirring. The mixture was cooled to ambient temperature, poured into water and made alkaline with aqueous sodium hydroxide (2M). The aqueous phase was extracted with diethyl ether and the organic extracts discarded. The aqueous phase was taken to pH 6-7 with concentrated hydrochloric acid and the precipitate that had formed was filtered from solution. The solid was washed with water and sucked to dryness under vacuum to give 5-bromo-3-pyridinol as a colourless solid, (8.67 g), m.p. 151-154° C.
¹H NMR (d₆-DMSO) δ ppm: 7.52-7.54 (1H, m); 8.22-8.30 (2H, m); 10.50-10.80 (1H, bs).
Step 3
In a similar procedure to Step 1 of Example 5, 5-bromo-3-pyridinol was reacted with ethyl 2-bromo-2-methylthioacetate to give ethyl 2-(5-bromopyridyl-3-oxy)-2-(methylthio) acetate as an orange oil.
¹H NMR (CDCl₃) δ ppm: 1.32-1.36 (3H, t); 2.20 (3H, s); 4.30-4.38 (2H, m); 5.58 (1H, s); 7.52 (1H, m); 8.34 (1H, s); 8.40 (1H, s).
Step 4
In a similar procedure to Step 2 of Example 5, ethyl 2-(5-bromopyridyl-3-oxy)-2-(methylthio)acetate was hydrolysed to give 2-(5-bromopyridyl-3-oxy)-2-(methylthio)-acetic acid as a yellow solid, m.p. 126-128° C. (dec).
¹H NMR (CDCl₃) δ ppm: 2.24 (3H, s); 5.72 (1H, s); 7.68 (1H, m); 8.42 (2H, bs); 9.28 (1H, bs).
Step 5
In a similar procedure to Step 3 of Example 5, 2-(5-bromopyridyl-3-oxy)-2-(methylthio)acetic acid was condensed with 4-amino-4-methyl-pent-2-yne to give the title compound as a yellow gum.
¹H NMR (CDCl₃) δ ppm: 1.68 (6H, s); 1.84 (3H, s); 2.18 (3H, s); 5.48 (1H, s); 6.62 (1H, bs); 7.52 (1H, m); 8.34 (1H, d); 8.42 (1H, m).

EXAMPLE 7

This Example illustrates the preparation of 2-(5-chloropyridyl-3-oxy)-2-(methanesulphinyl)-N-(2-methylpent-3-yn-2-yl) acetamide (Compound No. 3 of Table 78)
2-(5-Chloropyridyl-3-oxy)-2-(methylthio)-N-(2-methylpent-3-yn-2-yl) acetamide (0.10 g) in ethanol (4 ml) containing water (4 ml) was treated with sodium periodate (0.075 g) with stirring at ambient temperature. The mixture was stirred for 2 hours, stored for 18 hours, stirred for another 8 hours then further sodium periodate (0.045 g) was added and the reaction was stirred for 4 hours then stored for 18 hours. Further sodium periodate (0.005 g) was added and the mixture stirred for 4 hour then poured into water, extracted with ethyl acetate, washed with brine, dried over magnesium sulphate and evaporated to give the title compound as a gum (0.070 g). The NMR spectrum was consistent with the material containing a 1:1 mixture of diastereoisomers.
¹H NMR (CDCl₃) δ ppm: 1.66 (6H, s); 1.82 (3H, s); 2.70 (s) and 2.82 (s) total of 3H, 5.22 (s) and 5.46 (s) total of 1H, 6.68 (s) and 6.88 (s) total of 1H; 7.44 (m) and 7.5 (m) total of 1H, 8.36-8.42 (2H, m).

EXAMPLE 8

This Example illustrates the preparation of 2-(5-bromopyridyl-3-oxy)-2-(methanesulphonyl)-N-(2-methylpent-3-yn-2-yl) acetamide (Compound No. 91 of Table 125)
2-(5-Bromopyridyl-3-oxy)-2-(methylthio)-N-(2-methylpent-3-yn-2-yl) acetamide (0.114 g) in dichloromethane (5 ml) was stirred at ambient temperature and peracetic acid (0.1 ml, 36% wt/volume in acetic acid) was added. The mixture was stirred for 1.25 hours, further peracetic acid (0.05 ml, 36% wt/volume in acetic acid) was added and the reaction stirred for a further 1 hour. The mixture was evaporated and the residual gum was purified by flash column chromatography on silica gel (40-60 mesh) eluting with ethyl acetate/hexane (2:1 by volume) to give the title compound as a viscous, colourless gum (0.08 g).
¹H NMR (CDCl₃) δ ppm: 1.67 (3H, s); 1.68 (3H, s); 1.84 (3H, s); 3.18 (3H, s); 5.32 (1H, s); 6.82 (1H, s); 7.66 (1H, m); 8.44 (1H, s); 8.46 (1H, s).

EXAMPLE 9

This Example illustrates the preparation of 2-(5-chloro-3-pyridyloxy)-2-(methanesulphonyl)-N-(2-methylpent-3-yn-2-yl) acetamide N-oxide (Compound No. 139 of Table 125)
2-(5-Chloropyridyl-3-oxy)-2-(methylthio)-N-(2-methylpent-3-yn-2-yl) acetamide (0.11 g) in dichloromethane (5 ml) was cooled to 0° C. with stirring and 3-chloroperbenzoic acid (0.85 g, 60% peracid) was added in portions. On complete addition the mixture was stirred for 0.5 hours, stirred at ambient temperature for 1 hour then stored for 18 hours. The mixture was evaporated and the residue dissolved in ethyl acetate. The solution was washed with aqueous sodium hydrogen carbonate, brine and dried over magnesium sulphate then evaporated to give a yellow gum. The gum was purified by flash column chromatography on silica gel (40-60 mesh) eluting with ethyl acetate to give the title compound as a viscous gum (0.030 g).
¹H NMR (CDCl₃) δ ppm: 1.68 (6H, s); 1.82 (3H, s); 3.18 (3H, s); 5.50 (1H, s); 7.18 (1H, s); 7.24 (1H, s); 8.06 (1H, s); 8.24 (1H, s).

EXAMPLE 10

This Example illustrates the preparation of 2-(benzothiazolyl-6-oxy)-2-(methylthio)-N-(2-methylpent-3-yn-2-yl) acetamide (Compound No. 2 of Table 34)
Step 1
2-Amino-6-methoxybenzothiazole (9.0 g) in dry DMF (10 ml) was added dropwise over 35 minutes to a stirred solution of t-butyl nitrite (9.9 ml) in DMF (40 ml) at 65° C. The temperature of the mixture was kept <73° C. during the addition. On complete addition of the solution of benzothiazole, the dark red solution was stirred for an additional 15 minutes, cooled to ambient temperature then poured into dilute hydrochloric acid (200 ml) and diluted with brine. The dark red suspension was extracted with diethyl ether and the solid filtered then washed with further water and diethyl ether. The diethyl ether extracts were combined and the aqueous fraction re-extracted with ethyl acetate. The organic fractions were combined, washed with water and dried over magnesium sulphate then evaporated to give a brown solid. The solid was purified by flash column chromatography on silica gel (40-60 mesh) eluting with hexane/ethyl acetate (4:1 by volume) to give 6-methoxybenzothiazole as a colourless solid (2.1 g).

$^1$H NMR (CDCl$_3$) δ ppm: 3.89 (3H, s); 7.12 (1H, dd); 7.40 (1H, d); 8.01 (1H, d); 8.82 (1H, s).

Step 2

The product of Step 1 (1.2 g) in hydrobromic acid (10 ml, 48%) was heated at 120° C. with stirring for 6 hours then stored at ambient temperature for 2 days. The hot, pale yellow solution produced a suspension on cooling. The suspension was dissolved by the addition of water then the solution was adjusted to pH 6 by addition of sodium hydrogen carbonate and the solid that precipitated was filtered from solution, washed with water and sucked to dryness. The solid was dissolved in ethyl acetate, the solution dried over magnesium sulphate and evaporated to give 6-hydroxybenzothiazole as a colourless solid (1.05 g).

$^1$H NMR (CDCl$_3$) δ ppm: 7.07 (1H, dd); 7.91 (1H, d); 8.76 (1H, d); 9.18 (1H, s).

Step 3

The product of Step 2 (1.10 g), ethyl 2-bromo-2-methylthioacetate (2.22 g, 73% pure) and anhydrous potassium carbonate (2.0 g) were stirred in dry DMF (5 ml) at 80° C. for 0.5 hours then cooled to ambient temperature. The mixture was poured into saturated aqueous ammonium chloride, made acidic with dilute hydrochloric acid then extracted with diethyl ether. The extract was washed with water, dried over magnesium sulphate and evaporated to give a brown gum. The gum was purified by flash column chromatography on silica gel (40-60 mesh) eluting with hexane/ethyl acetate (1:1 by volume) to give ethyl 2-(benzothiazolyl-6-oxy)-2-(methylthio)acetate as a yellow solid (0.50 g).

$^1$H NMR (CDCl$_3$) δ ppm: 1.37 (3H, t); 2.27 (3H, s); 4.30-4.42 (2H, m); 5.65 (1H, s); 7.28 (1H, m); 7.59 (1H, m); 8.08 (1H, d); 8.90 (1H, s).

Step 4

To a stirred solution of the product of Step 3 (0.50 g) in THF (4 ml) was added a solution of lithium hydroxide monohydrate (0.076 g) in water (1 ml) at ambient temperature. After 1 hour, the mixture was made acidic with dilute sulphuric acid, extracted with diethyl ether and the extract was dried over magnesium sulphate then evaporated to give 2-(benzothiazolyl-6-oxy)-2-(methylthio)acetic acid as a pale yellow solid (0.45 g).

$^1$H NMR (CDCl$_3$) δ ppm: 2.28 (3H, s); 5.72 (1H, s); 7.28 (1H, dd); 7.60 (1H, m); 8.11 (1H, d); 8.99 (1H, s).

Step 5

A solution of 4-amino-4-methylpent-2-yne hydrochloride (0.252 g) in dry DMF (7 ml) was treated with triethylamine (0.525 ml) with stirring. 1-Hydroxybenzotriazole (0.27 g) was added to the suspension followed by 1-(3-dimethylaminopropyl)-3-ethylcarbodiimide hydrochloride (0.363 g) followed by a solution of the product of Step 4 (0.45 g) in dry DMF (3 ml). The reaction was stirred for 2 hours at ambient temperature, stored for 18 hours and brine was added then the mixture was extracted with diethyl ether. The extracts were combined, washed with water, dried over magnesium sulphate then evaporated to give a gum. The gum was fractionated by chromatography (silica; hexane/ethyl acetate, 1:1 by volume) to give the title compound as a pale yellow gum (0.42 g).

$^1$H NMR (CDCl$_3$) δ ppm: 1.78 (3H, s); 1.80 (3H, s); 1.82 (3H, s); 2.20 (3H, s); 5.54 (1H, s); 6.77 (1H, bs); 7.23 (1H, dd); 7.58 (1H, m); 8.09 (1H, d); 8.92 (1H, s).

EXAMPLE 11

This Example illustrates the preparation of 2-(benzothiazolyl-6-oxy)-2-(methanesulphinyl)-N-(2-methylpent-3-yn-2-yl) acetamide (Compound No. 2 of Table 81)

To a stirred solution of 2-(benzothiazolyl-6-oxy)-2-(methylthio)-N-(2-methyl-pent-3-yn-2-yl) acetamide (0.12 g) in ethanol (5 ml) was added a solution of sodium periodate (0.154 g) in water (5 ml) at ambient temperature. The mixture was stirred for 2 hours, stored for 18 hours, brine was added and the mixture extracted with ethyl acetate. The extract was washed with brine, dried over magnesium sulphate then evaporated to give the title compound as a colourless gum (0.090 g). The NMR spectrum was consistent with the material containing a 1:1 mixture of diastereoisomers.

$^1$H NMR (CDCl$_3$) δ ppm: 1.67 (3H, s); 1.69 (3H, s); 1.80 (s) and 1.82 (s) total of 3H, 2.72 (s) and 2.83 (s) total of 3H, 5.28 (s) and 5.53 (s) total of 1H, 6.81 (s) and 6.94 (s) total of 1H, 7.29 (dd) and 7.33 (dd) total of 1H, 7.67 (m) and 7.79 (m) total of 1H, 8.09 (m) and 8.94 (m) total of 1H.

EXAMPLE 12

This Example illustrates the preparation of 2-(benzothiazolyl-6-oxy)-2-(methylthio)-N-(5-methoxy-2-methylpent-3-yn-2-yl) acetamide (Compound No. 12 of Table 34)

Step 1

To a stirred solution of 2-(benzothiazolyl-6-oxy)-2-methylthioacetic acid (0.248 g) in dry dichloromethane (5 ml) was added oxalyl chloride (0.085 ml). The mixture was stirred for 1 hour at ambient temperature then evaporated to give 2-(benzothiazolyl-6-oxy)-2-methylthioacetyl chloride as a brown gum, which was used in the next Step without further purification.

$^1$H NMR (CDCl$_3$) δ ppm: 2.22 (3H, s); 5.82 (1H, s); 7.31 (1H, dd); 7.59 (1H, d); 8.20 (1H, d); 9.20 (1H, s).

Step 2

To a stirred solution of the product of Step 1 (0.123 g) in dry dichloromethane (5 ml) at ambient temperature was added 4-amino-4-methyl-1-methoxypent-2-yne hydrochloride (0.078 g) followed by dry triethylamine (0.13 ml). The brown solution was stirred at ambient temperature for 18 hours, diluted with dichloromethane and washed with water. The organic phase was dried over magnesium sulphate then evaporated to give a brown gum. The gum was fractionated by chromatography (silica; hexane/ethyl acetate, 1:1 by volume) to give the title compound as a pale brown gum (0.113 g).

$^1$H NMR (CDCl$_3$) δ ppm: 1.72 (3H, s); 1.73 (3H, s); 2.20 (3H, s); 3.39 (3H, s); 4.12 (2H, s); 5.56 (1H, s); 6.77 (1H, s); 7.22 (1H, dd); 7.58 (1H, m); 8.09 (1H, d); 8.92 (1H, s).

The 4-amino-4-methyl-1-methoxypent-2-yne hydrochloride was prepared as follows.

Step 1

1-(1,1-Dimethyl-2-propynyl)-2,2,5,5-tetramethyl-1-aza-2,5-disilacyclopentane (22.6 g) in dry THF (250 ml) was cooled to −50° C. under an atmosphere of nitrogen with stirring and a solution of n-butyl lithium (44 ml, 2.5M solution in hexanes) was added dropwise over 10 minutes. The mixture was stirred for 0.5 hour, allowed to warm to 20° C., then formaldehyde gas was bubbled through the mixture until no starting material remained, as determined by glc analysis. On complete reaction the mixture was treated with water, the ether phase separated and the aqueous phase was extracted with ethyl acetate (twice). The organic extracts were combined, washed with water (three times), dried over magnesium sulphate and evaporated to give 1-(1,1-dimethyl-4-hydroxy-2-butynyl)-2,2,5,5-tetramethyl-1-aza-2,5-disilacyclopentane as a pale yellow liquid (24.96 g).

$^1$H NMR (CDCl$_3$) δ ppm: 0.00 (12H, s); 0.46 (4H, s); 1.32 (6H, s); 4.10 (2H, s).

Step 2

The product from Step 1 (24.96 g) was treated with dilute aqueous hydrochloric acid (300 ml) and stirred at ambient temperature for 0.5 hour. The mixture was washed with diethyl ether (twice), the aqueous phase was evaporated, distilled with toluene (twice) to remove residual water and the residual solid obtained was triturated with hexane to give 4-amino-1-hydroxy-4-methylpent-2-yne hydrochloride as a cream coloured solid (13.1 g).

$^1$H NMR (CDCl$_3$) δ ppm: 1.48 (6H, s); 4.06 (2H, s); 5.32 (1H, s); 8.64 (3H, s).

Step 3

To a stirred suspension of sodium hydride (0.45 g, 80% dispersion in mineral oil) in dry DMF (2 ml) under an atmosphere of nitrogen at ambient temperature was added dropwise over 5 minutes a solution of the product of Step 2 (0.75 g) in dry DMF (20 ml). The mixture was stirred for 2.75 hours at ambient temperature then a solution of methyl iodide (0.78 g) in DMF (5 ml) was added. The reaction was stirred for 2.5 hours, stored for 18 hours then poured into water, extracted with diethyl ether (three times) and the organic extracts were combined. The combined organic phase was extracted with dilute hydrochloric acid (three times) and the aqueous acidic extracts were combined and evaporated. The residual solid was dried by evaporating it under reduced pressure with toluene (twice) to give 4-amino-4-methyl-1-methoxypent-2-yne hydrochloride as a yellow gum (0.8 g).

$^1$H NMR (CDCl$_3$) δ ppm: 1.78 (6H, s); 3.40 (3H, s); 4.12 (2H, s); 8.90 (3H, broad signal).

EXAMPLE 13

This Example illustrates the preparation of 2-(quinazolinyl-6-oxy)-2-methylthio-N-(2-methylpent-3-yn-2-yl) acetamide (Compound No. 2 of Table 16)

Step 1

Ethyl 2-bromo-2-methylthioacetate (0.93 g, 73% pure) was added dropwise to a stirred solution of 6-hydroxyquinazoline (0.447 g, preparation given in J. Chem. Soc. 1952, 4985) in dry DMF (5 ml) containing anhydrous potassium carbonate (0.845 g) heated to 80° C. On complete addition, the mixture was stirred for 0.5 hours, cooled to ambient temperature and stored for 2 days. The brown suspension was diluted with saturated aqueous ammonium chloride and extracted with ethyl acetate. The extracts were combined, washed with water, dried over magnesium sulphate and evaporated to give a red gum. The gum was fractionated by chromatography on silica gel (40-60 mesh), eluting with hexane/ethyl acetate (1:1 by volume) to give ethyl 2-(quinazolinyl-6-oxy)-2-methylthioacetate as a red gum (0.25 g).

$^1$H NMR (CDCl$_3$) δ ppm: 1.37 (3H, t); 2.25 (3H, s); 4.36 (2H, m); 5.75 (1H, s); 7.32 (1H, d); 7.71 (1H, dd); 8.02 (1H, d); 9.27 (1H, s); 9.33 (1H, s).

Step 2

To a stirred solution of the product from Step 1 (0.24 g) in THF (3 ml) at ambient temperature was added a solution of lithium hydroxide monohydrate (0.040 g) in water (1 ml). The mixture was stirred for 1 hour, acidified with dilute sulphuric acid and extracted with diethyl ether. The extracts were combined, washed with water, dried over magnesium sulphate and evaporated to give 2-(quinazolinyl-6-oxy)-2-methylthioacetic acid as a brown solid (0.074 g).

$^1$H NMR (D$_2$O) δ ppm: 2.18 (3H, s); 5.18 (1H, s); 7.47 (1H, m); 7.79 (1H, dd); 7.99 (1H, d); 9.08 (1H, s); 9.41 (1H, s).

Step 3

Triethylamine (0.086 ml) was added to a stirred solution of 4-amino-4-methyl-pent-2-yne hydrochloride (0.041 g) in dry DMF (3 ml) giving a white suspension. 1-HOBT (0.044 g) was added followed by EDC (0.060 g) then the product of Step 2 (0.074 g) in dry DMF (1 ml) was added. The white suspension was stirred at ambient temperature for 2 hours. The mixture was diluted with brine and extracted with ethyl acetate. The extracts were combined, washed with brine, dried over magnesium sulphate then evaporated to give a brown gum. The gum was fractionated by chromatography on silica gel (40-60 mesh) eluting with ethyl acetate/hexane (1:1 by volume) to give the title compound as a pale brown gum (0.09 g).

$^1$H NMR (CDCl$_3$) δ ppm: 1.70 (3H, s); 1.71 (3H, s); 1.82 (3H, s); 2.22 (3H, s); 5.65 (1H, s); 6.70 (1H, s); 7.37 (1H, m); 7.69 (1H, dd); 8.06 (1H, d); 9.28 (1H, s); 9.36 (1H, s).

EXAMPLE 14

This Example illustrates the preparation of 2-(3,5-dichlorophenoxy)-2-(methylthio)-N-(2-methylpent-3-yn-2-yl) acetamide (Compound No. 4 of Table 1) by an alternative route to that described in Example 1.

Step 1

Triethylamine (1.84 ml) was added to a stirred solution of 4-amino-4-methyl-pent-2-yne hydrochloride (1.278 g) in DMF (5 ml) giving a white suspension. Methylthioacetic acid (1.0 g) in DMF (5 ml) was then added to the amine followed by the HOBT (1.27 g) and finally EDC (1.806 g). The white suspension was stirred at ambient temperature for 6 hours, and stored for 18 hours. Water was added and the aqueous phase was extracted with diethyl ether. The organic phases were combined, washed with water and dried over magnesium sulphate then filtered and evaporated to give 2-(methylthio)-N-(2-methylpent-3-yn-2-yl) acetamide as a yellow orange solid (1.9 g).

$^1$H NMR (CDCl$_3$) δ ppm: 1.63 (6H, s); 1.82 (3H, s); 2.13 (3H, s); 3.14 (2H, s); 6.95 (NH, s).

Step 2

The product of Step 1 (0.824 g) was dissolved in carbon tetrachloride (15 ml) with warming. The solution was then cooled to 0° C. and N-chlorosuccinimide (NCS, 0.653 g) was then gradually added and the mixture was stirred at ambient temperature for 2 hours. The reaction mixture was filtered to remove succinimide and the resulting liquid was evaporated to give 2-(chloro)-2-(methylthio)-N-(2-methylpent-3-yn-2-yl) acetamide as a clear oil (1.4 g), which was used without further purification.

$^1$H NMR (CDCl$_3$) δ ppm: 1.64 (6H, s); 1.82 (3H, s); 2.29 (3H, s); 5.32 (1H, s); 6.57 (NH, s)

Step 3

To a stirred solution of 3,5-dichlorophenol (0.163 g) in DMF (8 ml) was added potassium carbonate (0.151 g), followed by the product of Step 2 (0.20 g). The reaction mixture was stirred for 1 hour at 80° C., cooled to ambient temperature and stored for 18 hours, then stirred for a further 3 hours at 80° C. Ethyl acetate was added and the mixture washed with water. The organic phase was separated, washed with water followed by dilute aqueous sodium hydroxide (10 ml), then the extract was dried over magnesium sulphate and evaporated to give an orange oil (0.350 g). This was purified by flash column chromatography on silica gel (40-60 mesh), eluting with ethyl acetate/hexane (1:4 by volume) to give the title compound as an orange solid (0.030 g).

In a similar procedure to Step 3 of Example 14, 6-hydroxybenzoxazole (preparation described in U.S. Pat. No. 6,130,217) was reacted with 2-chloro-2-methylthio-N-(2-methylpent-3-yn-2-yl)acetamide to give 2-(benzoxazoyl-6-oxy)-2-methylthio-N-(2-methylpent-3-yn-2-yl) acetamide (Compound No. 2 of Table 38) as a pale pink gum.

$^1$H NMR (CDCl$_3$) δ ppm: 1.70 (6H, s); 1.82 (3H, s); 2.20 (3H, s); 5.51 (1H, s); 6.76 (1H, s); 7.10 (1H, dd); 7.27 (1H, m); 7.72 (1H, d); 8.08 (1H, s).

EXAMPLE 15

This Example illustrates the preparation of single enantiomers of 2-(3,5-dichlorophenoxy)-2-methylthio-N-(2-methylpent-3-yn-2-yl) acetamide (Compound No. 4 of Table 1).

A racemic mixture of 2-(3,5-dichlorophenoxy)-2-methylthio-N-(2-methylpent-3-yn-2-yl) acetamide was separated into two single enantiomers by eluting the racemic mixture through a preparative chiral hplc column [Chiralpac AD (Daicel 5 cm×50 cm) with n-hexane/propan-2-ol (7:3 by volume). Optical rotations of the single enatiomers in propan-2-ol were measured. Isomer A +1.952° and isomer B −1.949°.

EXAMPLE 16

This Example illustrates the preparation of 2-(2,6-dichloro-4-pyridyloxy)-2-methylthio-N-(2-methylpent-3-yn-2-yl) acetamide (Compound No. 11 of Table 32)
Stage 1: Preparation of ethyl 2-(2,6-dichloro-4-pyridyloxy)-2-methylthioacetic acid In a similar procedure to Step 2 of Example 4,2,6-dichloro-4-hydroxypyridine was reacted with ethyl 2-bromo-2-methylthioacetate to give ethyl 2-(2,6-dichloro-4-pyridyloxy)-2-methylthioacetate as a pale yellow oil.

In a similar procedure to Step 2 of Example 5, ethyl 2-(2,6-dichloro-4-pyridyloxy)-2-methylthioacetate was hydrolysed to give 2-(2,6-dichloropyridyloxy)-2-methylthioacetic acid as a yellow gum.

$^1$H NMR (CDCl$_3$) δ ppm: 2.24 (3H, s); 5.69 (1H, s); 6.94 (2H, s).
Stage 2

In a similar procedure to Step 3 of Example 5, 2-(2,6-dichloro-4-pyridyloxy)-2-methylthioacetic acid was condensed with 4-amino-4-methylpent-2-yne to give 2-(2,6-dichloro-4-pyridyloxy)-2-methylthio-N-(2-methylpent-3-yn-2-yl) acetamide as a colourless solid, m.p. 141-142° C.

$^1$H NMR (CDCl$_3$) δ ppm: 1.67 (6H, s); 1.83 (3H, s); 2.20 (3H, s); 5.52 (1H, s); 6.46 (1H, s); 6.92 (2H, s).

EXAMPLE 17

This Example illustrates the preparation of 2-(3,5-dichlorophenoxy)-2-ethylthio-N-(2-methylpent-3-yn-2-yl) acetamide (Compound No. 4 of Table 2).
Step 1

In a similar procedure to Step 2 of Example 4,3,5-dichlorophenol was reacted with ethyl 2-bromo-2-ethylthioacetate (prepared from ethyl 2-ethylthioacetate in a similar procedure to the method described in Step 1 of Example 4 for ethyl 2-bromo-2-methylthioacetate) to give ethyl 2-(3,5-dichlorophenoxy)-2-ethylthioacetate as a yellow oil.

$^1$H NMR (CDCl$_3$) δ ppm: 1.20 (3H, t); 1.33 (3H, t); 2.75 (2H, m); 4.31 (2H, m); 5.55 (1H, s); 6.91 (2H, d); 7.05 (1H, t).
Step 2

In a similar procedure to Step 2 of Example 1, ethyl 2-(3,5-dichlorophenoxy)-2-ethylthioacetate was hydrolysed to give 2-(3,5-dichlorophenoxy)-2-ethylthioacetic acid as a gum.

$^1$H NMR (CDCl$_3$) δ ppm: 1.27 (3H, m); 2.80 (2H, m); 5.60 (1H, s); 6.93 (2H, d); 7.07 (1H, t).
Stage 2

In a similar procedure to Step 3 of Example 5, 2-(3,5-dichlorophenoxy)-2-ethylthioacetic acid was condensed with 4-amino-4-methylypent-2-yne hydrochloride to give 2-(3,5-dichlorophenoxy)-2-ethylthio-N-(2-methylpent-3-yn-2-yl) acetamide as a colourless solid.

$^1$H NMR (CDCl$_3$) δ ppm: 1.28 (3H, s); 1.66 (6H, s); 1.82 (3H, s); 2.27 (2H, m); 5.44 (1H, s); 6.54 (1H, s); 6.92 (2H, d); 7.08 (1H, m).

EXAMPLE 18

This Example illustrates the preparation of 2-(benzisoxazolyl-5-oxy)-2-methylthio-N-(2-methylpent-3-yn-2-yl) acetamide (Compound No. 2 of Table 40).

To a stirred solution of 5-hydroxybenzisoxazole (0.15 g, preparation described in *J Heterocyclic Chem* (1986), 27, 897) in dry 1,4-dioxan (3 ml) was added sodium hydride (0.049 g, 60% dispersion in mineral oil). When the effervescence has ceased, a solution of 2-chloro-2-methylthio-N-(2-methylpent-3-yn-2-yl)acetamide (0.229 g) in 1,4-dioxan (2 ml) was added and the mixture stirred at ambient temperature for 8 hours then stored for 2 days. The mixture was poured into dilute aqueous hydrochloric acid and extracted with diethyl ether. The organic phase was separated, washed with water, dried over magnesium sulphate and evaporated under reduced pressure to give a brown gum that was fractionated by chromatography (silica; CHCl$_3$/MeOH, 9:1 by volume) to give 2-(benzisoxazolyl-5-oxy)-2-methylthio-N-(2-methylpent-3-yn-2-yl) acetamide as a brown gum, 0.053 g.

$^1$H NMR (CDCl$_3$) δ ppm: 1.68 (3H, s); 1.69 (3H, s); 1.82 (3H, s); 2.20 (3H, s); 5.46 (1H, s); 6.63 (1H, s); 6.88 (1H, m); 7.11 (1H, dd); 7.71 (1H, d); 9.02 (1H, s).

EXAMPLE 19

This Example illustrates the preparation of 2-(3,8-dibromoquinolinyl-6-oxy)-2-methylthio-N-(2-methylpent-3-yn-2-yl) acetamide (Compound No. 2 of Table 26)
Stage 1: Preparation of 3,8-dibromo-6-hydroxyquinoline
Step 1: Preparation of 6-amino-3,8-dibromoquinoline 3,8-Dibromo-6-nitroquinoline (48.5 g, prepared as described in *J Am Chem Soc* (1955), 77, 4175-4176) was suspended in concentrated hydrochloric acid (400 ml) at ambient temperature and iron powder (27 g, reduced by hydrogen) was added in portions allowing the reaction temperature to rise to 73° C. during the additions. The bright yellow suspension that was initially produced became dark brown during the final stages of the reaction. The mixture was cooled to 0° C. and basified with aqueous sodium hydroxide (10M) until the reaction was at pH10. Ethyl acetate was added to the suspension and the mixture was thoroughly mixed then filtered through a bed of kieselguhr. The organic fraction was separated and the aqueous fraction re-extracted with further ethyl acetate. The insoluble material that was filtered from solution was further extracted with hot acetone and the organic fractions combined, washed with aqueous sodium hydrogen carbonate, dried over sodium sulphate and evaporated under reduced pressure to give 6-amino-3,8-dibromo-quinoline as a brown solid, 34.7 g.

$^1$H NMR (CDCl$_3$) δ ppm: 4.09 (2H, s); 6.76 (1H, s); 7.52 (1H, s); 8.03 (1H, s); 8.71 (1H, s).

Step 2: Preparation of 3,8-dibromo-6-hydroxy-quinoline

6-Amino-3,8-dibromoquinoline (1.1 g) was suspended in phosphoric acid (10 ml) containing water (10 ml) and heated in a sealed glass tube at 180° C. for 4 days. The mixture was cooled to ambient temperature, poured into brine and extracted with ethyl acetate. The organic extract was dried over magnesium sulphate, evaporated under reduced pressure and the residual solid fractionated by chromatography (silica; hexane/ethyl acetate) to give 3,8-dibromo-6-hydroxy-quinoline, 0.4 g, as a pale brown solid.

$^1$H NMR (CDCl$_3$) δ ppm: 6.97 (1H, s); 7.69 (1H, s); 8.09 (1H, s); 8.72 (1H, s).

Stage 2

In a similar procedure to Step 1 of Example 5, 3,8-dibromo-6-hydroxyquinoline was reacted with ethyl 2-bromo-2-methylthioacetate to give ethyl 2-(3,8-dibromo-quinolinyl-6-oxy)-2-methylthioacetate as a pale yellow gum.

$^1$H NMR (CDCl$_3$) δ ppm: 1.36 (3H, t); 2.24 (3H, s); 4.29-4.41 (2H, m); 5.69 (1H, s); 7.12 (1H, d); 7.88 (1H, d); 8.22 (1H, d); 8.89 (1H, d).

In a similar procedure to Step 2 of Example 5, ethyl 2-(3,8-dibromoquinolinyl-6-oxy)-2-methylthioacetate was hydrolysed to give 2-(3,8-dibromoquinolinyl-6-oxy)-2-methylthioacetic acid as a pale yellow solid.

$^1$H NMR (CDCl$_3$) δ ppm: 2.26 (3H, s); 5.71 (1H, s); 7.17 (1H, d); 7.89 (1H, d); 8.27 (1H, d); 8.88 (1H, d).

In a similar procedure to Step 3 of Example 5, 2-(3,8-dibromoquinolinyl-6-oxy)-2-methylthioacetic acid was condensed with 4-amino-4-methylpent-2-yne to give 2-(3,8-dibromoquinolinyl-6-oxy)-2-methylthio-N-(2-methylpent-3-yn-2-yl) acetamide as a colourless solid, m.p. 178-179° C.

$^1$H NMR (CDCl$_3$) δ ppm: 1.68 (3H, s); 1.70 (3H, s); 1.84 (3H, s); 2.21 (3H, s); 5.60 (1H, s); 6.66 (1H, s); 7.17 (1H, d); 7.85 (1H, d); 8.27 (1H, d); 8.91 (1H, s).

EXAMPLE 20

This Example illustrates the preparation of 2-(3-bromoquinolinyl-6-oxy)-2-methylthio-N-(2-methylpent-3-yn-2-yl) acetamide (Compound No. 2 of Table 20)

In a similar procedure to Step 1 of Example 5, 3-bromo-6-hydroxyquinoline (preparation described in Liebigs Ann Chem (1966), 98-106) was reacted with ethyl 2-bromo-2-methylthioacetate to give ethyl 2-(3-bromoquinolinyl-6-oxy)-2-methylthioacetate as a pale yellow gum.

$^1$H NMR (CDCl$_3$) δ ppm: 1.34 (3H, t); 2.24 (3H, s); 4.30-4.38 (2H, m); 5.70 (1H, s); 7.14 (1H, m); 7.48-7.52 (1H, dd); 8.02 (1H, d); 8.22 (1H, s); 8.80 (1H, s).

In a similar procedure to Step 2 of Example 5, ethyl 2-(3-bromoquinolinyl-6-oxy)-2-methylthioacetate was converted to 2-(3-bromoquinolinyl-6-oxy)-2-methylthioacetic acid, colourless solid, m.p. 166-167° C.

$^1$H NMR (CDCl$_3$) δ ppm: 2.26 (3H, s); 5.76 (1H, s); 7.20 (1H, m); 7.50-7.54 (1H, dd); 8.01 (1H, d); 8.28 (1H, d); 8.78 (1H, s).

In a similar procedure to Step 3 of Example 5, 2-(3-bromoquinolinyl-6-oxy)-2-methylthioacetic acid was condensed with 4-amino-4-methylpent-2-yne to give 2-(3-bromoquinolinyl-6-oxy)-2-methylthio-N-(2-methylpent-3-yn-2-yl) acetamide as a colourless solid, m.p. 135-137° C.

$^1$H NMR (CDCl$_3$) δ ppm: 1.70 (3H, s); 1.71 (3H, s); 1.83 (3H, s); 2.22 (3H, s); 5.62 (1H, s); 6.72 (1H, s); 7.18 (1H, d); 7.47 (1H, dd); 8.05 (1H, d); 8.24 (1H, d); 8.82 (1H, m).

EXAMPLE 21

This Example illustrates the preparation of 2-(3-chloroquinolinyl-6-oxy)-2-methylthio-N-(2-methylpent-3-yn-2-yl) acetamide (Compound No. 2 of Table 23)

Stage 1: Preparation of 3-chloro-6-hydroxyquinoline

To a stirred solution of 3-bromo-6-hydroxyquinoline (1.0 g) in N-methylpyrrolidin-2-one (12 ml, deoxygenated by bubbling nitrogen through the solution) was added copper (1) chloride (1.10 g) and potassium chloride (1.66 g). The mixture was heated to 120° C. for 2 hours under an atmosphere of nitrogen then for 2 hours at 170° C. The reaction was diluted with saturated aqueous ammonium chloride solution, ethyl acetate was added and the mixture was stirred to dissolve the required product. The mixture was filtered to remove the insoluble material and the organic phase separated. The aqueous phase was extracted with ethyl acetate (three times) and the insoluble material washed with warm ethyl acetate. The ethyl acetate fractions were combined, washed with water, dried over magnesium sulphate then evaporated under reduced pressure to give a solid. The solid was fractionated by chromatography (silica; ethyl acetate/hexane 9:1 by volume) to give 3-chloro-6-hydroxyquinoline, 0.7 g, as a colourless solid.

$^1$H NMR (CDCl$_3$) δ ppm: 7.06 (1H, d); 7.35 (1H, dd); 7.91 (1H, d); 7.96 (1H, d); 8.59 (1H, d); 9.55 (1H, s).

Stage 2

In a similar procedure to Example 18, 3-chloro-6-hydroxyquinoline was reacted with 2-chloro-2-methylthio-N-(2-methylpent-3-yn-2-yl)acetamide to give 2-(3-chloroquinolinyl-6-oxy)-2-methylthio-N-(2-methylpent-3-yn-2-yl) acetamide as a colourless solid, m.p. 105° C.

$^1$H NMR (CDCl$_3$) δ ppm: 1.70 (3H, s); 1.71 (3H, s); 1.83 (3H, s); 2.22 (3H, s); 5.62 (1H, s); 6.72 (1H, s); 7.20 (1H, d); 7.47 (1H, dd); 8.07 (1H, d); 8.08 (1H, s); 8.73 (1H, d).

EXAMPLE 22

This Example illustrates the preparation of 2-(3-fluoroquinolinyl-6-oxy)-2-methylthio-N-(2-methylpent-3-yn-2-yl) acetamide (Compound No. 2 of Table 22)

Step 1: Preparation of 3-fluoro-6-hydroxyquinoline.

To a stirred solution of 3-bromo-6-hydroxyquinoline (0.67 g) in dry tetrahydrofuran (15 ml) cooled to −78° C. under an atmosphere of nitrogen was added dropwise absolution of n.butyl lithium (2.4 ml, 2.5M solution in hexanes) such that the reaction was maintained below −72° C. The orange suspension that was produced was stirred at −78° C. and a solution of N-fluorobenziensulphonimide (0.97 g) in tetrahydrofuran (10 ml) was added dropwise maintaining the reaction below −68° C. during the addition. The red solution that formed was stirred, allowing the reaction to gradually reach ambient temperature. The solution was treated with water then taken to pH 4-5 with aqueous hydrochloric acid. The emulsion that formed was extracted with ethyl acetate, separated and the organic phase was washed with brine, dried over magnesium sulphate and evaporated under reduced pressure. The residual gum was fractionated by chromatography (silica; hexane/ethyl acetate) to give an orange solid containing the desired product.

In a similar procedure to Step 1 of Example 5, 3-fluoro-6-hydroxyquinoline was reacted with ethyl 2-bromo-2-methylthioacetate to give ethyl 2-(3-fluoroquinolinyl-6-oxy)-2-methylthioacetate as a gum.

¹H NMR (CDCl₃) δ ppm: 1.35 (3H, t); 2.24 (3H, s); 4.29-4.40 (2H, m); 5.71 (1H, s); 7.20 (1H, d); 7.46 (1H, dd); 7.69 (1H, dd); 8.07 (1H, d); 8.71 (1H, dd).

In a similar procedure to Step 2 of Example 5, ethyl 2-(3-fluoroquinolinyl-6-oxy)-2-methylthioacetate was hydrolysed to give 2-(3-fluoroquinolinyl-6-oxy)-2-methylthioacetic acid as a pale yellow solid that was used in the next step without further purification.

In a similar procedure to Step 3 of Example 5, 2-(3-fluoroquinolinyl-6-oxy)-2-methylthioacetic acid was condensed with 4-amino-4-methylpent-2-yne to give 2-(3-fluoroquinolinyl-6-oxy)-2-methylthio-N-(2-methylpent-3-yn-2-yl) acetamide as a colourless gum.

¹H NMR (CDCl₃) δ ppm: 1.68 (3H, s); 1.70 (3H, s); 1.83 (3H, s); 2.21 (3H, s); 5.62 (1H, s); 6.72 (1H, s); 7.23 (1H, d); 7.42 (1H, dd); 7.71 (1H, dd); 8.09 (1H, d); 8.71 (1H, d).

EXAMPLE 23

This Example illustrates the preparation of 2-(isoquinolinyl-7-oxy)-2-methylthio-N-(2-methylpent-3yn-2-yl) acetamide (Compound No. 2 of Table 18).

In a similar procedure to Step 1 of Example 5, 7-hydroxyisoquinoline (commercially available) was reacted with ethyl 2-bromo-2-methylthioacetate to give ethyl 2-(isoquinolinyl-7-oxy)-2-methylthioacetate as a red oil.

¹H NMR (CDCl₃) δ ppm: 1.37 (3H, t); 2.25 (3H, s); 4.30-4.42 (2H, m); 5.75 (1H, s); 7.37 (1H, m); 7.50 (1H, dd); 7.62 (1H, dd); 7.80 (1H, d); 8.47 (1H, d); 9.18 (1H, s).

In a similar procedure to Step 2 of Example 5, ethyl 2-(isoquinolinyl-7-oxy)-2-methylthioacetate was hydrolysed to 2-(isoquinolinyl-7-oxy)-2-methylthioacetic acid as a pale brown solid.

¹H NMR (DMSO-d₆) δ ppm: 2.17 (3H, s); 6.22 (1H, s); 7.92 (1H, dd); 7.97 (1H, d); 8.27 (1H, d); 8.37 (1H, d); 8.58 (1H, d); 9.66 (1H, s).

In a similar procedure to Step 3 of Example 5, 2-(isoquinolinyl-7-oxy)-2-methylthioacetic acid was condensed with 4-amino-4-methylpent-2-yne to give 2-(isoquinolinyl-7-oxy)-2-methylthio-N-(2-methylpent-3-yn-2-yl) acetamide as an off-white solid, m.p. 167-168° C.

¹H NMR (CDCl₃) δ ppm: 1.68 (3H, s); 1.69 (3H, s); 1.82 (3H, s); 2.22 (3H, s); 5.65 (1H, s); 6.73 (1H, s); 7.42 (1H, m); 7.46 (1H, dd); 7.62 (1H, d); 7.82 (1H, d); 8.49 (1H, d); 9.19 (1H, s).

EXAMPLE 24

This Example illustrates the preparation of 2-(isoquinolinyl-6-oxy)-2-methylthio-N-(2-methylpent-3-yn-2-yl) acetamide. (Compound No. 2 of Table 27)

In a similar procedure to Step 1 of Example 5, 6-hydroxyisoquinoline (preparation described in J. Org. Chem. (1953), 18, 3345) was reacted with ethyl 2-bromo-2-methylthioacetate to give ethyl 2-(isoquinolinyl-6-oxy)-2-methylthioacetate as an orange gum.

¹H NMR (CDCl₃) δ ppm: 1.36 (3H, t); 2.25 (3H, s); 4.29-4.42 (2H, m); 5.76 (1H, s); 7.20 (1H, m); 7.38 (1H, dd); 7.57 (1H, d); 7.93 (1H, d); 8.48 (1H, d); 9.15 (1H, s).

In a similar procedure to Step 2 of Example 5, ethyl 2-(isoquinolinyl-6-oxy)-2-methylthioacetate was hydrolysed to 2-(isoquinolinyl-6-oxy)-2-methylthioacetic acid. The acid was obtained by making the aqueous solution slightly acidic (pH 5) and removing the water by evaporating under reduced pressure. The required acid and inorganic residues were used directly in the next step without further purification.

¹H NMR (D₂O) δ ppm: 2.19 (3H, s); 5.67 (1H, s); 7.03 (1H, d), 7.23 (1H, dd); 7.49 (1H, d); 7.82 (1H, d); 8.18 (1H, d); 8.87 (1H, s).

In a similar procedure to Step 3 of Example 5, 2-(isoquinolinyl-6-oxy)-2-methylthioacetic acid was condensed with 4-amino-4-methylpent-2-yne to give 2-(isoquinolinyl-6-oxy)-2-methylthio-N-(2-methylpent-3-yn-2-yl) acetamide as a colourless gum.

¹H NMR (CDCl₃) δ ppm: 1.68 (3H, s); 1.69 (3H, s); 1.82 (3H, s); 2.21 (3H, s); 5.67 (1H, s); 6.74 (1H, s); 7.25 (1H, m); 7.35 (1H, dd); 7.58 (1H, d); 7.96 (1H, d); 8.49 (1H, d); 9.17 (1H, s).

EXAMPLE 25

This Example illustrates the preparation of 2-(2,1,3-benzoxadiazolyl-5-oxy)-2-methylthio-N-(2-methylpent-3-yn-2-yl) acetamide (Compound No. 2 of Table 41)

In a similar procedure to Step 1 of Example 5, 5-hydroxy-2,1,3-benzoxadiazol (commercially available) was reacted with ethyl 2-bromo-2-methylthioacetate to give ethyl 2-(2,1,3-benzoxadiazolyl-5-oxy)-2-methylthioacetate as a pale yellow solid, m.p. 77-79° C.

¹H NMR (CDCl₃) δ ppm: 1.36 (3H, t); 2.26 (3H, s); 4.32-4.38 (2H, q); 5.64 (1H, s); 6.98 (1H, m); 7.22-7.26 (1H, dd); 7.78 (1H, d).

In a similar procedure to Step 2 of Example 5, ethyl 2-(2,1,3-benzoxadiazolyl-5-oxy)-2-methylthioacetate was hydrolysed to give ethyl 2-(2,1,3-benzoxadiazolyl-5-oxy)-2-methylthioacetic acid as a gum.

¹H NMR (CDCl₃) δ ppm: 2.30 (3H, s); 5.72 (1H, s); 7.06 (1H, d); 7.22-7.26 (1H, dd); 7.82 (1H, d).

In a similar procedure to Step 3 of Example 5, ethyl 2-(2,1,3-benzoxadiazolyl-5-oxy)-2-methylthioacetic acid was condensed with 4-amino-4-methylpent-2-yne to give 2-(2,1,3-benzoxadiazolyl-5-oxy)-2-methylthio-N-(2-methylpent-3-yn-2-yl) acetamide as a pale brown solid, m.p. 120-122° C.

¹H NMR (CDCl₃) δ ppm: 1.70 (3H, s); 1.82 (3H, s); 2.22 (3H, s); 5.58 (1H, s); 6.56 (1H, s); 7.06 (1H, m); 7.24 (1H, dd); 7.82 (1H, d).

EXAMPLE 26

This Example illustrates the preparation of 2-(2-bromobenzothiazoyl-6-oxy)-2-methylthio-N-(2-methylpent-3-yn-2-yl) acetamide (Compound No. 2 of Table 43)

Stage 1: Preparation of 2-bromo-6-hydroxybenzothiazole
Step 1

In a similar procedure to that described in U.S. Pat. No. 4,873,346 for the preparation of 2-chloro-6-methoxybenzothiazole, 2-amino-6-methoxybenzothiazole (commercially available) was converted to 2-bromo-6-methoxybenzothiazole (pale yellow solid, m.p. 53-54° C.) using copper (1) bromide in place of copper (1) chloride.

Step 2

To a stirred solution of 2-bromo-6-methoxybenzothiazole (0.67 g) in dry dichloromethane (30 ml) at ambient temperature under an atmosphere of nitrogen was added dropwise a solution of boron tribromide in dichloromethane (5.5 ml, 1M). The mixture was stirred for 2 hours at ambient temperature, stored for 2 days then poured into water. The organic phase was separated, washed with water, dried over magnesium sulphate then evaporated under reduced pressure to give 2-bromo-6-hydroxybenzothiazole as a pale pink solid, 0.60 g, m.p. 203-204° C.

In a similar procedure to Step 1 of Example 5, 2-bromo-6-hydroxybenzothiazole was reacted with ethyl 2-bromo-2-methylthioacetate to give ethyl 2-(2-bromobenzo-thiazoyl-6-oxy)-2-methylthioacetate as a pale yellow oil.

$^1$H NMR (CDCl$_3$) δ ppm: 1.36 (3H, t); 2.24 (3H, s); 4.30-4.36 (2H, q); 5.62 (1H, s); 7.20 (1H, dd); 7.42 (1H, d); 7.92 (1H, d).

In a similar procedure to Step 2 of Example 5, ethyl 2-(2-bromobenzothiazoyl-6-oxy)-2-methylthioacetate was hydrolysed to give 2-(2-bromobenzothiazoyl-6-oxy)-2-methylthioacetic acid as a pale yellow gum.

$^1$H NMR (CDCl$_3$) δ ppm: 2.26 (3H, s); 5.70 (1H, s); 7.22 (1H, dd); 7.46 (1H, d); 7.94 (1H, d).

In a similar procedure to Step 3 of Example 5, 2-(2-bromobenzothiazoyl-6-oxy)-2-methylthioacetic acid was condensed with 4-amino-4-methylpent-2-yne to give 2-(2-bromobenzothiazoyl-6-oxy)-2-methylthio-N-(2-methylpent-3-yn-2-yl) acetamide as a colourless oil.

$^1$H NMR (CDCl$_3$) δ ppm: 1.69 (6H, s); 1.82 (3H, s), 2.19 (3H, s); 5.52 (1H, s); 6.73 (1H, s); 7.18 (1H, dd); 7.44 (1H, dd); 7.93 (1H, d).

EXAMPLE 27

This Example illustrates the preparation of 2-(2-chlorobenzothiazoyl-6-oxy)-2-methyl-thio-N-(2-methylpent-3-yn-2-yl) acetamide (Compound No. 2 of Tables 42)

In a similar procedure to Step 1 of Example 5, 2-chloro-6-hydroxybenzothiazole (preparation described in U.S. Pat. No. 4,873,346) was reacted with ethyl 2-bromo-2-methylthioacetate to give ethyl 2-(2-chlorobenzothiazoyl-6-oxy)-2-methylthioacetate as a pale brown oil.

$^1$H NMR (CDCl$_3$) δ ppm: 1.34 (3H, t); 2.22 (3H, s); 4.30-4.36 (2H, q); 5.62 (1H, s); 7.20 (1H, dd); 7.40 (1H, d); 7.88 (1H, d).

In a similar procedure to Step 2 of Example 5, ethyl 2-(2-chlorobenzothiazoyl-6-oxy)-2-methylthioacetate was hydrolysed to give 2-(2-bromobenzothiazoyl-6-oxy)-2-methylthioacetic acid as a pale orange gum.

$^1$H NMR (CDCl$_3$) δ ppm: 2.26 (3H, s); 5.68 (1H, s); 7.22 (1H, dd); 7.42 (1H, d); 7.92 (1H, d).

In a similar procedure to Step 3 of Example 1, 2-(2-chlorobenzothiazoyl-6-oxy)-2-methylthioacetic acid was condensed with 4-amino-4-methylpent-2-yne to give 2-(2-chlorobenzothiazoyl-6-oxy)-2-methylthio-N-(2-methylpent-3-yn-2-yl) acetamide as a pale yellow gum.

$^1$H NMR (CDCl$_3$) δ ppm: 1.70 (6H, s); 1.84 (3H, s); 2.18 (3H, s); 5.52 (1H, s); 6.72 (1H, s); 7.20 (1H, dd); 7.42 (1H, dd); 7.90 (1H, d).

EXAMPLE 28

This Example illustrates the preparation of 2-(3-bromoquinolinyl-6-oxy)-2-methylthio-N-(1-chloro-6-methylhept-4-yn-6-yl) acetamide (Compound No. 90 of Table 20)
Stage 1: Preparation of 1-chloro-6-methylhept-4-yn-6-ylamine hydrochloride
Step 1: Preparation of 6-(1-chloro-6-methylhept-4-yn-6-yl)-2,2,5,5-tetramethyl-1-aza-2,5-disilacyclopentane n-Butyl lithium (97.6 ml, 2.5M in hexanes) was added dropwise over 0.5 hours to a stirred solution of 1-(1,1-dimethyl-2-propynyl)-2,2,5,5-tetramethyl-1-aza-2,5-disilacyclopentane (55.1 g) in dry tetrahydrofuran (450 ml) under an atmosphere of nitrogen at −70° C. The mixture was stirred for 1.5 hours at −70° C., allowed to warm to −15° C. then a solution of 1-chloro-3-iodopropane (55.0 g) in dry tetrahydrofuran (50 ml) was added dropwise over 20 minutes whilst allowing the reaction temperature to slowly warm to 0° C. On complete addition, the reaction mixture was stirred at ambient temperature for 4.25 hours then stored for 18 hours. The mixture was diluted with water and extracted with ethyl acetate (twice). The extracts were combined, washed with water (three times), dried over magnesium sulfate then evaporated under reduced pressure to give the required product as an orange liquid, 78.5 g.

$^1$H NMR (CDCl$_3$) δ ppm: 0.00 (12H, s); 0.46 (4H, s); 1.30 (6H, s); 1.76 (2H, m); 2.18 (2H, t); 2.46 (2H, t).
Step 2: Preparation of 1-chloro-6-methylhept-4-yn-6-ylamine hydrochloride The product from Step 1 (78.5 g) was stirred at −5° C. and dilute aqueous hydrochloric acid (785 ml, 2M) was slowly added, maintaining the reaction temperature below 30° C. during the addition. On complete addition, the mixture was stirred for a further 1 hour at ambient temperature, washed with diethyl ether (twice), evaporated under reduced pressure and the residual water removed by azeotropic distillation with toluene. The solid obtained was dissolved in dichloromethane, dried over magnesium sulfate and evaporated under reduced pressure to give the required product as a cream coloured solid, 36.5 g.

$^1$H NMR (CDCl$_3$) δ ppm: 1.74 (6H, s); 1.97 (2H, m); 2.39 (2H, m); 3.68 (2H, t); 8.80 (3H, broad signal).
Stage 2:

In a similar procedure to Step 3 of Example 1, 2-(3-bromoquinolinyl-6-oxy)-2-methylthioacetic acid was condensed with 1-chloro-6-methylhept-4-yn-6-ylamine hydrochloride to give 2-(3-bromoquinolinyl-6-oxy)-2-methylthio-N-(1-chloro-6-methylhept-4-yn-6-yl) acetamide as a yellow solid, m.p. 133-135° C.

$^1$H NMR (CDCl$_3$) δ ppm: 1.70 (6H, s); 1.95 (2H, q); 2.22 (3H, s); 2.40 (2H, t); 3.68 (2H, t); 5.62 (1H, s); 6.68 (1H, s); 7.18 (1H, m); 7.48 (1H, dd); 8.04 (1H, d); 8.26 (1H, m); 8.82 (1H, d).

EXAMPLE 29

This Example illustrates the preparation of 2-(3-bromoquinolinyl-6-oxy)-2-methylthio-N-(1-cyano-6-methylhept-4-yn-6-yl) acetamide (Compound No. 21 of Table 20)

To a stirred solution of 2-(3-bromoquinolinyl-6-oxy)-2-methylthio-N-(1-chloro-6-methylhept-4-yn-6-yl) acetamide (0.61 g) in dry N,N-dimethylformamide (10 ml) was added potassium cyanide-(0.17 g) and the mixture heated to 100° C. for 6.25 hours, cooled to ambient temperature then stored for 18 hours. The reaction mixture was poured into water, extracted with ethyl acetate (three times) and the extracts combined, washed with water (twice), dried over magnesium sulphate and evaporated under reduced pressure to give an oil. The oil was fractionated by chromatography (silica; hexane/ethyl acetate, 1:1 by volume) to give 2-(3-bromoquinolinyl-6-oxy)-2-methylthio-N-(1-cyano-6-methylhept-4-yn-6-yl) acetamide as a yellow solid, 0.27 g, m.p. 140-141° C.

$^1$H NMR (CDCl$_3$) δ ppm: 1.68 (6H, s); 1.86 (2H, q); 2.22 (3H, s); 2.40 (2H, t); 3.66 (2H, t); 5.62 (1H, s); 6.68 (1H, s); 7.18 (1H, m); 7.48 (1H, dd); 8.04 (1H, d); 8.26 (1H, m); 8.82 (1H, d).

In a similar procedure to Example 29, 2-(benzothiazoyl-6-oxy)-2-methylthio-N-(1-chloro-6-methylhept-4-yn-6-yl) acetamide was reacted with potassium cyanide to give 2-(benzothiazoyl-6-oxy)-2-methylthio-N-(1-cyano-6-methylhept-4-yn-6-yl) acetamide (Compound No. 21 of Table 34) as a yellow gum.

$^1$H NMR (CDCl$_3$) δ ppm: 1.68 (6H, s); 1.82-1.90 (2H, m); 2.22 (3H, s); 2.40 (2H, t); 2.56 (2H, t); 5.54 (1H, s); 6.72 (1H, s); 7.24 (1H, dd); 7.58 (1H, d); 8.09 (1H, d); 8.92 (1H, s).

In a similar procedure to Example 29, 2-(5-chloropyridyl-3-oxy)-2-methylthio-N-(1-chloro-6-methylhept-4-yn-6-yl) acetamide was reacted with potassium cyanide to give 2-(5-chloropyridyl-3-oxy)-2-methylthio-N-(1-cyano-6-methylhept-4-yn-6-yl) acetamide (Compound No. 148 of Table 31) as a yellow oil.

$^1$H NMR (CDCl$_3$) δ ppm: 1.68 (3H, s); 1.70 (3H, s); 1.82-1.90 (2H, m); 2.16 (3H, s) 2.38-2.42 (2H, t); 2.54-2.58 (2H, t); 5.50 (1H, s); 6.62 (1H, s); 7.38 (1H, m); 8.31 (2H, m).

EXAMPLE 30

This Example illustrates the preparation of 2-(3,5-dichlorophenoxy)-2-methylthio-N-(1-cyano-6-methylhept-4-yn-6-yl) acetamide (Compound No. 4 of Table 13)

Stage 1: Preparation of 6-amino-1-cyano-6-methylhept-4-yne hydrochloride

To a stirred solution of 6-(1-chloro-6-methylhept-4-yn-6-yl)-2,2,5,5-tetramethyl-1-aza-2,5-disilacyclopentane (1.00 g) in dry N,N-dimethylformamide (10 ml) was added potassium cyanide (0.21 g) and the mixture heated to 90° C. for 18 hours then cooled to ambient temperature. The mixture was poured into water, extracted with ethyl acetate (three times), the extracts combined, washed with water (twice), dried over magnesium sulphate and evaporated under reduced pressure to give 6(1-cyano-6-methylhept-4-yn-6-yl)-2,2,5,5-tetramethyl-1-aza-2,5-disilacyclopentane as a red oil, 0.95 g.

The oil was mixed with aqueous hydrochloric acid (9.5 ml, 2M) and stirred at ambient temperature for 1.25 hours. The aqueous phase was washed with diethyl ether (twice) then evaporated under reduced pressure removing the final traces of water by azeotropic distillation with toluene to give 6-amino-1-cyano-6-methylhept-4-yne hydrochloride as a yellow solid, 0.59 g.

Stage 2

In a similar procedure to Step 3 of Example 1, 2-(3,5-dichlorophenoxy)-2-methylthioacetic acid was condensed with 1-cyano-6-methylhept-4-yn-6-ylamine hydrochloride to give 2-(3,5-dichlorophenoxy)-2-methylthio-N-(1-cyano-6-methylhept-4-yn-6-yl) acetamide as an off white solid, m.p. 113-114° C.

$^1$H NMR (CDCl$_3$) δ ppm: 1.66 (6H, s); 1.82-1.90 (2H, m); 2.16 (3H, s); 2.40 (2H, t); 2.54 (2H, t); 5.44 (1H, s); 6.56 (1H, s); 6.94 (2H, d); 7.10 (1H, m).

EXAMPLE 31

This Example illustrates the preparation of 2-(2-methylaminobenzothiazoyl-6-oxy)-2-methylthio-N-(2-methylpent-3-yn-2-yl) acetamide (Compound No. 2 of Table 44)

Step 1: Preparation of ethyl 2-(2-methylaminobenzothiazoyl-6-oxy)-2-methyl-thioacetate To a stirred suspension of sodium hydride (0.32 g, 80% in mineral oil) in dry N,N-dimethylformamide (10 ml) under an atmosphere of nitrogen at ambient temperature was added a solution of 2-methylamino-6-hydroxybenzothiazole (preparation given in J. Org. Chem. (1970), 35, No 12, 4103-4108; 1.80 g) in N,N-dimethylformamide over 10 minutes. The reaction mixture was stirred for 0.5 hours then ethyl 2-bromo-2-methyl-thioacetate (2.60 g) in N,N-dimethylformamide (10 ml) was added over 5 minutes and the mixture stirred for 2 hours then stored for 18 hours at ambient temperature. Water was added and the product extracted into ethyl acetate (three times). The extracts were combined, washed with brine (twice), dried over magnesium sulphate and evaporated under reduced pressure to give an oil. The oil was fractionated by chromatography (silica; hexane/ethyl acetate (95:5 to 5:95 by volume) to give ethyl 2-(2-methylamino-benzothiazoyl-6-oxy)-2-methylthioacetate as a dark orange gum, 0.97 g.

$^1$H NMR (CDCl$_3$) δ ppm: 1.34 (3H, t); 2.22 (3H, s); 3.10 (3H, s); 4.28-4.36 (2H, m); 5.38 (1H, bs); 5.54 (1H, s); 7.02 (1H, dd); 7.30 (1H, m); 7.46 (1H, d).

Step 2: Preparation of give 2-(2-methylaminobenzothiazoyl-6-oxy)-2-methylthio acetic acid In a similar procedure to Step 2 of Example 1, ethyl 2-(2-methylaminobenzo-thiazoyl-6-oxy)-2-methylthioacetate was hydrolysed to give 2-(2-methylaminobenzo-thiazoyl-6-oxy)-2-methylthio acetic acid as a pale brown solid, m.p. 115-118° C.

$^1$H NMR (d6-DMSO) δ ppm: 2.06 (3H, s); 2.84 (3H, s); 5.76 (1H, s); 6.88 (1H, dd); 7.24 (1H, d); 7.36 (1H, m).

Step 3:

In a similar procedure to Step 3 of Example 5, 2-(2-methylaminobenzothiazoyl-6-oxy)-2-methylthioacetic acid was condensed with 4-amino-4-methylpent-2-yne hydrochloride to give 2-(2-methylaminobenzothiazoyl-6-oxy)-2-(methylthio)-N-(-(2-methylpent-3-yn-2-yl) acetamide as a pale yellow solid, m.p. 68-71° C.

$^1$H NMR (CDCl$_3$) δ ppm: 1.68 (3H, s); 1.70 (3H, s); 1.84 (3H, s); 2.18 (3H, s); 3.12 (3H, s); 5.25 (1H, bs); 5.42 (1H, s); 6.78 (1H, bs); 6.98-7.02 (1H, dd); 7.28 (1H, m); 7.47-7.51 (1H, d).

EXAMPLE 32

This examples illustrates the preparation of 2-(3-bromo-8-chloroquinolinyl-6-oxy)-2-methylthio-N-(2-methylpent-3-yn-2-yl) acetamide (Compound No. 2 of Table 25)

In a similar procedure to Step 2 of Example 19, 6-amino-3-bromo-8-chloroquinoline [preparation given in J Am Chem Soc (1955), 77, 4175-4176] was hydrolysed to give 3-bromo-8-chloro-6-hydroxyquinoline as a brown solid.

$^1$H NMR (CDCl$_3$) δ ppm: 7.00 (1H, d); 7.52 (1H, d); 8.17 (1H, d); 8.77 (1H, d); very broad signal at 7 ppm for OH.

In a similar procedure to Step 1 of Example 5, 3-bromo-8-chloro-6-hydroxyquinoline was reacted with ethyl 2-bromo-2-methylthioacetate to give ethyl 2-(3-bromo-8-chloroquinolinyl-6-oxy)-2-methylthioacetate as a yellow gum.

$^1$H NMR (CDCl$_3$) δ ppm: 1.37 (3H, t); 2.23 (3H, s); 4.28-4.40 (2H, m); 5.69 (1H, s); 7.08 (1H, d); 7.68 (1H, d); 8.25 (1H, d); 8.90 (1H, d).

In a similar procedure to Step 2 of Example 5, ethyl 2-(3-bromo-8-chloroquinolinyl-6-oxy)-2-methylthioacetate was hydrolysed to 2-(3-bromo-8-chloroquinolinyl-6-oxy)-2-methylthioacetic acid as a colourless solid.

$^1$H NMR (d6-DMSO) δ ppm: 2.17 (3H, s); 6.16 (1H, s); 7.52 (1H, d); 7.86 (1H, d); 8.68 (1H, d); 8.93 (1H, d).

In a similar procedure to Step 3 of Example 5, 2-(3-bromo-8-chloroquinolinyl-6-oxy)-2-methylthioacetic acid was condensed with 4-amino-4-methylpent-2-yne hydrochloride to give 2-(3-bromo-8-chloroquinolinyl-6-oxy)-2-(methylthio)-N-(-(2-methylpent-3-yn-2-yl) acetamide as a colourless solid, m.p. 166-167° C.

$^1$H NMR (CDCl$_3$) δ ppm: 1.70 (6H, s); 1.83 (3H, s); 2.21 (3H, s); 5.60 (1H, s); 6.66 (1H, bs); 7.12 (1H, d); 7.64 (1H, d); 8.28 (1H, d); 8.92 (1H, d).

EXAMPLE 33

This Example illustrates the preparation of 2-(1-methylindazoyl-5-oxy)-2-methylthio-N-(2-methylpent-3-yn-2-yl) acetamide (Compound No. 2 of Table 45)

Step 1: Preparation of 5-amino-1-methylindazole

To a stirred solution of 1-methyl-5-nitroindazole (3.24 g, commercially available) in concentrated hydrochloric acid (75 ml) was added iron powder (3.53 g) in portions over 10 minutes, allowing the reaction temperature to gradually rise to 52° C. On complete addition, the reaction mixture was heated to 70-75° C. for 1 hour, cooled to ambient temperature and stored for 18 hours. The mixture was chilled by the addition of ice then taken to pH 9 with aqueous sodium hydroxide filtered and the filtrate and insoluble solids extracted with ethyl acetate (three times). The extracts were combined, washed with brine and dried over magnesium sulphate then evaporated under reduced pressure to give 5-amino-1-methylindazole as a pale brown solid.

$^1$H NMR (CDCl$_3$) δ ppm: 3.92 (3H, s); 4.80 (2H, s); 6.74 (1H, m); 6.82 (1H, dd); 7.32 (1H, d); 7.66 (1H, s).

5-Amino-1-methylindazole (1.56 g) in phosphoric acid (13 ml) containing water (3 ml) was heated to 180° C. for 18 hours, cooled to ambient temperature, poured into water (5 ml) then neutralised with aqueous sodium hydroxide. The solid that precipitated was filtered from solution, washed with cold water then sucked to dryness to give was hydrolysed to give 5-hydroxyl-1-methylindazole as a brown solid, (1.18 g).

$^1$H NMR (d6-DMSO) δ ppm: 3.96 (3H, s); 6.94 (2H, m); 7.44 (1H, d); 7.80 (1H, s); 9.14 (1H, s).

In a similar procedure to Step 1 of Example 31, 5-hydroxy-1-methylindazole was reacted with ethyl 2-bromo-2-methylthioacetate to give ethyl 2-(1-methylindazoyl-5-oxy)-2-methylthioacetate.

$^1$H NMR (CDCl$_3$) δ ppm: 1.36 (3H, t); 2.24 (3H, s); 4.06 (3H, s); 4.30-4.38 (2H, m); 5.58 (1H, s); 7.20 (1H, dd); 7.26 (1H, s); 7.36 (1H, d); 7.90 (1H, s).

In a similar procedure to Step 2 of Example 5, ethyl 2-(1-methylindazoyl-5-oxy)-2-methylthioacetate was hydrolysed to give 2-(1-methylindazoyl-5-oxy)-2-methylthioacetic acid.

$^1$H NMR (CDCl$_3$) δ ppm: 2.26 (3H, s); 4.06 (3H, s); 5.60 (1H, s); 7.22 (1H, dd); 7.28 (1H, d); 7.36 (1H, d); 7.92 (1H, s).

In a similar procedure to Step 3 of Example 5, 2-(1-methylindazoyl-5-oxy)-2-methylthioacetic acid was condensed with 4-amino-4-methylpent-2-yne to give 2-(1-methylindazoyl-5-oxy)-2-methylthio-N-(2-methylpent-3-yn-2-yl) acetamide.

$^1$H NMR (CDCl$_3$) δ ppm: 1.68 (3H, s); 1.70 (3H, s); 1.84 (3H, s); 2.18 (3H, s); 4.06 (3H, s); 5.46 (1H, s); 6.81 (1H, s); 7.16 (1H, dd); 7.30 (1H, d); 7.36 (1H, d); 7.92 (1H, s).

TABLE 142

This table gives characterising data (NMR, melting point or refractive index data) for compounds that are listed in Tables 1 to 129.

| Compound No. | Table No. | (Solvent CDCl$_3$): $^1$H NMR chemical shifts in ppm from TMS, or melting point (mpt) or refractive index ($n_D^{30}$) |
|---|---|---|
| 2 | 1 | 1.68(6H, s); 1.83(3H, s); 2.16(3H, s); 5.41(1H, s); 6.85(1H, bs); 7.09(2H, s). |
| 2 | 14 | 1.69(3H, s); 1.70(3H, s); 1.82(3H, s); 2.22(3H, s); 5.64(1H, s); 6.76(1H, s); 7.28(1H, d); 7.40(1H, dd); 7.47(1H, dd); 8.09(1H, m); 8.84(1H, dd). |
| 2 | 16 | 1.70(3H, s); 1.71(3H, s); 1.82(3H, s); 2.22(3H, s); 5.65(1H, s); 6.70(1H, s); 7.37(1H, m); 7.69(1H, dd); 8.06(1H, d); 9.28(1H, d); 9.36(1H, s). |
| 2 | 18 | 1.68(3H, s); 1.69(3H, s); 1.82(3H, s); 2.22(3H, s); 5.65(1H, s); 6.73(1H, s); 7.42(1H, m); 7.46(1H, dd); 7.62(1H, d); 7.82(1H, d); 8.49(1H, d); 9.19(1H, s). |
| 2 | 20 | 1.70(3H, s); 1.71(3H, s); 1.83(3H, s); 2.22(3H, s); 5.62(1H, s); 6.72(1H, s); 7.18(1H, d); 7.47(1H, dd); 8.05(1H, d); 8.24(1H, d); 8.82(1H, m). |
| 2 | 22 | 1.68(3H, s); 1.70(3H, s); 1.83(3H, s); 2.21(3H, s); 5.62(1H, s); 6.72(1H, s); 7.23(1H, d); 7.42(1H, dd); 7.71(1H, dd); 8.09(1H, d); 8.71(1H, d). |
| 2 | 23 | 1.70(3H, s); 1.71(3H, s); 1.83(3H, s); 2.22(3H, s); 5.62(1H, s); 6.72(1H, s); 7.20(1H, d); 7.47(1H, dd); 8.07(1H, d); 8.08(1H, s); 8.73(1H, d). |
| 2 | 25 | 1.70(6H, s); 1.83(3H, s); 2.21(3H, s); 5.60(1H, s); 6.66(1H, bs); 7.12(1H, d); 7.64(1H, d); 8.28(1H, d); 8.92(1H, d). |
| 2 | 26 | 1.68(3H, s); 1.70(3H, s); 1.84(3H, s); 2.21(3H, s); 5.60(1H, s); 6.66(1H, s); 7.17(1H, d); 7.85(1H, d); 8.27(1H, d); 8.91(1H, s). |
| 2 | 27 | 1.68(3H, s); 1.69(3H, s); 1.82(3H, s); 2.21(3H, s); 5.67(1H, s); 6.74(1H, s); 7.25(1H, m); 7.35(1H, dd); 7.58(1H, d); 7.96(1H, d); 8.49(1H, d); 9.17(1H, s). |
| 2 | 31 | 1.72(6H, s); 2.18(3H, s); 2.40(1H, s); 5.52(1H, s); 6.64(1H, s); 7.38(1H, m); 8.32(2H, m). |
| 2 | 34 | 1.78(3H, s); 1.80(3H, s); 1.82(3H, s); 2.20(3H, s); 5.54(1H, s); 6.77(1H, bs); 7.23(1H, dd); 7.58(1H, m); 8.09(1H, d); 8.92(1H, s). |
| 2 | 38 | 1.70(6H, s); 1.82(3H, s); 2.20(3H, s); 5.51(1H, s); 6.76(1H, s); 7.10(1H, dd); 7.27(1H, m); 7.72(1H, d); 8.08(1H, s). |
| 2 | 41 | 1.70(3H, s); 1.82(3H, s); 2.22(3H, s); 5.58(1H, s); 6.56(1H, s); 7.06(1H, m); 7.24(1H, dd); 7.82(1H, d). |
| 2 | 42 | 1.70(6H, s); 1.84(3H, s); 2.18(3H, s); 5.52(1H, s); 6.72(1H, s); 7.20(1H, dd); 7.42(1H, dd); 7.90(1H, d). |
| 2 | 43 | 1.69(6H, s); 1.82(3H, s); 2.19(3H, s); 5.52(1H, s); 6.73(1H, s); 7.18(1H, dd); 7.44(1H, dd); 7.93(1H, d). |

TABLE 142-continued

This table gives characterising data (NMR, melting point or refractive index data) for compounds that are listed in Tables 1 to 129.

| Compound No. | Table No. | (Solvent CDCl$_3$): $^1$H NMR chemical shifts in ppm from TMS, or melting point (mpt) or refractive index (n$_D^{30}$) |
|---|---|---|
| 2 | 44 | 1.70(3H, s); 1.84(3H, s); 2.18(3H, s); 3.12(3H, s); 5.25(1H, bs); 5.42(1H, s); 6.78(1H, bs); 6.98–7.02(1H, dd); 7.28(1H, m); 7.47–7.51(1H, d). |
| 2 | 45 | 1.68(3H, s); 1.70(3H, s); 1.84(3H, s); 2.18(3H, s); 4.06(3H, s); 5.46(1H, s); 6.81(1H, s); 7.16(1H, dd); 7.30(1H, d); 7.36(1H, d); 7.92(1H, s). |
| 2 | 81 | 1.67(3H, s); 1.69(3H, s); 1.80(s) and 1.82(s) total of 3H; 2.72(s) and 2.83(s) total of 3H; 5.28(s) and 5.53(s) total of 1H; 6.81(s) and 6.94(s) total of 1H; 7.29(dd) and 7.33(dd) total of 1H; 7.67(m) and 7.79(m) total of 1H; 8.09(m) and 8.94(m) total of 1H. |
| 3 | 1 | 1.67(3H, s); 1.68(3H, s); 1.82(3H, s); 2.11(3H, s); 2.15(3H, s); 2.27(6H, s); 5.43(1H, s); 6.67(2H, m); 7.77(1H, bs). |
| 3 | 31 | 1.70(6H, s); 1.84(3H, s); 2.18(3H, s); 5.48(1H, s); 6.62(1H, bs); 7.38(1H, m); 8.30–8.32(2H, m). |
| 3 | 78 | 1.66(6H, s); 1.82(3H, s); 2.70(s) and 2.82(s) total of 3H; 5.22(s) and 5.46(s) total of 1H; 6.68(s) and 6.88(s) total of 1H; 7.44(m) and 7.5(m) total of 1H; 8.36–8.42(2H, m). |
| 4 | 1 | 1.68(6H, s); 1.83(3H, s); 2.16(3H, s); 5.42(1H, s); 6.58(1H, bs); 6.94(2H, d); 7.09(1H, t). |
| 4 | 2 | 1.28(3H, s); 1.66(6H, s); 1.82(3H, s); 2.27(2H, m); 5.44(1H, s); 6.54(1H, s); 6.92(2H, d); 7.08(1H, m). |
| 4 | 7 | 1.71(6H, s); 2.16(3H, s); 3.38(3H, s); 4.12(2H, s); 5.44(1H, s); 6.59(1H, bs); 6.93(2H, s); 7.10(1H, s). |
| 4 | 13 | 1.66(6H, s); 1.82–1.90(2H, m); 2.16(3H, s); 2.40(2H, t); 2.54(2H, t); 5.44(1H, s); 6.56(1H, s); 6.94(2H, d); 7.10(1H, m). |
| 4 | 48 | 1.62, 1.64, 1.65(4×3H, 3s); 1.80 and 1.81(2×3H, 2s); 2.67 and 2.77(2×3H, 2s); 5.18 and 5.40(2H, 2s); 6.64 and 6.82(2H, 2bs); 6.98 and 7.06(2×2H, 2s); 7.10 and 7.12(2H, 2s). |
| 4 | 54 | 1.67, 1.69 and 1.70(4×3H, 3s); 2.69 and 2.77(2×3H, 2s); 3.37(3H, s); 4.11(2H, s); 5.19 and 5.36(2H, 2s); 6.63 and 6.86(2H, 2bs); 6.98 and 7.06(2×2H, 2s); 7.13 and 7.14(2H, 2s). |
| 4 | 95 | 1.66(3H, s); 1.67(3H, s); 1.82(3H, s); 3.14(3H, s); 5.27(1H, s); 6.73(1H, bs); 7.04(2H, d); 7.15(1H, t). |
| 4 | 101 | 1.68(3H, s); 1.70(3H, s); 3.13(3H, s); 3.35(3H, s); 4.10(2H, s); 5.30(1H, s); 6.78(1H, bs); 7.02(2H, s); 7.13(1H, s). |
| 9 | 1 | 1.67(3H, s); 1.68(3H, s); 1.82(3H, s); 2.15(3H, s); 2.36(6H, s); 5.42(3H, s); 6.71(1H, bs); 6.75(2H, s). |
| 11 | 32 | 1.67(6H, s); 1.83(3H, s); 2.20(3H, s); 5.52(1H, s); 6.46(1H, s); 6.92(2H, s). |
| 12 | 1 | 1.67(3H, s); 1.68(3H, s); 1.82(3H, s); 2.18(3H, s); 3.78(6H, s); 5.46(1H, s); 6.19(3H, s); 6.70(1H, bs). |
| 12 | 20 | 1.73(6H, s); 2.21(3H, s); 3.38(3H, s); 4.12(2H, s); 5.62(1H, s); 6.72(1H, s); 7.18(1H, d); 7.74(1H, dd); 8.06(1H, d); 8.25(1H, d); 8.82(1H, d). |
| 12 | 34 | 1.72(3H, s); 1.73(3H, s); 2.20(3H, s); 3.39(3H, s); 4.12(2H, s); 5.56(1H, s); 6.77(1H, s); 7.22(1H, dd); 7.58(1H, m); 8.09(1H, d); 8.92(1H, s). |
| 16 | 1 | 1.68(6H, s); 1.83(3H, s); 2.17(3H, s); 3.83(3H, s); 5.45(1H, s); 6.59(1H, bs); 6.79(1H, t); 6.89(2H, m). |
| 16 | 48 | 1.61, 1.63, 1.65 and 1.66(12H, 4s); 1.81 and 1.82(6H, 2s); 2.69 and 2.79(6H, 2s); 3.83 and 3.84(6H, 2s); 5.20 and 5.42(2H, 2s); 6.66 and 6.83(2H, 2bs); 6.86(1H, t); 6.92(3H, m); 6.98(2H, m). |
| 16 | 95 | 1.65(3H, s); 1.67(3H, s); 1.81(3H, s); 3.15(3H, s); 3.83(3H, s); 5.37(1H, s); 6.83(1H, s); 6.91(1H, s); 6.93(1H, s); 6.96(1H, s). |
| 17 | 1 | 1.68(6H, s); 1.83(3H, s); 2.17(3H, s); 3.79(3H, s); 5.43(1H, s); 6.46(1H, s); 6.63(3H, s). |
| 17 | 48 | 0.63, 1.65 and 1.66(12H, 3s); 1.80 and 1.82(6H, 2s); 2.68 and 2.76(6H, 2s); 3.78 and 3.79(6H, 2s); 5.17 and 5.38(2H, 2s); 6.54(1H, t); 6.62(1H, t); 6.67(4H, m); 6.73(1H, t); 6.82(1H, bs). |
| 17 | 95 | 1.66(3H, s); 1.68(3H, s); 1.82(3H, s); 3.14(3H, s); 3.80(3H, s); 5.23(1H, s); 6.58(1H, s); 6.70(3H, m). |

TABLE 142-continued

This table gives characterising data (NMR, melting point or refractive index data) for compounds that are listed in Tables 1 to 129.

| Compound No. | Table No. | (Solvent CDCl$_3$): $^1$H NMR chemical shifts in ppm from TMS, or melting point (mpt) or refractive index (n$_D$$^{30}$) |
|---|---|---|
| 21 | 20 | 1.68(6H, s); 1.86(2H, q); 2.22(3H, s); 2.40(2H, t); 3.66(2H, t); 5.62(1H, s); 6.68(1H, s); 7.18(1H, m); 7.48(1H, dd); 8.04(1H, d); 8.26(1H, m); 8.82(1H, d). |
| 21 | 34 | 1.68(6H, s); 1.82–1.90(2H, m); 2.22(3H, s); 2.40(2H, t); 2.56(2H, t); 5.54(1H, s); 6.72(1H, s); 7.24(1H, dd); 7.58(1H, d); 8.09(1H, d); 8.92(1H, s). |
| 22 | 1 | 1.67(3H, s); 1.68(3H, s); 1.82(3H, s); 2.15(3H, s); 5.42(1H, s); 6.69(1H, bs); 6.95(2H, d); 7.30(2H, s). |
| 23 | 1 | 1.60(3H, s); 1.61(3H, s); 1.75(3H, s); 2.08(3H, s); 5.36(1H, s); 6.84(2H, d); 7.36(2H, s). |
| 25 | 31 | 1.73(6H, s); 2.17(3H, s); 3.38(3H, s); 4.12(2H, s); 5.50(1H, s); 6.63(1H, bs); 7.38(1H, t); 8.31(1H, d); 8.33(1H, d). |
| 36 | 1 | 1.69(3H, s); 1.70(3H, s); 1.83(3H, s); 2.16(3H, s); 2.61(3H, s); 5.55(1H, s); 6.74(1H, bs); 7.23(1H, dd); 7.45(1H, t); 7.62(1H, m); 7.67(1H, d). |
| 38 | 1 | 1.68(6H, 2s); 1.81(31H, s); 2.18(3H, s); 5.48(1H, s); 6.67(1H, bs); 6.90(1H, s); 6.96(2H, m); 7.36(1H, t). |
| 42 | 1 | 1.68(6H, s); 1.82(3H, s); 2.17(3H, s); 5.43(1H, s); 6.57(3H, m); 6.63(1H, bs). |
| 90 | 20 | 1.70(6H, s); 1.95(2H, q); 2.22(3H, s); 2.40(2H, t); 3.68(2H, t); 5.62(1H, s); 6.68(1H, s); 7.18(1H, m); 7.48(1H, dd); 8.04(1H, d); 8.26(1H, m); 8.82(1H, d). |
| 90 | 34 | 1.68(6H, s); 1.92–2.00(2H, m); 2.20(3H, s); 2.40(2H, t); 3.66(2H, t); 5.54(1H, s); 6.72(1H, s); 7.22–7.26(1H, dd); 7.58(1H, d); 8.09(1H, d); 8.92(1H, s). |
| 91 | 31 | 1.68(6H, s); 1.84(3H, s); 2.18(3H, s); 5.48(1H, s); 6.62(1H, bs); 7.52(1H, m); 8.34(1H, d); 8.42(1H, m). |
| 91 | 125 | 1.67(3H, s); 1.68(3H, s); 1.84(3H, s); 3.18(3H, s); 5.32(1H, s); 6.82(1H, s); 7.66(1H, m); 8.44(1H, s); 8.46(1H, s). |
| 135 | 1 | 1.67(3H, s); 1.68(3H, s); 1.82(3H, s); 2.16(3H, s); 2.36(3H, s); 2.43(3H, s); 5.43(1H, s); 6.73(1H, bs); 6.85(2H, m); 7.17(1H, d). |
| 136 | 1 | 1.66(3H, s); 1.67(3H, s); 1.81(3H, s); 2.15(3H, s); 5.44(1H, s); 6.70(4H, m); 7.04(2H, d); 7.14(1H, t); 7.27(2H, t); 7.36(2H, t). |
| 148 | 31 | 1.68(3H, s); 1.70(3H, s); 1.82–1.90(2H, m); 2.16(3H, s) 2.38–2.42(2H, t); 2.54–2.58(2H, t); 5.50(1H, s); 6.62(1H, s); 7.38(1H, m); 8.31(2H, m). |
| 149 | 31 | 1.04(3H, t); 1.62(6H, s); 1.92–2.04(4H, m); 2.38–2.42(2H, t); 3.68(2H, t); 4.46(1H, t); 6.30(1H, s); 7.26(1H, m); 8.28(2H, m). |
| 319 | 125 | 1.68(6H, s); 1.82(3H, s); 3.18(3H, s); 5.50(1H, s); 7.18(1H, s); 7.24(1H, s); 8.06(1H, s); 8.24(1H, s). |

EXAMPLE 34

This Example illustrates the fungicidal properties of compounds of formula (1).

The compounds were tested in a leaf disk assay, with methods described below. The test compounds were dissolved in DMSO and diluted into water to 200 ppm. In the case of the test on *Pythium ultimum*, they were dissolved in DMSO and diluted into water to 20 ppm.

*Erysiphe graminis* f.sp. *hordei* (barley powdery mildew): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Erysiphe graminis* f.sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Puccinia recondita* f.sp. *tritici* (wheat brown rust): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity.

*Septoria nodorum* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyrenophora teres* (barley net blotch): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyricularia oryzae* (rice blast): Rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): Bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Pythiiun ultimum* (Damping off): Mycelial fragments of the fungus, prepared from a fresh liquid culture, were mixed into potato dextrose broth. A solution of the test compound in dimethyl sulphoxide was diluted with water to 20 ppm then placed into a 96-well microtiter plate and the nutrient broth containing the fungal spores was added. The test plate was incubated at 24° C. and the inhibition of growth was determined photometrically, after 48 hours.

The following compounds (number of compound first, followed by table number in brackets) gave at least 60% control of the following fungal infection at 200 ppm:

*Plasmopara viticola*, compounds 2 (1), 2 (14), 2 (20), 2 (22), 2 (23), 2 (26), 2 (31), 2 (34), 2 (38), 2 (40), 2 (41), 2 (42), 2 (43), 3 (1), 3 (31); 3 (78), 4 (1), 4 (2), 4 (7), 4 (13), 4 (48), 4 (95), 4 (101), 9 (1), 12 (1), 12 (34), 16 (1), 16 (95), 17 (1), 21 (20), 21 (34), 22 (1), 23 (1), 25 (31), 38 (1), 42 (1), 90 (20), 90 (34), 91 (31), 148 (31), 149 (31);

*Phytophthora infestans*, compounds 2 (1), 2 (14), 2 (16), 2 (1.8), 2 (20), 2 (22), 2 (23), 2 (26), 2 (27), 2 (31), 2 (38), 2 (41), 2 (44), 3 (1), 3 (31), 3 (78), 4 (1), 4 (7), 4 (13), 4 (48), 4 (95), 4 (101), 9 (1), 12 (1), 12 (34), 16 (1), 16 (48), 17 (1), 21 (20), 21 (34), 22 (1), 23 (1), 25 (31), 38 (1), 42 (1), 90 (20), 90 (34), 91 (31), 135 (1), 148 (31), 149 (31);

*Erysiphe graminis* f.sp. *tritici*, compounds 2 (14), 2 (16), 2 (20), 2 (22), 2 (23), 2 (34), 3 (1), 4 (1), 4 (7), 9 (1), 12 (34), 16 (1), 16 (95), 17 (1), 21 (20), 38 (1), 90 (20), 90 (34), 91 (125);

*Pyricularia oryzae*, compounds 2 (16), 2 (42), 17 (95);

*Botrytis cinerea*, compounds 2 (1), 2 (22), 2 (27), 3 (1), 4 (1), 4 (101), 9 (1), 16 (95), 17 (1), 90 (34), 136 (1);

*Pyrenophora teres*, compounds 2 (16), 17 (48);

*Erysiphe graminis* f.sp. *hordei*, compounds 2 (1), 2 (14), 2 (16), 2 (20), 2 (22), 2 (23), 2 (26), 2 (44), 2 (81), 3 (1), 3 (78), 4 (1), 4 (2), 4 (7), 4 (48), 9 (1), 12 (1), 16 (1), 16 (95), 17 (1), 21 (20), 21 (34), 23 (1), 90 (20), 90 (34), 91 (31);

*Puccinia recondita* f.sp. *tritici*, compounds 2 (16), 3 (1), 16 (95), 90 (34), 148 (31), 149 (31);

*Septoria nodorum*, compound 21 (20), 90 (20);

The following compounds (number of compound first, followed by table number in brackets) gave at least 60% control of the following fungal infection at 20 ppm:

*Pythium ultimum*, compounds 2 (1), 2 (14), 2 (16), 2 (18), 2 (20), 2 (22), 2 (23), 2 (26), 2 (27), 2 (31), 2 (34), 2 (38), 2 (41), 2 (42), 2 (44), 3 (1), 3 (31), 3 (78), 4 (1), 4 (7), 4 (13), 4 (48), 4 (95), 4 (101), 9 (1), 12 (1), 12 (34), 16 (1), 17 (1), 21 (20), 21 (34), 22 (1), 23 (1), 25 (31), 36 (1), 38 (1), 42 (1), 90 (20), 90 (34), 91 (31), 135 (1), 148 (31), 149 (31).

The invention claimed is:

1. A compound of the general formula (1):

$$\text{Ar} - \text{O} - \overset{\underset{\displaystyle R^1}{\displaystyle S(O)_n}}{\text{C}} - \overset{\displaystyle O}{\text{C}} - \overset{\underset{\displaystyle R^2}{\displaystyle N}}{\text{N}} - \overset{\underset{\displaystyle R^3}{\displaystyle |}}{\underset{\displaystyle R^4}{\text{C}}} - \text{C} \equiv \text{C} - R^5 \quad (1)$$

wherein

Ar is a group of the formula (B1):

(B1)

wherein L and M are independently N,N-oxide or CQ, except that no more than one of L or M is N-oxide;

$K^a$ and $K^b$ are H;

V is H, halo, or $C_{1-6}$ alkyl;

Q is H, halo, $C_{1-8}$ alkyl, $C_{3-6}$ cycloalkyl, halo($C_{1-8}$)alkyl;

$R^1$ is methyl or ethyl;

$R^2$ is H;

$R^3$ and $R^4$ are independently $C_{1-3}$ alkyl, provided that their combined total of carbon atoms does not exceed 4, or $R^3$ and $R^4$ join with the carbon atom to which they are attached to form a 3 or 4 membered carbocyclic ring;

$R^5$ is H, $C_{1-4}$ alkyl in which the alkyl group is optionally substituted with halo, hydroxy, $C_{1-6}$ alkoxy, cyano, or $R^5$ is optionally substituted phenyl or optionally substituted thienyl, in which the optionally substituted phenyl and thienyl rings or moieties of the $R^5$ values are optionally substituted with one, two or three substituents selected from halo, hydroxy, $C_{1-4}$ alkyl, $C_{1-4}$ alkoxy, and nitro; and n is 0, 1 or 2.

2. A compound according to claim 1 wherein Ar is a group of the formula (B):

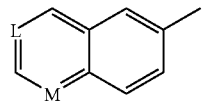

wherein one of L and M is N and the other is CQ; Q is H, halo, $C_{1-8}$ alkyl, $C_{3-6}$ cycloalkyl, halo($C_{1-8}$)alkoxy;
$R^1$ is methyl or ethyl;
$R^2$ is H;
$R^3$ and $R^4$ are independently $C_{1-3}$ alkyl, provided that their combined total of carbon atoms does not exceed 4, or
$R^3$ and $R^4$ join with the carbon atom to which they are attached to form a 3 or 4 membered carbocyclic ring;
$R^5$ is H, $C_{1-4}$ alkyl in which the alkyl is optionally substituted with halo, hydroxy, $C_{1-6}$ alkoxy or cyano, or
$R^5$ is optionally substituted phenyl or optionally substituted thienyl,
in which the optionally substituted phenyl and thienyl rings of the $R^5$ values are optionally substituted with one, two or three substituents selected from halo, hydroxy, $C_{1-4}$ alkyl, $C_{1-4}$ alkoxy, and nitro; and
n is 0, 1 or 2.

3. A compound according to claim 1 in which M is N and L is CQ, or L and M are both N, or L is N and M is CQ, or L and M are both CQ and Q is H or halo.

4. A compound according to claim 1 wherein both $R^3$ and $R^4$ are methyl.

5. A compound according to claim 1 wherein $R^5$ is H, methyl, hydroxymethyl, methoxymethyl, 1-methoxyethyl, 3-cyano-n-propyl, 3-chloro-n-propyl, phenyl, 4-fluoro-phenyl, thien-2-yl or thien-3-yl.

6. A compound according to claim 1 wherein $R^3$ and $R^4$ are both methyl; and $R^5$ is H, methyl, hydroxymethyl, methoxymethyl, 1-methoxyethyl, 3-cyano-n-propyl, 3-chloro-n-propyl, phenyl, 4-fluoro-phenyl, thien-2-yl, or thien-3-yl.

7. A compound according to claim 1 in which L and M are independently N,N-oxide or CQ, except that no more than one of L or M is N-oxide; Q is H or halo; $R_3$ and $R_4$ are both methyl; and $R_5$ is H, methyl, hydroxymethyl, methoxymethyl, 1-methoxyethyl, 3-cyano-n-propyl, 3-chloro-n-propyl, phenyl, thien-2-yl or thien-3-yl.

8. A fungicidal composition comprising a fungicidally effective amount of a compound of formula (1) according to claim 1 and a suitable carrier or diluent therefor.

9. A method of combating or controlling phytopathogenic fungi which comprises applying a fungicidally effective amount of a compound of formula (1) according to claim 1 to a plant, to a seed of a plant, to the locus of the plant or seed or to soil or any other plant growth medium.

10. A method of combating or controlling phytopathogenic fungi which comprises applying a fungicidally effective amount of a composition according to claim 8 to a plant, to a seed of a plant, to the locus of the plant or seed or to soil or any other plant growth medium.

* * * * *